(12) United States Patent
Hans et al.

(10) Patent No.: US 9,359,413 B2
(45) Date of Patent: Jun. 7, 2016

(54) MICROORGANISM AND METHOD FOR THE FERMENTATIVE PRODUCTION OF AN ORGANIC-CHEMICAL COMPOUND

(75) Inventors: Stephan Hans, Osnabrück (DE); Brigitte Bathe, Salzkotten (DE); Alexander Reth, Bielefeld (DE); Wilfried Claes, Bielefeld (DE); Reinhard Krämer, Jülich (DE); Gerd Seibold, Köln (DE); Alexander Henrich, Köln (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 13/438,665

(22) Filed: Apr. 3, 2012

(65) Prior Publication Data

US 2012/0252075 A1 Oct. 4, 2012

Related U.S. Application Data

(60) Provisional application No. 61/533,783, filed on Sep. 12, 2011.

(30) Foreign Application Priority Data

Apr. 4, 2011 (DE) .......................... 10 2011 006 716

(51) Int. Cl.
| | | |
|---|---|---|
| C12P 13/04 | (2006.01) | |
| C12P 13/08 | (2006.01) | |
| C12N 1/20 | (2006.01) | |
| C07K 14/34 | (2006.01) | |

(52) U.S. Cl.
CPC .................. *C07K 14/34* (2013.01); *C12P 13/08* (2013.01)

(58) Field of Classification Search
CPC ............ C12N 1/20; C12N 9/14; C12P 13/08; C12Y 306/01003; C07K 14/34
USPC ...................... 435/252.32, 195, 115
See application file for complete search history.

(56) References Cited

U.S. PATENT DOCUMENTS

| | | | |
|---|---|---|---|
| 3,189,526 A | 6/1965 | Kinoshita et al. | |
| 4,656,135 A | 4/1987 | Tsuchida et al. | |
| 5,188,948 A | 2/1993 | Katsurada et al. | |
| 5,275,940 A | 1/1994 | Kino et al. | |
| 5,294,547 A | 3/1994 | Tsuchida et al. | |
| 5,431,933 A | 7/1995 | Binder et al. | |
| 5,521,074 A | 5/1996 | Katsumata et al. | |
| 5,563,052 A | 10/1996 | Katsumata et al. | |
| 5,595,889 A | 1/1997 | Richaud et al. | |
| 5,605,818 A | 2/1997 | Katsumata et al. | |
| 5,693,781 A | 12/1997 | Zupancic et al. | |
| 5,989,875 A | 11/1999 | Kojima et al. | |
| 6,197,590 B1 | 3/2001 | Richaud et al. | |
| 6,340,486 B1 | 1/2002 | Binder et al. | |
| 6,465,025 B2 | 10/2002 | Binder et al. | |
| 6,884,614 B1 * | 4/2005 | Pompejus et al. | ......... 435/252.3 |
| 6,962,805 B2 | 11/2005 | Asakura et al. | |
| 7,332,310 B2 | 2/2008 | Nakagawa et al. | |
| 7,416,740 B2 | 8/2008 | Kushiki et al. | |
| 7,883,878 B2 | 2/2011 | Kushiki et al. | |
| 7,968,699 B2 | 6/2011 | Haefner et al. | |
| 8,071,365 B2 | 12/2011 | Kroger et al. | |
| 2002/0103357 A1 | 8/2002 | Bathe et al. | |
| 2002/0127661 A1 | 9/2002 | Farwick et al. | |
| 2002/0197605 A1 | 12/2002 | Nakagawa et al. | |
| 2005/0019877 A1 | 1/2005 | Zelder et al. | |
| 2006/0228712 A1 | 10/2006 | Nakagawa et al. | |
| 2007/0072274 A1 | 3/2007 | Zelder et al. | |
| 2007/0259408 A1 | 11/2007 | Bathe et al. | |
| 2008/0050786 A1 | 2/2008 | Bathe et al. | |
| 2008/0268502 A1 | 10/2008 | Haefner et al. | |
| 2008/0274516 A1 | 11/2008 | Kroger et al. | |
| 2009/0004705 A1 | 1/2009 | Kroger et al. | |
| 2010/0062535 A1 | 3/2010 | Kroger et al. | |

FOREIGN PATENT DOCUMENTS

| | | |
|---|---|---|
| EP | 0 332 488 | 9/1989 |
| EP | 0 533 039 A1 | 3/1993 |
| EP | 0 534 865 A1 | 3/1993 |
| EP | 0 629 699 A2 | 12/1994 |
| EP | 0 834 559 A1 | 4/1998 |

(Continued)

OTHER PUBLICATIONS

Henrich, A.W., "Characterization of Maltose and Trehalose Transport in Coryebacterium glutamicum", Dissertation, Feb. 2011.*
Silva et al., "The High-Affinity Maltose/Trehalose ABC Transporter in the Extremely Thermophilic Bacterium Thermus thermophilus HB27 Also Recognizes Sucrose and Palatinose", J. Bacteriol. 187:1210-1218, 2005.*
Jochmann et al., Microbiology 155:1459-1477, 2009.*
UniProt Accession No. Q8NSF1, Aug. 2010, 2 pages.*
UniProt Accession No. Q8NSF2, Aug. 2010, 2 pages.*
UniProt Accession No. Q8NSE9, Aug. 2010, 2 pages.*
GenBank Accession No. NC_006958, May 2009, 4 pages.*
UniProt Accession No. Q6M753, Aug. 2010, 1 page.*

(Continued)

*Primary Examiner* — David J Steadman
(74) *Attorney, Agent, or Firm* — Law Office of: Michael A. Sanzo, LLC

(57) ABSTRACT

The invention relates to a microorganism which produces and/or secretes an organic-chemical compound, wherein the microorganism has increased expression, compared to the particular starting strain, of one or more protein subunits of the ABC transporter having the activity of a trehalose importer, said microorganism being capable of taking up trehalose from the medium; and to a method for the production of an organic-chemical compound, using the microorganism according to the invention, wherein accumulation of trehalose in the fermentation broth is reduced or avoided.

20 Claims, 2 Drawing Sheets

(56) References Cited

FOREIGN PATENT DOCUMENTS

| | | |
|---|---|---|
| EP | 1 108 790 A2 | 6/2001 |
| EP | 1 331 220 A2 | 7/2003 |
| EP | 1 881 076 A1 | 1/2008 |
| EP | 1 918 378 A1 | 5/2008 |
| EP | 2 107 128 A2 | 10/2009 |
| GB | 1 439 728 | 6/1976 |
| WO | WO 02/22669 A1 | 3/2002 |
| WO | WO 02/26989 A1 | 4/2002 |
| WO | WO 03/014330 A2 | 2/2003 |
| WO | WO 03/040373 A2 | 5/2003 |
| WO | WO 03/040681 A1 | 5/2003 |
| WO | WO 2004/054381 A1 | 7/2004 |
| WO | WO 2004/069996 A2 | 8/2004 |
| WO | WO 2005/021772 A1 | 3/2005 |
| WO | WO 2006/069711 A1 | 7/2006 |
| WO | WO 2007/011939 A2 | 1/2007 |
| WO | WO 2007/113127 A1 | 10/2007 |

OTHER PUBLICATIONS

Blombach et al., Appl. Microbiol. Biotechnol. 86:1313-1322, 2010.*
Carpinelli et al., Appl. Environ. Microbiol. 72:1949-1955, 2006.*
International Search Report for PCT/EP2012/055359 filed Mar. 27, 2012.
XP002683459; "Full ABC transporter, membrane spanning protein," UniProtKB Database accession No. Q8NSF1; initial entry (2002).
XP002683460; "Putative ABC transporter permease protein," UniProtKB Database accession No. Q8FRL2 (2003).
Amador, et al., "Structure and organization of the rrnD operon of 'Brevibacterium lactofermentum': analysis of the 16S rRNA gene," *Microbiology* 145:915-924 (1999).
Blombach, et al., "Acetohydroxyacid Synthase, a Novel Target for Improvement of L-Lysine Production by *Corynehacterium glutamicum*," *Appl. and Env. Microbiol.* 75(2):419-427 (2009).
Cerdeño-Tárraga, et al., "The complete genome sequence and analysis of *Corynebacterium diphtheriae* NCTC13129," *Nucleic Acids Research* 31(22):6516-6523 (2003).
Feng, et al., "Progressive Sequence Alignment as a Prerequisite to Correct Phylogenetic Trees," *J. Mol. Evol.* 25:351-360 (1987).
Hamilton, et al., "New Method for Generating Deletions and Gene Replacements in *Escherichai coli*," *J. Bacteriol.* 171(9):4617-4622 (Sep. 1989).
Higgins, et al., "Fast and sensitive multiple sequence alignments on a microcomputer," *CABIOS* 5(2):151-153 (1989).
Ikeda and Nakagawa, "The *Corynebacterium glutamicum* genome: features and impacts on biotechnological processes," *Appl. Microbiol. Biotechnol.* 62:99-109 (2003).
Kalinowski, et al., "The complete *Corynebacterium glutamicum* ATCC 13032 genome sequence and its impact on the production of L-aspartate-derived amino acids and vitamins," *J. Biotechnol.* 104:5-25 (2003).
Liebl, et al., "Transfer of *Brevibacterium divaricatum* DSM 20297$^T$, "*Brevibacterium flavum*" DSM 20411, "*Brevibacterium lactofermentum*" DSM 20412 and DSM 1412, and *Corynebacterium lilium* DSM 20137$^T$ to *Corynebacterium glutamicum* and Their Distinction by rRNA Gene Restriction Patterns," *International Journal of Systematic Bacteriology* 41(2):255-260 (Apr. 1991).
Link, et al., "Methods for Generating Precise Deletions and Insertions in the Genome of Wild-Type *Escherichia coli*: Application to Open Reading Frame Characterization," *J. Bacteriol.* 179(20):6228-6237 (Oct. 1997).
Morinaga, et al.,"Expression of *Escherichia coli* promoters in *Brevibacterium lactofermentum* using the shuttle vector pEB003," *J. Biotechnol.* 5:305-312 (1987).
Needleman and Wunsch, "A General Method Applicable to the Search for Similarities the Amino Acid Sequence of Two Proteins," *J. Mol. Biol.* 48:443-453 (1970).
Nishio, et al., "Comparative Complete Genome Sequence Analysis of the Amino Acid Replacements Responsible for the Thermostability of *Corynebacterium efficiens*," *Genome Research* 13(7):1572-1579 (2003).
Pühler and Tauch, "Editorial: A new era in *Corynebacterium glutamicum* biotechnology," *J. Biotechnol.* 104:1-3 (2003).
Smith and Waterman, "Comparison of Biosequences," *Adv. Appl. Math.* 2:482-489 (1991).
Stansen, et al., "Characterization of a *Corynebacterium glutamicum* Lactate Utilization Operon Induced during Temperature-Triggered Glutamate Production," *Applied and Environmental Microbiology* 71(10):5920-5928 (Oct. 2005).
Tauch, et al., "Complete Genome Sequence and Analysis of the multiresistant Nosocomial Pathogen *Corynebacterium jeikeium* K411, a Lipid-Requiring Bacterium of the Human Skin Flora," *J. Bacteriol.* 187(13):4671-4682 (Jul. 2005).
Tauch, et al., Plasmids in *Corynebacterium glutamicum* and their molecular classification by comparative genomics, *J. Biotechnol.* 104(1-3):27-40 (2003).
Tsuchiya, et al., "Genetic Control Systems of *Escherichia coli* Can Confer Inducible Expression of Cloned Genes in Coryneform Bacteria," *Bio/Technology* 6:428-430 (1988).
Vašicová, et al., "Analysis of the *Corynebacterium glutamicum dapA* Promoter," *J. Bacteriol.* 181(19):6188-6191 (Oct. 1999).
Yu and Court, et al., "A new system to place single copies of genes, sites and *lacZ* fusions on the *Escherichia coli* chromosome[1,2]," *Gene* 223, 233:77-81(1998).
Yukawa, et al., "Comparative analysis of the *Corynebacterium glutamicum* group and complete genome sequence of strain R," *Microbiology* 153(4):1042-1058 (2007).
Genbank accession No. CAA70125, Apr. 18, 2005.
Genbank accession No. Q8NSE8 dated Jul. 22, 2012.
XP-002677414; Database accession No. Q8NSE8 from European Search Report, May 16, 2012.
Genbank accession No. Q8FRK9 dated Jul. 22, 2012.
XP-002677415; Database accession No. Q8FRK9 from European Search Report, May 16, 2012.
Form PCT/ISA/206 for corresponding international application PCT/EP2012/055359, including an Annex with the results of a Partial Search, Sep. 26, 2012.
English language translation of portions of document, Sep. 26, 2012.
English language abstract for EP 0 534 865, Mar. 31, 1993.

\* cited by examiner

SEQUENCE LISTING

<160> NUMBER OF SEQ ID NOS: 31

<210> SEQ ID NO 1
<211> LENGTH: 1299
<212> TYPE: DNA
<213> ORGANISM: Corynebacterium glutamicum
<220> FEATURE:
<221> NAME/KEY: CDS
<222> LOCATION: (151)..(1149)
<223> OTHER INFORMATION: ATP-binding and -hydrolyzing (ATPase) protein
      of the ABC transporter having the activity of a trehalose importer

<400> SEQUENCE: 1
ctttgagctt gatgccgccc caaaagagtt gttgccaccg atcgcgaact ttggcagtag      60
ccatgcgttc tgctcctgac cttgaacagc ggtcccaatt tagacccgct aaacccacaa     120
tgtgtactgg tgctggtaat ttagtagaac atg gca acg gtc aca ttc gac aag     174
                                  Met Ala Thr Val Thr Phe Asp Lys

```
                    1               5
gtc aca atc cgg tac ccc ggc gcg gag cgc gca aca gtt cat gag ctt      222
Val Thr Ile Arg Tyr Pro Gly Ala Glu Arg Ala Thr Val His Glu Leu
     10              15                  20 gat tta gat atc gct gat ggc gag ttt ttg gtg ctc gtc ggc cct tcg      270
Asp Leu Asp Ile Ala Asp Gly Glu Phe Leu Val Leu Val Gly Pro Ser
 25              30                  35                  40 ggt tgt ggt aaa tcc act acg ctg cgt gct ttg gcg ggg ctt gag ggc      318
Gly Cys Gly Lys Ser Thr Thr Leu Arg Ala Leu Ala Gly Leu Glu Gly
                 45                  50                  55 gtg gag tcg ggt gtg atc aaa att gat ggc aag gat gtc act ggt cag      366
Val Glu Ser Gly Val Ile Lys Ile Asp Gly Lys Asp Val Thr Gly Gln
             60                  65                  70 gag ccg gcg gat cgc gat atc gcg atg gtg ttc cag aat tat gct ctg      414
Glu Pro Ala Asp Arg Asp Ile Ala Met Val Phe Gln Asn Tyr Ala Leu
         75                  80                  85 tac cct cac atg acg gtg gcg aag aat atg ggt ttt gcg ctg aag ttg      462
Tyr Pro His Met Thr Val Ala Lys Asn Met Gly Phe Ala Leu Lys Leu
     90                  95                 100 gct aag ctg ccg cag gcg cag atc gat gcg aag gtc aat gag gct gcg      510
Ala Lys Leu Pro Gln Ala Gln Ile Asp Ala Lys Val Asn Glu Ala Ala
105             110                 115                 120 gaa att ctt ggg ttg acg gag ttt ttg gat cgc aag cct aag gat tta      558
Glu Ile Leu Gly Leu Thr Glu Phe Leu Asp Arg Lys Pro Lys Asp Leu
                125                 130                 135 tcg ggt ggt cag cgt cag cgt gtg gcg atg ggt cgc gcg ttg gtg cgt      606
Ser Gly Gly Gln Arg Gln Arg Val Ala Met Gly Arg Ala Leu Val Arg
            140                 145                 150 gat ccg aag gtg ttc ctc atg gat gag ccg ctg tcc aac ctg gat gcg      654
Asp Pro Lys Val Phe Leu Met Asp Glu Pro Leu Ser Asn Leu Asp Ala
        155                 160                 165 aaa ttg cgc gtg caa acc cgc gcg gag gtc gct gct ttg cag cgt cgc      702
Lys Leu Arg Val Gln Thr Arg Ala Glu Val Ala Ala Leu Gln Arg Arg
    170                 175                 180 ctg ggc acc acc acg gtg tat gtc acc cac gat cag gtt gag gca atg      750
Leu Gly Thr Thr Thr Val Tyr Val Thr His Asp Gln Val Glu Ala Met
185                 190                 195                 200 acg atg ggc gat cgg gtt gcg gtg ctc aag gac ggg ttg ctg cag cag      798
Thr Met Gly Asp Arg Val Ala Val Leu Lys Asp Gly Leu Leu Gln Gln
                205                 210                 215 gtc gca ccg ccc agg gag ctt tac gac gcc ccg gtc aac gaa ttc gtt      846
Val Ala Pro Pro Arg Glu Leu Tyr Asp Ala Pro Val Asn Glu Phe Val
            220                 225                 230 gcg ggc ttc atc ggc tcg ccg tcc atg aac ctc ttc cct gcc aac ggg      894
Ala Gly Phe Ile Gly Ser Pro Ser Met Asn Leu Phe Pro Ala Asn Gly
        235                 240                 245 cac aag atg ggt gtg cgc ccg gag aag atg ctg gtc aat gag acc cct      942
His Lys Met Gly Val Arg Pro Glu Lys Met Leu Val Asn Glu Thr Pro
    250                 255                 260 gag ggt ttc aca agc att gat gct gtg gtg gat atc gtc gag gag ctt      990
Glu Gly Phe Thr Ser Ile Asp Ala Val Val Asp Ile Val Glu Glu Leu
265                 270                 275                 280 ggc tcc gaa tcg tat gtt tat gcc act tgg gag ggc cac cgc ctg gtg     1038
Gly Ser Glu Ser Tyr Val Tyr Ala Thr Trp Glu Gly His Arg Leu Val
                285                 290                 295 gcc cgt tgg gtg gaa ggc ccc gtg cca gcc cct ggc acg cct gtg act     1086
Ala Arg Trp Val Glu Gly Pro Val Pro Ala Pro Gly Thr Pro Val Thr
            300                 305                 310 ttt tcc tat gat gcg gcg cag gcg cat cat ttc gat ctg gag tcg ggc     1134
Phe Ser Tyr Asp Ala Ala Gln Ala His His Phe Asp Leu Glu Ser Gly
```

```
Phe Ser Tyr Asp Ala Ala Gln Ala His His Phe Asp Leu Glu Ser Gly
            315                 320                 325 gag cgt atc gct tag tttcggacgt ggggaggcgt cgaaaagcat ctttattttt      1189
Glu Arg Ile Ala
        330 gaccctccgg gggtgattta acctaaaatt ccacacaaac gtgttcgagg tcattagatt    1249 gataagcatc tgttgttaag aaaggtgact tcctatgtcc tcgatttccc               1299

<210> SEQ ID NO 2
<211> LENGTH: 332
<212> TYPE: PRT
<213> ORGANISM: Corynebacterium glutamicum

<400> SEQUENCE: 2

Met Ala Thr Val Thr Phe Asp Lys Val Thr Ile Arg Tyr Pro Gly Ala
1               5                   10                  15

Glu Arg Ala Thr Val His Glu Leu Asp Leu Asp Ile Ala Asp Gly Glu
            20                  25                  30

Phe Leu Val Leu Val Gly Pro Ser Gly Cys Gly Lys Ser Thr Thr Leu
        35                  40                  45

Arg Ala Leu Ala Gly Leu Glu Gly Val Glu Ser Gly Val Ile Lys Ile
    50                  55                  60

Asp Gly Lys Asp Val Thr Gly Gln Glu Pro Ala Asp Arg Asp Ile Ala
65                  70                  75                  80

Met Val Phe Gln Asn Tyr Ala Leu Tyr Pro His Met Thr Val Ala Lys
                85                  90                  95

Asn Met Gly Phe Ala Leu Lys Leu Ala Lys Leu Pro Gln Ala Gln Ile
            100                 105                 110

Asp Ala Lys Val Asn Glu Ala Ala Glu Ile Leu Gly Leu Thr Glu Phe
        115                 120                 125

Leu Asp Arg Lys Pro Lys Asp Leu Ser Gly Gly Gln Arg Gln Arg Val
    130                 135                 140

Ala Met Gly Arg Ala Leu Val Arg Asp Pro Lys Val Phe Leu Met Asp
145                 150                 155                 160

Glu Pro Leu Ser Asn Leu Asp Ala Lys Leu Arg Val Gln Thr Arg Ala
                165                 170                 175

Glu Val Ala Ala Leu Gln Arg Arg Leu Gly Thr Thr Thr Val Tyr Val
            180                 185                 190

Thr His Asp Gln Val Glu Ala Met Thr Met Gly Asp Arg Val Ala Val
        195                 200                 205

Leu Lys Asp Gly Leu Leu Gln Gln Val Ala Pro Arg Glu Leu Tyr
    210                 215                 220

Asp Ala Pro Val Asn Glu Phe Val Ala Gly Phe Ile Gly Ser Pro Ser
225                 230                 235                 240

Met Asn Leu Phe Pro Ala Asn Gly His Lys Met Gly Val Arg Pro Glu
                245                 250                 255

Lys Met Leu Val Asn Glu Thr Pro Glu Gly Phe Thr Ser Ile Asp Ala
            260                 265                 270

Val Val Asp Ile Val Glu Glu Leu Gly Ser Glu Ser Tyr Val Tyr Ala
        275                 280                 285

Thr Trp Glu Gly His Arg Leu Val Ala Arg Trp Val Glu Gly Pro Val
    290                 295                 300

Pro Ala Pro Gly Thr Pro Val Thr Phe Ser Tyr Asp Ala Ala Gln Ala
305                 310                 315                 320
```

His His Phe Asp Leu Glu Ser Gly Glu Arg Ile Ala
            325                 330

<210> SEQ ID NO 3
<211> LENGTH: 1575
<212> TYPE: DNA
<213> ORGANISM: Corynebacterium glutamicum
<220> FEATURE:
<221> NAME/KEY: CDS
<222> LOCATION: (151)..(1425)
<223> OTHER INFORMATION: periplasmic (or lipoprotein) substrate-binding
      protein of the ABC transporter having the activity of a trehalose
      importer

<400> SEQUENCE: 3

| | |
|---|---:|
| cgagcgtatc gcttagtttc ggacgtgggg aggcgtcgaa aagcatcttt attttgacc | 60 |
| ctccgggggt gatttaacct aaaattccac acaaacgtgt tcgaggtcat tagattgata | 120 |
| agcatctgtt gttaagaaag gtgacttcct atg tcc tcg att tcc cgc aag acc | 174 |
|                                  Met Ser Ser Ile Ser Arg Lys Thr |  |
|                                  1               5               |  |

| | |
|---|---:|
| ggc gcg tca ctt gca gcc acc aca ctg ttg gca gcg atc gca ctg gcc | 222 |
| Gly Ala Ser Leu Ala Ala Thr Thr Leu Leu Ala Ala Ile Ala Leu Ala |  |
|     10              15                  20                      |  |

| | |
|---|---:|
| ggt tgt agt tca gac tca agc tcc gac tcc aca gat tcc acc gct agc | 270 |
| Gly Cys Ser Ser Asp Ser Ser Ser Asp Ser Thr Asp Ser Thr Ala Ser |  |
| 25              30              35              40              |  |

| | |
|---|---:|
| gaa ggc gca gac agc cgc ggc ccc atc acc ttt gcg atg ggc aaa aac | 318 |
| Glu Gly Ala Asp Ser Arg Gly Pro Ile Thr Phe Ala Met Gly Lys Asn |  |
|                 45              50              55              |  |

| | |
|---|---:|
| gac acc gac aaa gtc att ccg atc atc gac cgc tgg aac gaa gcc cac | 366 |
| Asp Thr Asp Lys Val Ile Pro Ile Ile Asp Arg Trp Asn Glu Ala His |  |
|             60              65              70                  |  |

| | |
|---|---:|
| ccc gat gag cag gta acg ctc aac gaa ctc gcc ggt gaa gcc gac gcg | 414 |
| Pro Asp Glu Gln Val Thr Leu Asn Glu Leu Ala Gly Glu Ala Asp Ala |  |
|         75              80              85                      |  |

| | |
|---|---:|
| cag cgc gaa acc ctc gtg caa tcc ctg cag gcc ggc aac tct gac tac | 462 |
| Gln Arg Glu Thr Leu Val Gln Ser Leu Gln Ala Gly Asn Ser Asp Tyr |  |
|     90              95              100                         |  |

| | |
|---|---:|
| gac gtc atg gcg ctc gac gtc atc tgg acc gca gac ttc gcg gca aac | 510 |
| Asp Val Met Ala Leu Asp Val Ile Trp Thr Ala Asp Phe Ala Ala Asn |  |
| 105             110             115             120             |  |

| | |
|---|---:|
| caa tgg ctc gca cca ctt gaa ggc gac ctc gag gta gac acc tcc gga | 558 |
| Gln Trp Leu Ala Pro Leu Glu Gly Asp Leu Glu Val Asp Thr Ser Gly |  |
|                 125             130             135             |  |

| | |
|---|---:|
| ctg ctg caa tcc acc gtg gat tcc gca acc tac aac ggc acc ctc tac | 606 |
| Leu Leu Gln Ser Thr Val Asp Ser Ala Thr Tyr Asn Gly Thr Leu Tyr |  |
|             140             145             150                 |  |

| | |
|---|---:|
| gca ctg cca cag aac acc aac ggc cag cta ctg ttc cgc aac acc gaa | 654 |
| Ala Leu Pro Gln Asn Thr Asn Gly Gln Leu Leu Phe Arg Asn Thr Glu |  |
|         155             160             165                     |  |

| | |
|---|---:|
| atc atc cca gaa gca cca gca aac tgg gct gac ctc gtg gaa tcc tgc | 702 |
| Ile Ile Pro Glu Ala Pro Ala Asn Trp Ala Asp Leu Val Glu Ser Cys |  |
|     170             175             180                         |  |

| | |
|---|---:|
| acg ctt gct gaa gaa gca ggc gtt gat tgc ctg acc act cag ctc aag | 750 |
| Thr Leu Ala Glu Glu Ala Gly Val Asp Cys Leu Thr Thr Gln Leu Lys |  |
| 185             190             195             200             |  |

| | |
|---|---:|
| cag tac gaa ggc ctt tca gtg aac acc atc ggc ttc atc gaa ggt tgg | 798 |
| Gln Tyr Glu Gly Leu Ser Val Asn Thr Ile Gly Phe Ile Glu Gly Trp |  |
|                 205             210             215             |  |

| | |
|---|---:|
| gga ggc agc gtc cta gac gat gac ggc aac gtc acc gta gac agc gac | 846 |
| Gly Gly Ser Val Leu Asp Asp Asp Gly Asn Val Thr Val Asp Ser Asp |  |

```
                    220                 225                 230
gac gcc aag gca ggc ctt caa gcg ctt gtc gac ggc ttc gac gac ggc      894
Asp Ala Lys Ala Gly Leu Gln Ala Leu Val Asp Gly Phe Asp Asp Gly
            235                 240                 245 acc atc tcc aag gca tcc ctt gca gcg acc gaa gaa gaa acc aac ctc      942
Thr Ile Ser Lys Ala Ser Leu Ala Ala Thr Glu Glu Glu Thr Asn Leu
250                 255                 260 gca ttc acc gaa ggc caa acc gcc tac gcc att aac tgg cca tac atg      990
Ala Phe Thr Glu Gly Gln Thr Ala Tyr Ala Ile Asn Trp Pro Tyr Met
265                 270                 275                 280 tac acc aac tcc gaa gaa gcc gaa gca acc gca ggc aaa ttc gaa gta     1038
Tyr Thr Asn Ser Glu Glu Ala Glu Ala Thr Ala Gly Lys Phe Glu Val
                285                 290                 295 cag ccc ctc gta ggt aaa gac ggc gtc ggc gta tcc acc ctt ggt ggc     1086
Gln Pro Leu Val Gly Lys Asp Gly Val Gly Val Ser Thr Leu Gly Gly
            300                 305                 310 tac aac aac ggc atc aac gtc aac tcc gaa aac aag gca acc gcc cgc     1134
Tyr Asn Asn Gly Ile Asn Val Asn Ser Glu Asn Lys Ala Thr Ala Arg
        315                 320                 325 gac ttc atc gaa ttc atc atc aac gaa gag aac caa acc tgg ttc gcg     1182
Asp Phe Ile Glu Phe Ile Ile Asn Glu Glu Asn Gln Thr Trp Phe Ala
    330                 335                 340 gac aac tcc ttc cca cca gtt ctg gca tcc atc tac gat gat gag tcc     1230
Asp Asn Ser Phe Pro Pro Val Leu Ala Ser Ile Tyr Asp Asp Glu Ser
345                 350                 355                 360 ctt gtt gag cag tac cca tac ctg cca gca ctg aag gaa tcc ctg gaa     1278
Leu Val Glu Gln Tyr Pro Tyr Leu Pro Ala Leu Lys Glu Ser Leu Glu
                365                 370                 375 aac gca gca cca cgc cca gtg tct cct ttc tac cca gcc atc tcc aag     1326
Asn Ala Ala Pro Arg Pro Val Ser Pro Phe Tyr Pro Ala Ile Ser Lys
            380                 385                 390 gca atc cag gac aac gcc tac gca gcg ctt aac ggc aac gtc gac gtt     1374
Ala Ile Gln Asp Asn Ala Tyr Ala Ala Leu Asn Gly Asn Val Asp Val
        395                 400                 405 gac cag gca acc acc gat atg aag gca gcg atc gaa aac gct tcc agc     1422
Asp Gln Ala Thr Thr Asp Met Lys Ala Ala Ile Glu Asn Ala Ser Ser
    410                 415                 420 tag ttcggtaatt tagttcattc tccggccacc ttccctgaaa tccttagcgg          1475
atttccacaa aggtggccgg agttttgtcc tattgttggg tgtaattgaa cttgtgtgaa   1535
aggagtccgg atggcttccg gcaaagatct tcaagttttcc                        1575

<210> SEQ ID NO 4
<211> LENGTH: 424
<212> TYPE: PRT
<213> ORGANISM: Corynebacterium glutamicum

<400> SEQUENCE: 4

Met Ser Ser Ile Ser Arg Lys Thr Gly Ala Ser Leu Ala Ala Thr Thr
1               5                   10                  15

Leu Leu Ala Ala Ile Ala Leu Ala Gly Cys Ser Ser Asp Ser Ser Ser
                20                  25                  30

Asp Ser Thr Asp Ser Thr Ala Ser Glu Gly Ala Asp Ser Arg Gly Pro
            35                  40                  45

Ile Thr Phe Ala Met Gly Lys Asn Asp Thr Asp Lys Val Ile Pro Ile
        50                  55                  60

Ile Asp Arg Trp Asn Glu Ala His Pro Asp Glu Gln Val Thr Leu Asn
65                  70                  75                  80
```

-continued

```
Glu Leu Ala Gly Glu Ala Asp Ala Gln Arg Glu Thr Leu Val Gln Ser
                85                  90                  95
Leu Gln Ala Gly Asn Ser Asp Tyr Asp Val Met Ala Leu Asp Val Ile
            100                 105                 110
Trp Thr Ala Asp Phe Ala Ala Asn Gln Trp Leu Ala Pro Leu Glu Gly
        115                 120                 125
Asp Leu Glu Val Asp Thr Ser Gly Leu Leu Gln Ser Thr Val Asp Ser
    130                 135                 140
Ala Thr Tyr Asn Gly Thr Leu Tyr Ala Leu Pro Gln Asn Thr Asn Gly
145                 150                 155                 160
Gln Leu Leu Phe Arg Asn Thr Glu Ile Ile Pro Glu Ala Pro Ala Asn
                165                 170                 175
Trp Ala Asp Leu Val Glu Ser Cys Thr Leu Ala Glu Glu Ala Gly Val
            180                 185                 190
Asp Cys Leu Thr Thr Gln Leu Lys Gln Tyr Glu Gly Leu Ser Val Asn
        195                 200                 205
Thr Ile Gly Phe Ile Glu Gly Trp Gly Gly Ser Val Leu Asp Asp Asp
    210                 215                 220
Gly Asn Val Thr Val Asp Ser Asp Ala Lys Ala Gly Leu Gln Ala
225                 230                 235                 240
Leu Val Asp Gly Phe Asp Asp Gly Thr Ile Ser Lys Ala Ser Leu Ala
                245                 250                 255
Ala Thr Glu Glu Glu Thr Asn Leu Ala Phe Thr Gly Gln Thr Ala
            260                 265                 270
Tyr Ala Ile Asn Trp Pro Tyr Met Tyr Thr Asn Ser Glu Glu Ala Glu
        275                 280                 285
Ala Thr Ala Gly Lys Phe Glu Val Gln Pro Leu Val Gly Lys Asp Gly
    290                 295                 300
Val Gly Val Ser Thr Leu Gly Gly Tyr Asn Asn Gly Ile Asn Val Asn
305                 310                 315                 320
Ser Glu Asn Lys Ala Thr Ala Arg Asp Phe Ile Glu Phe Ile Ile Asn
                325                 330                 335
Glu Glu Asn Gln Thr Trp Phe Ala Asp Asn Ser Phe Pro Pro Val Leu
            340                 345                 350
Ala Ser Ile Tyr Asp Asp Glu Ser Leu Val Glu Gln Tyr Pro Tyr Leu
        355                 360                 365
Pro Ala Leu Lys Glu Ser Leu Glu Asn Ala Ala Pro Arg Pro Val Ser
    370                 375                 380
Pro Phe Tyr Pro Ala Ile Ser Lys Ala Ile Gln Asp Asn Ala Tyr Ala
385                 390                 395                 400
Ala Leu Asn Gly Asn Val Asp Val Asp Gln Ala Thr Thr Asp Met Lys
                405                 410                 415
Ala Ala Ile Glu Asn Ala Ser Ser
            420
```

<210> SEQ ID NO 5
<211> LENGTH: 756
<212> TYPE: DNA
<213> ORGANISM: Corynebacterium glutamicum
<220> FEATURE:
<221> NAME/KEY: CDS
<222> LOCATION: (151)..(606)
<223> OTHER INFORMATION: function unknown

<400> SEQUENCE: 5
aaggcagcga tcgaaaacgc ttccagctag ttcggtaatt tagttcattc tccggccacc    60

```
ttccctgaaa tccttagcgg atttccacaa aggtggccgg agttttgtcc tattgttggg      120
tgtaattgaa cttgtgtgaa aggagtccgg atg gct tcc ggc aaa gat ctt caa      174
                                 Met Ala Ser Gly Lys Asp Leu Gln
                                  1               5 gtt tcc aca ttt ggc tac atc tcc cgc tgc ccc gtg cag gtc tac gaa      222
Val Ser Thr Phe Gly Tyr Ile Ser Arg Cys Pro Val Gln Val Tyr Glu
 10              15                  20 gca atc gca gat ccc aga caa cta gaa cgc tac ttc gcc acc ggc gga      270
Ala Ile Ala Asp Pro Arg Gln Leu Glu Arg Tyr Phe Ala Thr Gly Gly
 25              30                  35                  40 gta tct ggc cgc ctc gaa acc gga tcg act gtc tat tgg gac ttc gtt      318
Val Ser Gly Arg Leu Glu Thr Gly Ser Thr Val Tyr Trp Asp Phe Val
             45                  50                  55 gat ttt ccc ggt gcg ttt ccg gtc caa gtt gtc tca gct aca cag gct      366
Asp Phe Pro Gly Ala Phe Pro Val Gln Val Val Ser Ala Thr Gln Ala
             60                  65                  70 gaa cac att gaa ctc cgc tgg gga caa gca aat gag ctg cgt tcc gtc      414
Glu His Ile Glu Leu Arg Trp Gly Gln Ala Asn Glu Leu Arg Ser Val
             75                  80                  85 aac ttc gag ttc gaa cct ttt aga aat ttc acc cgc acg aaa ctc acc      462
Asn Phe Glu Phe Glu Pro Phe Arg Asn Phe Thr Arg Thr Lys Leu Thr
 90              95                 100 atc acc gaa ggc agt tgg ccg ctc act ccc gca gga gcc caa gag gct      510
Ile Thr Glu Gly Ser Trp Pro Leu Thr Pro Ala Gly Ala Gln Glu Ala
105             110                 115                 120 ctg ggc agc cag atg gga tgg act ggc atg ctg tcc gca cta aaa gcg      558
Leu Gly Ser Gln Met Gly Trp Thr Gly Met Leu Ser Ala Leu Lys Ala
                125                 130                 135 tgg ctg gaa tac gga gtg aac ctc cgc gac ggg ttt tat aag caa tag      606
Trp Leu Glu Tyr Gly Val Asn Leu Arg Asp Gly Phe Tyr Lys Gln
                140                 145                 150 gcaatgtgtc catcacgatg tgtggcggat tatgatccat gtaacaagaa tgtgcagttt      666
cacagaactg acaatcaact tattttgacc tgacaaaagg agcgacgaca catggccaca      726
ttcaaacagg ccagaagcgc tgcctggctg                                      756

<210> SEQ ID NO 6
<211> LENGTH: 151
<212> TYPE: PRT
<213> ORGANISM: Corynebacterium glutamicum

<400> SEQUENCE: 6

Met Ala Ser Gly Lys Asp Leu Gln Val Ser Thr Phe Gly Tyr Ile Ser
 1               5                  10                  15

Arg Cys Pro Val Gln Val Tyr Glu Ala Ile Ala Asp Pro Arg Gln Leu
                 20                  25                  30

Glu Arg Tyr Phe Ala Thr Gly Gly Val Ser Gly Arg Leu Glu Thr Gly
             35                  40                  45

Ser Thr Val Tyr Trp Asp Phe Val Asp Phe Pro Gly Ala Phe Pro Val
         50                  55                  60

Gln Val Val Ser Ala Thr Gln Ala Glu His Ile Glu Leu Arg Trp Gly
 65                  70                  75                  80

Gln Ala Asn Glu Leu Arg Ser Val Asn Phe Glu Phe Glu Pro Phe Arg
                 85                  90                  95

Asn Phe Thr Arg Thr Lys Leu Thr Ile Thr Glu Gly Ser Trp Pro Leu
                100                 105                 110

Thr Pro Ala Gly Ala Gln Glu Ala Leu Gly Ser Gln Met Gly Trp Thr
```

```
            115                 120                 125
Gly Met Leu Ser Ala Leu Lys Ala Trp Leu Glu Tyr Gly Val Asn Leu
        130                 135                 140

Arg Asp Gly Phe Tyr Lys Gln
145                 150

<210> SEQ ID NO 7
<211> LENGTH: 1335
<212> TYPE: DNA
<213> ORGANISM: Corynebacterium glutamicum
<220> FEATURE:
<221> NAME/KEY: CDS
<222> LOCATION: (151)..(1185)
<223> OTHER INFORMATION: integral membrane protein (permease) of the ABC
      transporter having the activity of a trehalose importer

<400> SEQUENCE: 7
tacggagtga acctccgcga cgggttttat aagcaatagg caatgtgtcc atcacgatgt     60
gtggcggatt atgatccatg taacaagaat gtgcagtttc acagaactga caatcaactt    120
attttgacct gacaaaagga gcgacgacac atg gcc aca ttc aaa cag gcc aga    174
                                  Met Ala Thr Phe Lys Gln Ala Arg
                                    1               5 agc gct gcc tgg ctg atc gcc ccc gcc ctc gtg gtc ctt gca gtg gtg    222
Ser Ala Ala Trp Leu Ile Ala Pro Ala Leu Val Val Leu Ala Val Val
         10                  15                  20 atc gga tat ccc atc gtc cga gca att tgg cta tcc ttc cag gcc gac    270
Ile Gly Tyr Pro Ile Val Arg Ala Ile Trp Leu Ser Phe Gln Ala Asp
 25                  30                  35                  40 aaa ggc ctc gac ccc acc acc gga ctc ttc acc gac ggt ggc ttc gca    318
Lys Gly Leu Asp Pro Thr Thr Gly Leu Phe Thr Asp Gly Gly Phe Ala
                 45                  50                  55 gga cta gac aat tac ctc tac tgg ctc acc caa cga tgc atg ggt tca    366
Gly Leu Asp Asn Tyr Leu Tyr Trp Leu Thr Gln Arg Cys Met Gly Ser
             60                  65                  70 gac ggc acc atc cgt acc tgc cca ccc ggc aca cta gcc acc gac ttc    414
Asp Gly Thr Ile Arg Thr Cys Pro Pro Gly Thr Leu Ala Thr Asp Phe
         75                  80                  85 tgg cca gca cta cgc atc acg ttg ttc ttc acc gtg gtt acc gtc ggc    462
Trp Pro Ala Leu Arg Ile Thr Leu Phe Phe Thr Val Val Thr Val Gly
 90                  95                 100 ttg gaa act atc ctc ggc acc gcc atg gca ctg atc atg aac aaa gaa    510
Leu Glu Thr Ile Leu Gly Thr Ala Met Ala Leu Ile Met Asn Lys Glu
105                 110                 115                 120 ttc cgt ggc cgc gca ctt gtt cgc gca gcg att ctt atc cct tgg gca    558
Phe Arg Gly Arg Ala Leu Val Arg Ala Ala Ile Leu Ile Pro Trp Ala
                125                 130                 135 atc ccc acc gcc gtc acc gca aaa ctg tgg cag ttc atc ttc gca cca    606
Ile Pro Thr Ala Val Thr Ala Lys Leu Trp Gln Phe Ile Phe Ala Pro
            140                 145                 150 caa ggc atc atc aac tcc atg ttt gga ctt agt gtc agt tgg acc acc    654
Gln Gly Ile Ile Asn Ser Met Phe Gly Leu Ser Val Ser Trp Thr Thr
        155                 160                 165 gat ccg tgg gca gct aga gcc gcc gtc att ctt gcc gac gtc tgg aaa    702
Asp Pro Trp Ala Ala Arg Ala Ala Val Ile Leu Ala Asp Val Trp Lys
    170                 175                 180 acc aca cca ttc atg gca ctg ctg atc ctc gcc ggt ctg caa atg atc    750
Thr Thr Pro Phe Met Ala Leu Leu Ile Leu Ala Gly Leu Gln Met Ile
185                 190                 195                 200 ccg aag gaa acc tac gaa gca gcc cgc gtc gat ggc gca acc gcg tgg    798
Pro Lys Glu Thr Tyr Glu Ala Ala Arg Val Asp Gly Ala Thr Ala Trp
```

```
            205                 210                 215
cag caa ttc acc aag atc acc ctc ccg ctg gtg cgc cca gct ttg atg      846
Gln Gln Phe Thr Lys Ile Thr Leu Pro Leu Val Arg Pro Ala Leu Met
            220                 225                 230 gtg gca gta ctc ttc cgc acc ctc gat gcg cta cgc atg tat gac ctc      894
Val Ala Val Leu Phe Arg Thr Leu Asp Ala Leu Arg Met Tyr Asp Leu
            235                 240                 245 ccc gtc atc atg atc tcc agc tcc tcc aac tcc ccc acc gct gtt atc      942
Pro Val Ile Met Ile Ser Ser Ser Ser Asn Ser Pro Thr Ala Val Ile
            250                 255                 260 tcc cag ctg gtt gtg gaa gac atg cgc caa aac aac ttc aac tcc gct      990
Ser Gln Leu Val Val Glu Asp Met Arg Gln Asn Asn Phe Asn Ser Ala
265                 270                 275                 280 tcc gcc ctt tcc aca ctg atc ttc ctg ctg atc ttc ttc gtg gcg ttc     1038
Ser Ala Leu Ser Thr Leu Ile Phe Leu Leu Ile Phe Phe Val Ala Phe
                285                 290                 295 atc atg atc cga ttc ctc ggc gca gat gtt tcg ggc caa cgc gga ata     1086
Ile Met Ile Arg Phe Leu Gly Ala Asp Val Ser Gly Gln Arg Gly Ile
            300                 305                 310 aag aaa aag aaa ctg ggc gga acc aag gat gag aaa ccc acc gct aag     1134
Lys Lys Lys Lys Leu Gly Gly Thr Lys Asp Glu Lys Pro Thr Ala Lys
            315                 320                 325 gat gct gtt gta aag gcc gat tct gct gtg aag gaa gcc gct aag cca     1182
Asp Ala Val Val Lys Ala Asp Ser Ala Val Lys Glu Ala Ala Lys Pro
330                 335                 340 tga ctaaacgaac aaaaggactc atcctcaact acgccggagt ggtgttcatc          1235
ctcttctggg gactagctcc cttctactgg atggttatca ccgcactgcg cgattccaag   1295
cacacctttg acaccacccc atggccaacg cacgtcacct                         1335

<210> SEQ ID NO 8
<211> LENGTH: 344
<212> TYPE: PRT
<213> ORGANISM: Corynebacterium glutamicum

<400> SEQUENCE: 8

Met Ala Thr Phe Lys Gln Ala Arg Ser Ala Ala Trp Leu Ile Ala Pro
1               5                   10                  15

Ala Leu Val Val Leu Ala Val Val Ile Gly Tyr Pro Ile Val Arg Ala
            20                  25                  30

Ile Trp Leu Ser Phe Gln Ala Asp Lys Gly Leu Asp Pro Thr Thr Gly
        35                  40                  45

Leu Phe Thr Asp Gly Gly Phe Ala Gly Leu Asp Asn Tyr Leu Tyr Trp
    50                  55                  60

Leu Thr Gln Arg Cys Met Gly Ser Asp Gly Thr Ile Arg Thr Cys Pro
65                  70                  75                  80

Pro Gly Thr Leu Ala Thr Asp Phe Trp Pro Ala Leu Arg Ile Thr Leu
                85                  90                  95

Phe Phe Thr Val Val Thr Val Gly Leu Glu Thr Ile Leu Gly Thr Ala
            100                 105                 110

Met Ala Leu Ile Met Asn Lys Glu Phe Arg Gly Arg Ala Leu Val Arg
        115                 120                 125

Ala Ala Ile Leu Ile Pro Trp Ala Ile Pro Thr Ala Val Thr Ala Lys
    130                 135                 140

Leu Trp Gln Phe Ile Phe Ala Pro Gln Gly Ile Ile Asn Ser Met Phe
145                 150                 155                 160

Gly Leu Ser Val Ser Trp Thr Thr Asp Pro Trp Ala Ala Arg Ala Ala
```

```
                      165                 170                 175
Val Ile Leu Ala Asp Val Trp Lys Thr Thr Pro Phe Met Ala Leu Leu
            180                 185                 190

Ile Leu Ala Gly Leu Gln Met Ile Pro Lys Glu Thr Tyr Glu Ala Ala
        195                 200                 205

Arg Val Asp Gly Ala Thr Ala Trp Gln Gln Phe Thr Lys Ile Thr Leu
    210                 215                 220

Pro Leu Val Arg Pro Ala Leu Met Val Ala Val Leu Phe Arg Thr Leu
225                 230                 235                 240

Asp Ala Leu Arg Met Tyr Asp Leu Pro Val Ile Met Ile Ser Ser Ser
                245                 250                 255

Ser Asn Ser Pro Thr Ala Val Ile Ser Gln Leu Val Val Glu Asp Met
            260                 265                 270

Arg Gln Asn Asn Phe Asn Ser Ala Ser Ala Leu Ser Thr Leu Ile Phe
        275                 280                 285

Leu Leu Ile Phe Phe Val Ala Phe Ile Met Ile Arg Phe Leu Gly Ala
    290                 295                 300

Asp Val Ser Gly Gln Arg Gly Ile Lys Lys Lys Lys Leu Gly Gly Thr
305                 310                 315                 320

Lys Asp Glu Lys Pro Thr Ala Lys Asp Ala Val Lys Ala Asp Ser
                325                 330                 335

Ala Val Lys Glu Ala Ala Lys Pro
            340

<210> SEQ ID NO 9
<211> LENGTH: 1137
<212> TYPE: DNA
<213> ORGANISM: Corynebacterium glutamicum
<220> FEATURE:
<221> NAME/KEY: CDS
<222> LOCATION: (151)..(987)
<223> OTHER INFORMATION: integral membrane protein (permease) of the ABC
      transporter having the activity of a trehalose importer

<400> SEQUENCE: 9
ggcgttcatc atgatccgat tcctcggcgc agatgtttcg ggccaacgcg gaataaagaa       60
aaagaaactg ggcggaacca aggatgagaa acccaccgct aaggatgctg ttgtaaaggc      120
cgattctgct gtgaaggaag ccgctaagcc atg act aaa cga aca aaa gga ctc      174
                                 Met Thr Lys Arg Thr Lys Gly Leu
                                  1               5 atc ctc aac tac gcc gga gtg gtg ttc atc ctc ttc tgg gga cta gct      222
Ile Leu Asn Tyr Ala Gly Val Val Phe Ile Leu Phe Trp Gly Leu Ala
        10                  15                  20 ccc ttc tac tgg atg gtt atc acc gca ctg cgc gat tcc aag cac acc      270
Pro Phe Tyr Trp Met Val Ile Thr Ala Leu Arg Asp Ser Lys His Thr
 25                  30                  35                  40 ttt gac acc acc cca tgg cca acg cac gtc acc ttg gat aac ttc cgg      318
Phe Asp Thr Thr Pro Trp Pro Thr His Val Thr Leu Asp Asn Phe Arg
                45                  50                  55 gac gca ctg gcc acc gac aaa ggc aac aac ttc ctc gca gcc att ggc      366
Asp Ala Leu Ala Thr Asp Lys Gly Asn Asn Phe Leu Ala Ala Ile Gly
            60                  65                  70 aac tca ctg gtc atc agc gtc acc aca aca gcg atc gct gtt ctc gtg      414
Asn Ser Leu Val Ile Ser Val Thr Thr Thr Ala Ile Ala Val Leu Val
        75                  80                  85 gga gtg ttc acc gcc tac gct cta gcc cga ctg gaa ttc ccg ggc aaa      462
Gly Val Phe Thr Ala Tyr Ala Leu Ala Arg Leu Glu Phe Pro Gly Lys
    90                  95                 100
```

```
ggc att gtc acc ggc atc atc ttg gca gcc tcc atg ttc ccc ggc atc      510
Gly Ile Val Thr Gly Ile Ile Leu Ala Ala Ser Met Phe Pro Gly Ile
105                 110                 115                 120 gcc ctg gtc act ccg ctg ttc cag ctc ttc ggt gac ctc aac tgg atc      558
Ala Leu Val Thr Pro Leu Phe Gln Leu Phe Gly Asp Leu Asn Trp Ile
                125                 130                 135 ggc acc tac caa gcg ctg att atc ccg aac att tcc ttc gcg cta cct      606
Gly Thr Tyr Gln Ala Leu Ile Ile Pro Asn Ile Ser Phe Ala Leu Pro
            140                 145                 150 ctg acg atc tac acg ctc gta tcc ttc ttc agg caa ctg ccc tgg gaa      654
Leu Thr Ile Tyr Thr Leu Val Ser Phe Phe Arg Gln Leu Pro Trp Glu
        155                 160                 165 ctc gaa gaa tca gca cgt gtc gac ggc gcc aca cgt ggc caa gcc ttc      702
Leu Glu Glu Ser Ala Arg Val Asp Gly Ala Thr Arg Gly Gln Ala Phe
    170                 175                 180 cgc atg atc ctg ctt cct cta gca gcg ccc gca cta ttt acc acc gcg      750
Arg Met Ile Leu Leu Pro Leu Ala Ala Pro Ala Leu Phe Thr Thr Ala
185                 190                 195                 200 atc ctc gca ttc att gca acg tgg aac gaa ttc atg ctg gcc cgc caa      798
Ile Leu Ala Phe Ile Ala Thr Trp Asn Glu Phe Met Leu Ala Arg Gln
                205                 210                 215 cta tcc aac acc tcc aca gag cca gtg acc gtt gcg atc gca agg ttc      846
Leu Ser Asn Thr Ser Thr Glu Pro Val Thr Val Ala Ile Ala Arg Phe
            220                 225                 230 acc gga cca agc tcc ttc gaa tac ccc tac gcc tct gtc atg gca gcg      894
Thr Gly Pro Ser Ser Phe Glu Tyr Pro Tyr Ala Ser Val Met Ala Ala
        235                 240                 245 gga gct ttg gtg acc atc cca ctg atc atc atg gtt ctc atc ttc caa      942
Gly Ala Leu Val Thr Ile Pro Leu Ile Ile Met Val Leu Ile Phe Gln
    250                 255                 260 cgc cgc atc gtc tcc gga ctc acc gca ggt ggc gtg aaa gcc tag          987
Arg Arg Ile Val Ser Gly Leu Thr Ala Gly Gly Val Lys Ala
265                 270                 275 actagatact catgagtgct gataaatccc aggaccaatc cgaatcgcaa cgcaaagggc   1047
ttcaacccga agcgctgctt ggattcctgg gattttttctc attcctcgcc gtcatccagg  1107
cagtcatcaa cgtgttacgc cccgaacctg                                    1137

<210> SEQ ID NO 10
<211> LENGTH: 278
<212> TYPE: PRT
<213> ORGANISM: Corynebacterium glutamicum

<400> SEQUENCE: 10

Met Thr Lys Arg Thr Lys Gly Leu Ile Leu Asn Tyr Ala Gly Val Val
1               5                   10                  15

Phe Ile Leu Phe Trp Gly Leu Ala Pro Phe Tyr Trp Met Val Ile Thr
            20                  25                  30

Ala Leu Arg Asp Ser Lys His Thr Phe Asp Thr Thr Pro Trp Pro Thr
        35                  40                  45

His Val Thr Leu Asp Asn Phe Arg Asp Ala Leu Ala Thr Asp Lys Gly
    50                  55                  60

Asn Asn Phe Leu Ala Ala Ile Gly Asn Ser Leu Val Ile Ser Val Thr
65                  70                  75                  80

Thr Thr Ala Ile Ala Val Leu Val Gly Val Phe Thr Ala Tyr Ala Leu
                85                  90                  95

Ala Arg Leu Glu Phe Pro Gly Lys Gly Ile Val Thr Gly Ile Ile Leu
            100                 105                 110
```

```
Ala Ala Ser Met Phe Pro Gly Ile Ala Leu Val Thr Pro Leu Phe Gln
        115                 120                 125

Leu Phe Gly Asp Leu Asn Trp Ile Gly Thr Tyr Gln Ala Leu Ile Ile
130                 135                 140

Pro Asn Ile Ser Phe Ala Leu Pro Leu Thr Ile Tyr Thr Leu Val Ser
145                 150                 155                 160

Phe Phe Arg Gln Leu Pro Trp Glu Leu Glu Ser Ala Arg Val Asp
                165                 170                 175

Gly Ala Thr Arg Gly Gln Ala Phe Arg Met Ile Leu Leu Pro Leu Ala
            180                 185                 190

Ala Pro Ala Leu Phe Thr Thr Ala Ile Leu Ala Phe Ile Ala Thr Trp
        195                 200                 205

Asn Glu Phe Met Leu Ala Arg Gln Leu Ser Asn Thr Ser Thr Glu Pro
    210                 215                 220

Val Thr Val Ala Ile Ala Arg Phe Thr Gly Pro Ser Ser Phe Glu Tyr
225                 230                 235                 240

Pro Tyr Ala Ser Val Met Ala Ala Gly Ala Leu Val Thr Ile Pro Leu
                245                 250                 255

Ile Ile Met Val Leu Ile Phe Gln Arg Arg Ile Val Ser Gly Leu Thr
            260                 265                 270

Ala Gly Gly Val Lys Ala
        275

<210> SEQ ID NO 11
<211> LENGTH: 525
<212> TYPE: DNA
<213> ORGANISM: Corynebacterium glutamicum
<220> FEATURE:
<221> NAME/KEY: CDS
<222> LOCATION: (151)..(375)
<223> OTHER INFORMATION: hypothetical protein

<400> SEQUENCE: 11
cggaccaagc tccttcgaat acccctacgc ctctgtcatg gcagcgggag ctttggtgac      60
catcccactg atcatcatgg ttctcatctt ccaacgccgc atcgtctccg gactcaccgc     120
aggtggcgtg aaagcctaga ctagatactc atg agt gct gat aaa tcc cag gac     174
                                  Met Ser Ala Asp Lys Ser Gln Asp
                                    1               5 caa tcc gaa tcg caa cgc aaa ggg ctt caa ccc gaa gcg ctg ctt gga     222
Gln Ser Glu Ser Gln Arg Lys Gly Leu Gln Pro Glu Ala Leu Leu Gly
    10                  15                  20 ttc ctg gga ttt ttc tca ttc ctc gcc gtc atc cag gca gtc atc aac     270
Phe Leu Gly Phe Phe Ser Phe Leu Ala Val Ile Gln Ala Val Ile Asn
25                  30                  35                  40 gtg tta cgc ccc gaa cct gcc gtg tgg cca gct ctt ctc gcg ctc gtt     318
Val Leu Arg Pro Glu Pro Ala Val Trp Pro Ala Leu Leu Ala Leu Val
                45                  50                  55 tta gta atc gcc aca gtg tca gta tgg agg gct tgg cga aag cgc cgc     366
Leu Val Ile Ala Thr Val Ser Val Trp Arg Ala Trp Arg Lys Arg Arg
            60                  65                  70 cct aat taa agttcctgcg ccaacgccac gataattcca gatggcccgc                415
Pro Asn gcagataaca caatcggtag gtgtcctcgt aatttgcgat cccatctagt ggttccgcac     475
cgatatgttc gatcgtttcc tcaatatcat ccaccgcaaa catcaaacgg                525

<210> SEQ ID NO 12
```

```
<211> LENGTH: 74
<212> TYPE: PRT
<213> ORGANISM: Corynebacterium glutamicum

<400> SEQUENCE: 12

Met Ser Ala Asp Lys Ser Gln Asp Gln Ser Glu Ser Gln Arg Lys Gly
1               5                   10                  15

Leu Gln Pro Glu Ala Leu Leu Gly Phe Leu Gly Phe Phe Ser Phe Leu
                20                  25                  30

Ala Val Ile Gln Ala Val Ile Asn Val Leu Arg Pro Glu Pro Ala Val
            35                  40                  45

Trp Pro Ala Leu Leu Ala Leu Val Leu Val Ile Ala Thr Val Ser Val
50                  55                  60

Trp Arg Ala Trp Arg Lys Arg Arg Pro Asn
65                  70

<210> SEQ ID NO 13
<211> LENGTH: 1305
<212> TYPE: DNA
<213> ORGANISM: Corynebacterium efficiens
<220> FEATURE:
<221> NAME/KEY: CDS
<222> LOCATION: (151)..(1152)
<223> OTHER INFORMATION: ATP-binding and -hydrolyzing (ATPase) protein
      of the ABC transporter having the activity of a trehalose importer

<400> SEQUENCE: 13
```

| | |
|---|---:|
| atggggggtt ccgcggtggt ggttgccggg atggtggata cccagcgtct ggatcagatc | 60 |
| gcgaccgcgg agaaggtcac cgcacgggtc tgagaatgtg ccggcccac aggtacacaa | 120 |

```
ctgggtgtga cactgctaac ttcataggtt atg gcc act gtt tcc ttt gac aaa    174
                                  Met Ala Thr Val Ser Phe Asp Lys
                                  1               5 gtc tcc atc cgg tac ccc ggt gcg gag cgc ccc acc gtc cat gag ctc    222
Val Ser Ile Arg Tyr Pro Gly Ala Glu Arg Pro Thr Val His Glu Leu
    10              15                  20 gac ctc gag ata gcc gac ggt gaa ttc ctc gta ctc gtc ggc ccg tcg    270
Asp Leu Glu Ile Ala Asp Gly Glu Phe Leu Val Leu Val Gly Pro Ser
25              30                  35                  40 ggg tgt gga aaa tca acc acg ctg cga gcg ctc gcc ggg ctc gag gag    318
Gly Cys Gly Lys Ser Thr Thr Leu Arg Ala Leu Ala Gly Leu Glu Glu
                45                  50                  55 gtc gaa tcc ggt gtg atc cgc atc gac ggg cag gat gtc acc agt cag    366
Val Glu Ser Gly Val Ile Arg Ile Asp Gly Gln Asp Val Thr Ser Gln
            60                  65                  70 gaa cct gcg gag cgt gac atc gcg atg gtg ttc cag aac tac gcc ctc    414
Glu Pro Ala Glu Arg Asp Ile Ala Met Val Phe Gln Asn Tyr Ala Leu
        75                  80                  85 tac ccc cac atg tcc gtg gcg cgg aat atg ggt ttc gcc ctc aaa ctg    462
Tyr Pro His Met Ser Val Ala Arg Asn Met Gly Phe Ala Leu Lys Leu
    90                  95                  100 gcc aaa ctg ccc cag gcg gag atc gac gcc aag gtc cgg gag gcc gcc    510
Ala Lys Leu Pro Gln Ala Glu Ile Asp Ala Lys Val Arg Glu Ala Ala
105                 110                 115                 120 gag atc ctc ggc ctc acc gac tac ctg gac cgc aaa ccg aag gac ctc    558
Glu Ile Leu Gly Leu Thr Asp Tyr Leu Asp Arg Lys Pro Lys Asp Leu
                125                 130                 135 tcc ggt ggt cag cgc cag cgt gtg gcc atg ggc cgg gcc ctg gtg cgc    606
Ser Gly Gly Gln Arg Gln Arg Val Ala Met Gly Arg Ala Leu Val Arg
            140                 145                 150 aac ccg aag gtc ttc ctc atg gat gag ccc ctg tcc aac ctc gat gcc    654
Asn Pro Lys Val Phe Leu Met Asp Glu Pro Leu Ser Asn Leu Asp Ala
```

```
                Asn Pro Lys Val Phe Leu Met Asp Glu Pro Leu Ser Asn Leu Asp Ala
                        155                 160                 165 aaa ctg cgt gtg cag acg cgc gcg gaa gtt gcc gca ctg cag cgt cgc              702
Lys Leu Arg Val Gln Thr Arg Ala Glu Val Ala Ala Leu Gln Arg Arg
    170                 175                 180 ctg ggt acc acc acc gtc tat gtc acc cat gat cag gtg gag gcc atg              750
Leu Gly Thr Thr Thr Val Tyr Val Thr His Asp Gln Val Glu Ala Met
185                 190                 195                 200 acg atg ggc gac cgc gtc gcg gtg ctc aag gac gga ctg ctc cag cag              798
Thr Met Gly Asp Arg Val Ala Val Leu Lys Asp Gly Leu Leu Gln Gln
                205                 210                 215 gtg gcc cca ccc cgg gag ctc tac gac acc ccg gtc aat gcg ttc gtc              846
Val Ala Pro Pro Arg Glu Leu Tyr Asp Thr Pro Val Asn Ala Phe Val
            220                 225                 230 gcc ggt ttc atc ggc tcc cca tcg atg aat ctc ttc ccc tac gac ggt              894
Ala Gly Phe Ile Gly Ser Pro Ser Met Asn Leu Phe Pro Tyr Asp Gly
        235                 240                 245 gtg acc ctg ggt gtg cgt ccg gaa tcc atg ctg gtg gtc acc ggc gag              942
Val Thr Leu Gly Val Arg Pro Glu Ser Met Leu Val Val Thr Gly Glu
    250                 255                 260 gcc ccg gcc ggt tac acc gtg gtg gac ggg acg gtg gac atc gtc gag              990
Ala Pro Ala Gly Tyr Thr Val Val Asp Gly Thr Val Asp Ile Val Glu
265                 270                 275                 280 gag ctc ggt tcc gag tcc tat gtt tac gcc acc tgc gac ggc aac cgc             1038
Glu Leu Gly Ser Glu Ser Tyr Val Tyr Ala Thr Cys Asp Gly Asn Arg
                285                 290                 295 ctg gtg gcg cgc tgg gag gac gcc gtg gtg ccc gcg ccg ggt gac cgg             1086
Leu Val Ala Arg Trp Glu Asp Ala Val Val Pro Ala Pro Gly Asp Arg
            300                 305                 310 gtg cgg ttc gcc ttc gac ccg gcg ggt tca cac cgt ttc gac ccg acc             1134
Val Arg Phe Ala Phe Asp Pro Ala Gly Ser His Arg Phe Asp Pro Thr
        315                 320                 325 agc ggt tac cgg ctc agc tgagggtgac cacggtgggg gtcgcggcgt                    1182
Ser Gly Tyr Arg Leu Ser
    330 cgtcaagcac tgccccggc acggggtga tttgaggtaa accggtgcgg gaaagtggcg             1242 aaagtcatta gattgaagtc acctgttgca gagaaaggtg acccaccatg tccaagtttt           1302 ccc                                                                         1305

<210> SEQ ID NO 14
<211> LENGTH: 334
<212> TYPE: PRT
<213> ORGANISM: Corynebacterium efficiens

<400> SEQUENCE: 14

Met Ala Thr Val Ser Phe Asp Lys Val Ser Ile Arg Tyr Pro Gly Ala
1               5                   10                  15

Glu Arg Pro Thr Val His Glu Leu Asp Leu Glu Ile Ala Asp Gly Glu
                20                  25                  30

Phe Leu Val Leu Val Gly Pro Ser Gly Cys Gly Lys Ser Thr Thr Leu
            35                  40                  45

Arg Ala Leu Ala Gly Leu Glu Glu Val Glu Ser Gly Val Ile Arg Ile
        50                  55                  60

Asp Gly Gln Asp Val Thr Ser Gln Glu Pro Ala Glu Arg Asp Ile Ala
65                  70                  75                  80

Met Val Phe Gln Asn Tyr Ala Leu Tyr Pro His Met Ser Val Ala Arg
                85                  90                  95
```

```
Asn Met Gly Phe Ala Leu Lys Leu Ala Lys Leu Pro Gln Ala Glu Ile
            100                 105                 110

Asp Ala Lys Val Arg Glu Ala Glu Ile Leu Gly Leu Thr Asp Tyr
        115                 120                 125

Leu Asp Arg Lys Pro Lys Asp Leu Ser Gly Gln Arg Gln Arg Val
    130                 135                 140

Ala Met Gly Arg Ala Leu Val Arg Asn Pro Lys Val Phe Leu Met Asp
145                 150                 155                 160

Glu Pro Leu Ser Asn Leu Asp Ala Lys Leu Arg Val Gln Thr Arg Ala
                165                 170                 175

Glu Val Ala Ala Leu Gln Arg Arg Leu Gly Thr Thr Thr Val Tyr Val
            180                 185                 190

Thr His Asp Gln Val Glu Ala Met Thr Met Gly Asp Arg Val Ala Val
        195                 200                 205

Leu Lys Asp Gly Leu Leu Gln Gln Val Ala Pro Arg Glu Leu Tyr
    210                 215                 220

Asp Thr Pro Val Asn Ala Phe Val Ala Gly Phe Ile Gly Ser Pro Ser
225                 230                 235                 240

Met Asn Leu Phe Pro Tyr Asp Gly Val Thr Leu Gly Val Arg Pro Glu
                245                 250                 255

Ser Met Leu Val Val Thr Gly Glu Ala Pro Ala Gly Tyr Thr Val Val
            260                 265                 270

Asp Gly Thr Val Asp Ile Val Glu Glu Leu Gly Ser Glu Ser Tyr Val
        275                 280                 285

Tyr Ala Thr Cys Asp Gly Asn Arg Leu Val Ala Arg Trp Glu Asp Ala
    290                 295                 300

Val Val Pro Ala Pro Gly Asp Arg Val Arg Phe Ala Phe Asp Pro Ala
305                 310                 315                 320

Gly Ser His Arg Phe Asp Pro Thr Ser Gly Tyr Arg Leu Ser
                325                 330

<210> SEQ ID NO 15
<211> LENGTH: 1605
<212> TYPE: DNA
<213> ORGANISM: Corynebacterium efficiens
<220> FEATURE:
<221> NAME/KEY: CDS
<222> LOCATION: (151)..(1455)
<223> OTHER INFORMATION: periplasmic (or lipoprotein) substrate-binding
      protein of the ABC transporter having the activity of a trehalose
      importer

<400> SEQUENCE: 15
ttaccggctc agctgagggt gaccacggtg ggggtcgcgg cgtcgtcaag cactgccccc        60
ggcacggggg tgatttgagg taaaccggtg cgggaaagtg gcgaaagtca ttagattgaa       120
gtcacctgtt gcagagaaag gtgacccacc atg tcc aag ttt tcc cgc aag acc       174
                                  Met Ser Lys Phe Ser Arg Lys Thr
                                    1               5 ggc gta tcg ctg gcc gca acc agc ctg atc gcc gcc atc gcc ctg gcc       222
Gly Val Ser Leu Ala Ala Thr Ser Leu Ile Ala Ala Ile Ala Leu Ala
     10                  15                  20 ggt tgt ggc aat gac acc gcc gac gat gcc ggc acg acc gac acc agc       270
Gly Cys Gly Asn Asp Thr Ala Asp Asp Ala Gly Thr Thr Asp Thr Ser
 25                  30                  35                  40 acc aat gac acc gaa gcc acc acc gcc gcc tcg ggt gag gag ggc cgc       318
Thr Asn Asp Thr Glu Ala Thr Thr Ala Ala Ser Gly Glu Glu Gly Arg
                 45                  50                  55
```

```
ggc ccg att acc ttc gcc atg ggc aag aac gac acc gac aag atc att     366
Gly Pro Ile Thr Phe Ala Met Gly Lys Asn Asp Thr Asp Lys Ile Ile
         60                  65                  70 ccc gtg atc gag aag tgg aac gag gag aac ccc gac cag gag gtg acc     414
Pro Val Ile Glu Lys Trp Asn Glu Glu Asn Pro Asp Gln Glu Val Thr
     75                  80                  85 ctc aac gaa ctc gcc ggt gag gcc gac gcc cag cgc gag acc ctc gtg     462
Leu Asn Glu Leu Ala Gly Glu Ala Asp Ala Gln Arg Glu Thr Leu Val
 90                  95                 100 cag tcc ctc cag gcc ggc aac tcc gat tat gac gtc atg gcc ctc gat     510
Gln Ser Leu Gln Ala Gly Asn Ser Asp Tyr Asp Val Met Ala Leu Asp
105                 110                 115                 120 gtc atc tgg acc gcc gac ttc gcc gcc aac cag tgg ctc gcg ccg ctt     558
Val Ile Trp Thr Ala Asp Phe Ala Ala Asn Gln Trp Leu Ala Pro Leu
             125                 130                 135 gag ggg gaa ctc gag gtc gac acc tcc ggg ctg ctt gag gcc acc gtg     606
Glu Gly Glu Leu Glu Val Asp Thr Ser Gly Leu Leu Glu Ala Thr Val
         140                 145                 150 gaa tcc gcc aca tac atg gac acc ctc tac gca ctg ccg cag aac acc     654
Glu Ser Ala Thr Tyr Met Asp Thr Leu Tyr Ala Leu Pro Gln Asn Thr
     155                 160                 165 aac ggc cag ctg ctc tac cgc aac acc gag atc atc ccc gag gcc ccg     702
Asn Gly Gln Leu Leu Tyr Arg Asn Thr Glu Ile Ile Pro Glu Ala Pro
170                 175                 180 gag aac tgg gct gac ctc gtc gaa tcc tgc acc ctg gcg gag gag gcc     750
Glu Asn Trp Ala Asp Leu Val Glu Ser Cys Thr Leu Ala Glu Glu Ala
185                 190                 195                 200 gag gtt gac tgc ctg acc acc cag ctc aag cag tac gag ggc ctg acc     798
Glu Val Asp Cys Leu Thr Thr Gln Leu Lys Gln Tyr Glu Gly Leu Thr
             205                 210                 215 gtc aac acc atc ggc ttc atg gag ggc tgg ggc ggt tcc gtc ctg gac     846
Val Asn Thr Ile Gly Phe Met Glu Gly Trp Gly Gly Ser Val Leu Asp
         220                 225                 230 gat gac ggc acc acc gtg gtc gtc gac tcc gac gag tcg aag gag ggc     894
Asp Asp Gly Thr Thr Val Val Val Asp Ser Asp Glu Ser Lys Glu Gly
         235                 240                 245 ctg cag gcg ctt gtc gac gcc tac gag gac ggc acc atc tcg tcc gcg     942
Leu Gln Ala Leu Val Asp Ala Tyr Glu Asp Gly Thr Ile Ser Ser Ala
250                 255                 260 tcc acc gca gcc acc gag gag gag acc aac ctg gcc ttc acc gcc ggt     990
Ser Thr Ala Ala Thr Glu Glu Glu Thr Asn Leu Ala Phe Thr Ala Gly
265                 270                 275                 280 gag acc gcc tac gcc atc aac tgg ccg tac atg tac acc aac gcc gag    1038
Glu Thr Ala Tyr Ala Ile Asn Trp Pro Tyr Met Tyr Thr Asn Ala Glu
             285                 290                 295 gac tcc gag gcc acc gcc ggc aag ttc gag gtc cag cca ctc gtg ggc    1086
Asp Ser Glu Ala Thr Ala Gly Lys Phe Glu Val Gln Pro Leu Val Gly
         300                 305                 310 aag gac ggc gtg ggt gtg tcc acc ctc ggt ggc tac aac aac gcc atc    1134
Lys Asp Gly Val Gly Val Ser Thr Leu Gly Gly Tyr Asn Asn Ala Ile
         315                 320                 325 aac atc aac tcg gag aac aag gca acc gcc cgc gac ttc atc gag ttc    1182
Asn Ile Asn Ser Glu Asn Lys Ala Thr Ala Arg Asp Phe Ile Glu Phe
330                 335                 340 atc atc aac gag gag aac cag acc tgg ttc gcc gac aac tcc ttc cca    1230
Ile Ile Asn Glu Glu Asn Gln Thr Trp Phe Ala Asp Asn Ser Phe Pro
345                 350                 355                 360 ccg gtg ctc gcc tcc atc tac gac gat gag gaa ctg atc gag cag tac    1278
Pro Val Leu Ala Ser Ile Tyr Asp Asp Glu Glu Leu Ile Glu Gln Tyr
             365                 370                 375
```

```
cca tac ctg ccc gcg ctg aag gaa tcc ctg gag aac gcg gca ccg cgt    1326
Pro Tyr Leu Pro Ala Leu Lys Glu Ser Leu Glu Asn Ala Ala Pro Arg
            380                 385                 390 ccg gtc tcc ccg ttc tac acc gcc atc tcc aag gcc atc cag gac aac    1374
Pro Val Ser Pro Phe Tyr Thr Ala Ile Ser Lys Ala Ile Gln Asp Asn
        395                 400                 405 gcc tac gca gcc atc aac ggc aac gtc gac gtc gac cag gcc acc gct    1422
Ala Tyr Ala Ala Ile Asn Gly Asn Val Asp Val Asp Gln Ala Thr Ala
    410                 415                 420 gac atg aag gca gca atc gag aac gcc tcc tag agcgacaggg acaccccac   1475
Asp Met Lys Ala Ala Ile Glu Asn Ala Ser
425                 430 cccatgacac tccggtcacc caccaggtga ccggggtttt gtcatagtct gggcgggaac  1535
aggtgttgtc acccaactgc tttcccagtg tcggatcacg tgtctgctca agtgtcggat  1595
ccaacgtccc                                                         1605

<210> SEQ ID NO 16
<211> LENGTH: 434
<212> TYPE: PRT
<213> ORGANISM: Corynebacterium efficiens

<400> SEQUENCE: 16

Met Ser Lys Phe Ser Arg Lys Thr Gly Val Ser Leu Ala Ala Thr Ser
1               5                   10                  15

Leu Ile Ala Ala Ile Ala Leu Ala Gly Cys Gly Asn Asp Thr Ala Asp
            20                  25                  30

Asp Ala Gly Thr Thr Asp Thr Ser Thr Asn Asp Thr Glu Ala Thr Thr
        35                  40                  45

Ala Ala Ser Gly Glu Glu Gly Arg Gly Pro Ile Thr Phe Ala Met Gly
    50                  55                  60

Lys Asn Asp Thr Asp Lys Ile Ile Pro Val Ile Glu Lys Trp Asn Glu
65                  70                  75                  80

Glu Asn Pro Asp Gln Glu Val Thr Leu Asn Glu Leu Ala Gly Glu Ala
                85                  90                  95

Asp Ala Gln Arg Glu Thr Leu Val Gln Ser Leu Gln Ala Gly Asn Ser
            100                 105                 110

Asp Tyr Asp Val Met Ala Leu Asp Val Ile Trp Thr Ala Asp Phe Ala
        115                 120                 125

Ala Asn Gln Trp Leu Ala Pro Leu Glu Gly Glu Leu Glu Val Asp Thr
    130                 135                 140

Ser Gly Leu Leu Glu Ala Thr Val Glu Ser Ala Thr Tyr Met Asp Thr
145                 150                 155                 160

Leu Tyr Ala Leu Pro Gln Asn Thr Asn Gly Gln Leu Leu Tyr Arg Asn
                165                 170                 175

Thr Glu Ile Ile Pro Glu Ala Pro Glu Asn Trp Ala Asp Leu Val Glu
            180                 185                 190

Ser Cys Thr Leu Ala Glu Glu Ala Val Asp Cys Leu Thr Thr Gln
        195                 200                 205

Leu Lys Gln Tyr Glu Gly Leu Thr Val Asn Thr Ile Gly Phe Met Glu
    210                 215                 220

Gly Trp Gly Gly Ser Val Leu Asp Asp Gly Thr Thr Val Val Val
225                 230                 235                 240

Asp Ser Asp Glu Ser Lys Glu Gly Leu Gln Ala Leu Val Asp Ala Tyr
                245                 250                 255
```

```
Glu Asp Gly Thr Ile Ser Ser Ala Ser Thr Ala Ala Thr Glu Glu
            260                 265                 270

Thr Asn Leu Ala Phe Thr Ala Gly Glu Thr Ala Tyr Ala Ile Asn Trp
            275                 280                 285

Pro Tyr Met Tyr Thr Asn Ala Glu Asp Ser Glu Ala Thr Ala Gly Lys
290                 295                 300

Phe Glu Val Gln Pro Leu Val Gly Lys Asp Gly Val Gly Val Ser Thr
305                 310                 315                 320

Leu Gly Gly Tyr Asn Asn Ala Ile Asn Ile Asn Ser Glu Asn Lys Ala
                325                 330                 335

Thr Ala Arg Asp Phe Ile Glu Phe Ile Ile Asn Glu Glu Asn Gln Thr
            340                 345                 350

Trp Phe Ala Asp Asn Ser Phe Pro Pro Val Leu Ala Ser Ile Tyr Asp
            355                 360                 365

Asp Glu Glu Leu Ile Glu Gln Tyr Pro Tyr Leu Pro Ala Leu Lys Glu
        370                 375                 380

Ser Leu Glu Asn Ala Ala Pro Arg Pro Val Ser Pro Phe Tyr Thr Ala
385                 390                 395                 400

Ile Ser Lys Ala Ile Gln Asp Asn Ala Tyr Ala Ala Ile Asn Gly Asn
                405                 410                 415

Val Asp Val Asp Gln Ala Thr Ala Asp Met Lys Ala Ala Ile Glu Asn
            420                 425                 430

Ala Ser
```

```
<210> SEQ ID NO 17
<211> LENGTH: 786
<212> TYPE: DNA
<213> ORGANISM: Corynebacterium efficiens
<220> FEATURE:
<221> NAME/KEY: CDS
<222> LOCATION: (151)..(636)
<223> OTHER INFORMATION: function unknown

<400> SEQUENCE: 17
cccccacccc atgacactcc ggtcacccac caggtgaccg gggttttgtc atagtctggg      60
cgggaacagg tgttgtcacc caactgcttt cccagtgtcg gatcacgtgt ctgctcaagt     120
gtcggatcca acgtccctga ggaggacccc atg tca cac cag cgc tcc ccc gag     174
                                  Met Ser His Gln Arg Ser Pro Glu
                                    1               5 aca ccc gag atg ctg tcc tac acc atc tcc gga ttc atc tcc cgg tgc     222
Thr Pro Glu Met Leu Ser Tyr Thr Ile Ser Gly Phe Ile Ser Arg Cys
 10                  15                  20 ccc gtc cag gtc tat gag gcc atc gtc gat cac cgt caa ctc tcc cga     270
Pro Val Gln Val Tyr Glu Ala Ile Val Asp His Arg Gln Leu Ser Arg
 25                  30                  35                  40 cat ttc gcc acc ggc ggg gca cag ggc agg atg agc gcc ggc gcg acg     318
His Phe Ala Thr Gly Gly Ala Gln Gly Arg Met Ser Ala Gly Ala Thr
                 45                  50                  55 gtg acc tgg gac ttc gac gat ggg tcc ggc ccc tgc acc gtc gag gtc     366
Val Thr Trp Asp Phe Asp Asp Gly Ser Gly Pro Cys Thr Val Glu Val
             60                  65                  70 ctc cag gcg gcg cat tcc cgg tgt ctg atc ctg gag tgg tcc agc ccc     414
Leu Gln Ala Ala His Ser Arg Cys Leu Ile Leu Glu Trp Ser Ser Pro
         75                  80                  85 gat gcg ggt gaa ccc gcc ggg agc acc acg gtg gag ttc gcc ttc gaa     462
Asp Ala Gly Glu Pro Ala Gly Ser Thr Thr Val Glu Phe Ala Phe Glu
     90                  95                 100
```

```
ccc gcc aat gac ttc acc cgc acc aaa ctg acc atc acg gaa tca ggg      510
Pro Ala Asn Asp Phe Thr Arg Thr Lys Leu Thr Ile Thr Glu Ser Gly
105                 110                 115                 120 tgg cct ccc acc acc gcc ggc acc agg aaa gcg ctg cgc gaa tgc cac      558
Trp Pro Pro Thr Thr Ala Gly Thr Arg Lys Ala Leu Arg Glu Cys His
            125                 130                 135 cgg tgg acc acc atg ctc acc ggt ctg aag gcc tgg ttg gaa cac ggg      606
Arg Trp Thr Thr Met Leu Thr Gly Leu Lys Ala Trp Leu Glu His Gly
                140                 145                 150 gtg gtc ctc ggc agg gat cta cat cgc tag ggagccttgt taaccggagg        656
Val Val Leu Gly Arg Asp Leu His Arg
            155                 160 tagagggtgg aacggaggtg gggttactgt tccctcactg acaccagggt tctatgatcc    716
aagtaacact tttcctgatt tctcttcttt tcccatccat ccctctacc ccaaggagca     776 ctggtgacat                                                           786

<210> SEQ ID NO 18
<211> LENGTH: 161
<212> TYPE: PRT
<213> ORGANISM: Corynebacterium efficiens

<400> SEQUENCE: 18

Met Ser His Gln Arg Ser Pro Glu Thr Pro Glu Met Leu Ser Tyr Thr
1               5                   10                  15

Ile Ser Gly Phe Ile Ser Arg Cys Pro Val Gln Val Tyr Glu Ala Ile
            20                  25                  30

Val Asp His Arg Gln Leu Ser Arg His Phe Ala Thr Gly Gly Ala Gln
        35                  40                  45

Gly Arg Met Ser Ala Gly Ala Thr Val Thr Trp Asp Phe Asp Asp Gly
    50                  55                  60

Ser Gly Pro Cys Thr Val Glu Val Leu Gln Ala Ala His Ser Arg Cys
65                  70                  75                  80

Leu Ile Leu Glu Trp Ser Ser Pro Asp Ala Gly Glu Pro Ala Gly Ser
                85                  90                  95

Thr Thr Val Glu Phe Ala Phe Glu Pro Ala Asn Asp Phe Thr Arg Thr
            100                 105                 110

Lys Leu Thr Ile Thr Glu Ser Gly Trp Pro Pro Thr Thr Ala Gly Thr
        115                 120                 125

Arg Lys Ala Leu Arg Glu Cys His Arg Trp Thr Thr Met Leu Thr Gly
    130                 135                 140

Leu Lys Ala Trp Leu Glu His Gly Val Val Leu Gly Arg Asp Leu His
145                 150                 155                 160

Arg

<210> SEQ ID NO 19
<211> LENGTH: 1347
<212> TYPE: DNA
<213> ORGANISM: Corynebacterium efficiens
<220> FEATURE:
<221> NAME/KEY: CDS
<222> LOCATION: (151)..(1197)
<223> OTHER INFORMATION: integral membrane protein (permease) of the ABC
      transporter having the activity of a trehalose importer

<400> SEQUENCE: 19
agggagcctt gttaaccgga ggtagagggt ggaacggagg tggggttact gttccctcac     60
tgacaccagg gttctatgat ccaagtaaca cttttcctga tttctcttct tttcccatcc    120
```

```
atccctctca ccccaaggag cactggtgac atg gcc aag atg aaa cag gcg cga      174
                                 Met Ala Lys Met Lys Gln Ala Arg
                                  1               5 tca gcc gca tgg ttg atc gcg cca gcc atg att gtc ctg acg gtg gtg      222
Ser Ala Ala Trp Leu Ile Ala Pro Ala Met Ile Val Leu Thr Val Val
 10              15                  20 atc ggc tac ccc atc gtc cgt gcc gtc tgg ttg tcc ttc cag gcg gac      270
Ile Gly Tyr Pro Ile Val Arg Ala Val Trp Leu Ser Phe Gln Ala Asp
 25              30                  35                  40 aag ggt ctc gat ccc acc acc ggg ttg ttc acc gac ggt ggt ttc gcc      318
Lys Gly Leu Asp Pro Thr Thr Gly Leu Phe Thr Asp Gly Gly Phe Ala
             45                  50                  55 ggt ttc gac aat tac ctg tac tgg ctc acc caa cgc tgc atg tcc ccc      366
Gly Phe Asp Asn Tyr Leu Tyr Trp Leu Thr Gln Arg Cys Met Ser Pro
                 60                  65                  70 gac ggc acc gtg ggt acc tgt ccg ccc ggt acc ctg gcc acc gac ttc      414
Asp Gly Thr Val Gly Thr Cys Pro Pro Gly Thr Leu Ala Thr Asp Phe
     75                  80                  85 tgg ccg gcc ctg cgc atc acc ctg ttc ttc acc gtg gtc acc gtc acc      462
Trp Pro Ala Leu Arg Ile Thr Leu Phe Phe Thr Val Val Thr Val Thr
 90                  95                 100 ctg gag acc atc ctg ggt atg gtc atg gcc ctg atc atg agc aag gag      510
Leu Glu Thr Ile Leu Gly Met Val Met Ala Leu Ile Met Ser Lys Glu
105                 110                 115                 120 ttc cgc ggc cgg gcc ctc gtc cgc gcc gcg gtc ctg atc ccg tgg gcg      558
Phe Arg Gly Arg Ala Leu Val Arg Ala Ala Val Leu Ile Pro Trp Ala
                    125                 130                 135 atc ccg acg gcg gtc acc gcg aag ctg tgg cag ttc ctg ttc gcc cca      606
Ile Pro Thr Ala Val Thr Ala Lys Leu Trp Gln Phe Leu Phe Ala Pro
                140                 145                 150 cgg ggc atc atc aat gaa ctc ttc gga ctc aat atc agc tgg acc acc      654
Arg Gly Ile Ile Asn Glu Leu Phe Gly Leu Asn Ile Ser Trp Thr Thr
            155                 160                 165 gat ccg tgg gcg gca cgc gcc gcg gtc atc ctc gcc gat gtc tgg aag      702
Asp Pro Trp Ala Ala Arg Ala Ala Val Ile Leu Ala Asp Val Trp Lys
170                 175                 180 acc acc ccg ttc atg gcg ctg ctc atc ctc gcc ggg ctg cag atg atc      750
Thr Thr Pro Phe Met Ala Leu Leu Ile Leu Ala Gly Leu Gln Met Ile
185                 190                 195                 200 ccc aag ggc acc tat gag gcc gcc cgt gtg gac ggg gcc agc gcc tgg      798
Pro Lys Gly Thr Tyr Glu Ala Ala Arg Val Asp Gly Ala Ser Ala Trp
                    205                 210                 215 cag cag ttc acc agg atc acc ctc ccc ctg gtc aaa ccg gcc ctg atg      846
Gln Gln Phe Thr Arg Ile Thr Leu Pro Leu Val Lys Pro Ala Leu Met
                220                 225                 230 gtc gcg gtg ctg ttc cgc acc ctg gat gcc ctg cgc atg tac gac ctg      894
Val Ala Val Leu Phe Arg Thr Leu Asp Ala Leu Arg Met Tyr Asp Leu
            235                 240                 245 ccg gtg atc atg atc tcc gcc tcc tcg aac tcc ccc acc gcc gtg atc      942
Pro Val Ile Met Ile Ser Ala Ser Ser Asn Ser Pro Thr Ala Val Ile
250                 255                 260 tcc cag ctg gtg gtc gag gac atg cgt cag aac aac ttc aac tcg gcc      990
Ser Gln Leu Val Val Glu Asp Met Arg Gln Asn Asn Phe Asn Ser Ala
265                 270                 275                 280 tcc gcg ctg tcg acg ttg atc ttc ctg ctc atc ttc ttc gtg gcc ttc     1038
Ser Ala Leu Ser Thr Leu Ile Phe Leu Leu Ile Phe Phe Val Ala Phe
                    285                 290                 295 gtc atg atc cgg ttc ctc ggg gcg gat gtt tcc ggg cag cgc gga acg     1086
Val Met Ile Arg Phe Leu Gly Ala Asp Val Ser Gly Gln Arg Gly Thr
                300                 305                 310
```

```
gag aag aac agg cgg cgg tgg cgc agg ccc ggc cgg aag ggc gcg gct    1134
Glu Lys Asn Arg Arg Arg Trp Arg Arg Pro Gly Arg Lys Gly Ala Ala
            315                 320                 325 gtt gcc ggg gca ggc gtc ggc atc acc ggt gcc gcg gtg gca agt gag    1182
Val Ala Gly Ala Gly Val Gly Ile Thr Gly Ala Ala Val Ala Ser Glu
        330                 335                 340 gtg gca tca tca tga aacgcaagac caagaaccta atcctcaact acgcaggcgt    1237
Val Ala Ser Ser
345 ggtgttcatc ctgttctggg ggctggcgcc gttctactgg atggtggtca ctgcactgcg    1297 ggattcccgc cacaccttcg acaccacccc ctggcccacg cacgtgaccc              1347

<210> SEQ ID NO 20
<211> LENGTH: 348
<212> TYPE: PRT
<213> ORGANISM: Corynebacterium efficiens

<400> SEQUENCE: 20

Met Ala Lys Met Lys Gln Ala Arg Ser Ala Ala Trp Leu Ile Ala Pro
1               5                   10                  15

Ala Met Ile Val Leu Thr Val Val Ile Gly Tyr Pro Ile Val Arg Ala
            20                  25                  30

Val Trp Leu Ser Phe Gln Ala Asp Lys Gly Leu Asp Pro Thr Thr Gly
        35                  40                  45

Leu Phe Thr Asp Gly Gly Phe Ala Gly Phe Asp Asn Tyr Leu Tyr Trp
    50                  55                  60

Leu Thr Gln Arg Cys Met Ser Pro Asp Gly Val Gly Thr Cys Pro
65                  70                  75                  80

Pro Gly Thr Leu Ala Thr Asp Phe Trp Pro Ala Leu Arg Ile Thr Leu
                85                  90                  95

Phe Phe Thr Val Val Thr Val Thr Leu Glu Thr Ile Leu Gly Met Val
            100                 105                 110

Met Ala Leu Ile Met Ser Lys Glu Phe Arg Gly Arg Ala Leu Val Arg
        115                 120                 125

Ala Ala Val Leu Ile Pro Trp Ala Ile Pro Thr Ala Val Thr Ala Lys
    130                 135                 140

Leu Trp Gln Phe Leu Phe Ala Pro Arg Gly Ile Ile Asn Glu Leu Phe
145                 150                 155                 160

Gly Leu Asn Ile Ser Trp Thr Thr Asp Pro Trp Ala Arg Ala Ala
                165                 170                 175

Val Ile Leu Ala Asp Val Trp Lys Thr Thr Pro Phe Met Ala Leu Leu
            180                 185                 190

Ile Leu Ala Gly Leu Gln Met Ile Pro Lys Gly Thr Tyr Glu Ala Ala
        195                 200                 205

Arg Val Asp Gly Ala Ser Ala Trp Gln Gln Phe Thr Arg Ile Thr Leu
    210                 215                 220

Pro Leu Val Lys Pro Ala Leu Met Val Ala Leu Phe Arg Thr Leu
225                 230                 235                 240

Asp Ala Leu Arg Met Tyr Asp Leu Pro Val Ile Met Ile Ser Ala Ser
                245                 250                 255

Ser Asn Ser Pro Thr Ala Val Ile Ser Gln Leu Val Val Glu Asp Met
            260                 265                 270

Arg Gln Asn Asn Phe Asn Ser Ala Ser Ala Leu Ser Thr Leu Ile Phe
        275                 280                 285
```

```
Leu Leu Ile Phe Phe Val Ala Phe Val Met Ile Arg Phe Leu Gly Ala
    290                 295                 300

Asp Val Ser Gly Gln Arg Gly Thr Glu Lys Asn Arg Arg Trp Arg
305                 310                 315                 320

Arg Pro Gly Arg Lys Gly Ala Ala Val Ala Gly Ala Gly Val Gly Ile
                    325                 330                 335

Thr Gly Ala Ala Val Ala Ser Glu Val Ala Ser Ser
            340                 345

<210> SEQ ID NO 21
<211> LENGTH: 1137
<212> TYPE: DNA
<213> ORGANISM: Corynebacterium efficiens
<220> FEATURE:
<221> NAME/KEY: CDS
<222> LOCATION: (151)..(987)
<223> OTHER INFORMATION: integral membrane protein (permease) of the ABC
      transporter having the activity of a trehalose importer

<400> SEQUENCE: 21
```

| | |
|---|---|
| gatccggttc ctcggggcgg atgtttccgg gcagcgcgga acggagaaga acaggcggcg | 60 |
| gtggcgcagg cccggccgga agggcgcggc tgttgccggg gcaggcgtcg gcatcaccgg | 120 |

```
tgccgcggtg gcaagtgagg tggcatcatc atg aaa cgc aag acc aag aac cta        174
                                   Met Lys Arg Lys Thr Lys Asn Leu
                                   1               5 atc ctc aac tac gca ggc gtg gtg ttc atc ctg ttc tgg ggg ctg gcg        222
Ile Leu Asn Tyr Ala Gly Val Val Phe Ile Leu Phe Trp Gly Leu Ala
    10                  15                  20 ccg ttc tac tgg atg gtg gtc act gca ctg cgg gat tcc cgc cac acc        270
Pro Phe Tyr Trp Met Val Val Thr Ala Leu Arg Asp Ser Arg His Thr
25                  30                  35                  40 ttc gac acc acc ccc tgg ccc acg cac gtg acc ctg cag aac ttc cgg        318
Phe Asp Thr Thr Pro Trp Pro Thr His Val Thr Leu Gln Asn Phe Arg
                45                  50                  55 gat gcg ctg gcc acc gac aag ggc aac aac ttc ctg gcg gcg atc ggc        366
Asp Ala Leu Ala Thr Asp Lys Gly Asn Asn Phe Leu Ala Ala Ile Gly
        60                  65                  70 aac tcg ctg atc gtc agt ctc acc acc acc gcc ctc gcg gtg atc gtg        414
Asn Ser Leu Ile Val Ser Leu Thr Thr Thr Ala Leu Ala Val Ile Val
    75                  80                  85 ggc gtg ttc acc gcc tat gcg ctg gca cgc ctg gac ttc ccc ggt aag        462
Gly Val Phe Thr Ala Tyr Ala Leu Ala Arg Leu Asp Phe Pro Gly Lys
90                  95                  100 ggg atc atc acc ggc atc atc ctg gcg gcc tcg atg ttc ccg ggt atc        510
Gly Ile Ile Thr Gly Ile Ile Leu Ala Ala Ser Met Phe Pro Gly Ile
105                 110                 115                 120 gcc ctg gtg acc ccg ctg ttc cag ctg ttc ggc aac atc ggc tgg atc        558
Ala Leu Val Thr Pro Leu Phe Gln Leu Phe Gly Asn Ile Gly Trp Ile
                125                 130                 135 ggc acc tac cag gcg ctg atc atc ccg aac atc tcc ttc gcc ctg ccg        606
Gly Thr Tyr Gln Ala Leu Ile Ile Pro Asn Ile Ser Phe Ala Leu Pro
        140                 145                 150 ctg acc atc tac acc ctg gtg tcc ttc ttc cgc cag ctg ccg tgg gag        654
Leu Thr Ile Tyr Thr Leu Val Ser Phe Phe Arg Gln Leu Pro Trp Glu
    155                 160                 165 ctc gag gag gcc gcc cgt gtg gac ggc gcg acc cgg ggg cag gcc ttc        702
Leu Glu Glu Ala Ala Arg Val Asp Gly Ala Thr Arg Gly Gln Ala Phe
170                 175                 180 cgc aag atc ctg tta ccc ctg gcc gcc ccg gcg ctg ttc acc acc gcg        750
Arg Lys Ile Leu Leu Pro Leu Ala Ala Pro Ala Leu Phe Thr Thr Ala
```

```
                                                                                   -continued 185                 190                 195                 200
atc ctg gcg ttc atc gcc tcg tgg aat gag ttc atg ctg gcc cgt cag          798
Ile Leu Ala Phe Ile Ala Ser Trp Asn Glu Phe Met Leu Ala Arg Gln
                            205                 210                 215 ctg tcc acc acc gcc acc gaa ccg gtc acc gtg gcc atc gcc cgc ttc          846
Leu Ser Thr Thr Ala Thr Glu Pro Val Thr Val Ala Ile Ala Arg Phe
            220                 225                 230 tcc ggg ccg agt tcc ttc gag tac ccg tat gcc tcg gtg atg gca gcc          894
Ser Gly Pro Ser Ser Phe Glu Tyr Pro Tyr Ala Ser Val Met Ala Ala
            235                 240                 245 ggt gcc ctg gtc acc gtc cca ctg atc atc atg gtg ctc atc ttc cag          942
Gly Ala Leu Val Thr Val Pro Leu Ile Ile Met Val Leu Ile Phe Gln
            250                 255                 260 cga cgc atc gtc tcc ggc ctg acc gcg ggt ggt gtg aag gcc tag              987
Arg Arg Ile Val Ser Gly Leu Thr Ala Gly Gly Val Lys Ala
265                 270                 275 actgtcggtc atgagcacga acgaacccag ggaccagtcc gaacacaaac gccgagccct       1047
ccagctcgat gcattcatcg ggttcctggg gttcttcgcc ttcctgtcgg tgatccaggc       1107
cgtgatcaat gtgctccagc ccgaaccgaa                                        1137

<210> SEQ ID NO 22
<211> LENGTH: 278
<212> TYPE: PRT
<213> ORGANISM: Corynebacterium efficiens

<400> SEQUENCE: 22

Met Lys Arg Lys Thr Lys Asn Leu Ile Leu Asn Tyr Ala Gly Val Val
1               5                   10                  15

Phe Ile Leu Phe Trp Gly Leu Ala Pro Phe Tyr Trp Met Val Val Thr
            20                  25                  30

Ala Leu Arg Asp Ser Arg His Thr Phe Asp Thr Thr Pro Trp Pro Thr
            35                  40                  45

His Val Thr Leu Gln Asn Phe Arg Asp Ala Leu Ala Thr Asp Lys Gly
        50                  55                  60

Asn Asn Phe Leu Ala Ala Ile Gly Asn Ser Leu Ile Val Ser Leu Thr
65                  70                  75                  80

Thr Thr Ala Leu Ala Val Ile Val Gly Val Phe Thr Ala Tyr Ala Leu
                85                  90                  95

Ala Arg Leu Asp Phe Pro Gly Lys Gly Ile Ile Thr Gly Ile Ile Leu
            100                 105                 110

Ala Ala Ser Met Phe Pro Gly Ile Ala Leu Val Thr Pro Leu Phe Gln
            115                 120                 125

Leu Phe Gly Asn Ile Gly Trp Ile Gly Thr Tyr Gln Ala Leu Ile Ile
        130                 135                 140

Pro Asn Ile Ser Phe Ala Leu Pro Leu Thr Ile Tyr Thr Leu Val Ser
145                 150                 155                 160

Phe Phe Arg Gln Leu Pro Trp Glu Leu Glu Ala Ala Arg Val Asp
                165                 170                 175

Gly Ala Thr Arg Gly Gln Ala Phe Arg Lys Ile Leu Leu Pro Leu Ala
            180                 185                 190

Ala Pro Ala Leu Phe Thr Thr Ala Ile Leu Ala Phe Ile Ala Ser Trp
            195                 200                 205

Asn Glu Phe Met Leu Ala Arg Gln Leu Ser Thr Thr Ala Thr Glu Pro
        210                 215                 220

Val Thr Val Ala Ile Ala Arg Phe Ser Gly Pro Ser Ser Phe Glu Tyr
```

```
                   225                 230                 235                 240
        Pro Tyr Ala Ser Val Met Ala Ala Gly Ala Leu Val Thr Val Pro Leu
                            245                 250                 255

Ile Ile Met Val Leu Ile Phe Gln Arg Arg Ile Val Ser Gly Leu Thr
                    260                 265                 270

Ala Gly Gly Val Lys Ala
                275

<210> SEQ ID NO 23
<211> LENGTH: 534
<212> TYPE: DNA
<213> ORGANISM: Corynebacterium efficiens
<220> FEATURE:
<221> NAME/KEY: CDS
<222> LOCATION: (151)..(384)
<223> OTHER INFORMATION: hyopthetical protein

<400> SEQUENCE: 23
ccgggccgag ttccttcgag tacccgtatg cctcggtgat ggcagccggt gccctggtca        60
ccgtcccact gatcatcatg gtgctcatct tccagcgacg catcgtctcc ggcctgaccg       120
cgggtggtgt gaaggcctag actgtcggtc atg agc acg aac gaa ccc agg gac       174
                                  Met Ser Thr Asn Glu Pro Arg Asp
                                    1               5 cag tcc gaa cac aaa cgc cga gcc ctc cag ctc gat gca ttc atc ggg        222
Gln Ser Glu His Lys Arg Arg Ala Leu Gln Leu Asp Ala Phe Ile Gly
        10                  15                  20 ttc ctg ggg ttc ttc gcc ttc ctg tcg gtg atc cag gcc gtg atc aat        270
Phe Leu Gly Phe Phe Ala Phe Leu Ser Val Ile Gln Ala Val Ile Asn
25                  30                  35                  40 gtg ctc cag ccc gaa ccg aag gtc tgg ccg gca ctg ctg gcc ctg ctg        318
Val Leu Gln Pro Glu Pro Lys Val Trp Pro Ala Leu Leu Ala Leu Leu
                45                  50                  55 ctg gtg ctg gcg acg gtg agc ctg tgg cgg gcc cgg cgc gac cga tct        366
Leu Val Leu Ala Thr Val Ser Leu Trp Arg Ala Arg Arg Asp Arg Ser
            60                  65                  70 ccc cgg acg ggg gct taa gcacccatgg ccatcgtcta caacgccgcc                414
Pro Arg Thr Gly Ala
        75 accacggtca acggctttct cgcagatgac cgtgattccc tgcagtggct cttcgacgtc       474 cccggatccg ccgagacgga agcggatatc accacattcc tcgatagcgt cggcgctgta       534

<210> SEQ ID NO 24
<211> LENGTH: 77
<212> TYPE: PRT
<213> ORGANISM: Corynebacterium efficiens

<400> SEQUENCE: 24

Met Ser Thr Asn Glu Pro Arg Asp Gln Ser Glu His Lys Arg Arg Ala
1               5                   10                  15

Leu Gln Leu Asp Ala Phe Ile Gly Phe Leu Gly Phe Phe Ala Phe Leu
            20                  25                  30

Ser Val Ile Gln Ala Val Ile Asn Val Leu Gln Pro Glu Pro Lys Val
        35                  40                  45

Trp Pro Ala Leu Leu Ala Leu Leu Val Leu Ala Thr Val Ser Leu
    50                  55                  60

Trp Arg Ala Arg Arg Asp Arg Ser Pro Arg Thr Gly Ala
65                  70                  75
```

<210> SEQ ID NO 25
<211> LENGTH: 6199
<212> TYPE: DNA
<213> ORGANISM: Corynebacterium glutamicum

<400> SEQUENCE: 25

| | | | | | |
|---|---|---|---|---|---|
| gaaaattgtc | ggcgcgatca | ttccggcgct | ggcgtgaagt | gcgatttggt | acagctgata | 60 |
| cgcgatgaaa | gccagcagca | atcatccacg | ggtatgccca | cagtttgttt | tcaggactgc | 120 |
| gaccaggagt | accactttcg | caaggccgtg | cgtcagtaga | tatctagcgc | tgaacaacgt | 180 |
| agcgtggctg | gtgagtgatt | cactgctgtg | cccaaggaac | gtggcgatgc | cattgtcggg | 240 |
| atcttcattc | agttcgtttt | gggtgagcag | aacggtccag | tggtgaaggc | tttcgggatc | 300 |
| gacaagaagg | aggagcactc | cgccgatgag | ctcaaataag | ccgttgagtc | ctttgagctt | 360 |
| gatgccgccc | caaagagtt | gttgccaccg | atcgcgaact | ttggcagtag | ccatgcgttc | 420 |
| tgctcctgac | cttgaacagc | ggtcccaatt | tagacccgct | aaacccacaa | tgtgtactgg | 480 |
| tgctggtaat | ttagtagaac | atggcaacgg | tcacattcga | caaggtcaca | atccggtacc | 540 |
| ccggcgcgga | gcgcgcaaca | gttcatgagc | ttgatttaga | tatcgctgat | ggcgagtttt | 600 |
| tggtgctcgt | cggcccttcg | ggttgtggta | aatccactac | gctgcgtgct | ttggcggggc | 660 |
| ttgagggcgt | ggagtcgggt | gtgatcaaaa | ttgatggcaa | ggatgtcact | ggtcaggagc | 720 |
| cggcggatcg | cgatatcgcg | atggtgttcc | agaattatgc | tctgtacccct | cacatgacgg | 780 |
| tggcgaagaa | tatgggtttt | gcgctgaagt | tggctaagct | gccgcaggcg | cagatcgatg | 840 |
| cgaaggtcaa | tgaggctgcg | gaaattcttg | ggttgacgga | gtttttggat | cgcaagccta | 900 |
| aggatttatc | gggtggtcag | cgtcagcgtg | tggcgatggg | tcgcgcgttg | gtgcgtgatc | 960 |
| cgaaggtgtt | cctcatggat | gagccgctgt | ccaacctgga | tgcgaaattg | cgcgtgcaaa | 1020 |
| cccgcgcgga | ggtcgctgct | ttgcagcgtc | gcctgggcac | caccacggtg | tatgtcaccc | 1080 |
| acgatcaggt | tgaggcaatg | acgatgggcg | atcgggttgc | ggtgctcaag | gacgggttgc | 1140 |
| tgcagcaggt | cgcaccgccc | agggagcttt | acgacgcccc | ggtcaacgaa | ttcgttgcgg | 1200 |
| gcttcatcgg | ctcgccgtcc | atgaacctct | ccctgccaa | cgggcacaag | atgggtgtgc | 1260 |
| gcccggagaa | gatgctggtc | aatgagaccc | ctgagggttt | cacaagcatt | gatgctgtgg | 1320 |
| tggatatcgt | cgaggagctt | ggctccgaat | cgtatgttta | tgccacttgg | gagggccacc | 1380 |
| gcctggtggc | ccgttgggtg | gaaggccccg | tgccagcccc | tggcacgcct | gtgacttttt | 1440 |
| cctatgatgc | ggcgcaggcg | catcatttcg | atctggagtc | gggcgagcgt | atcgcttagt | 1500 |
| ttcggacgtg | gggaggcgtc | gaaaagcatc | tttattttg | accctccggg | ggtgatttaa | 1560 |
| cctaaaattc | cacacaaacg | tgttcgaggt | cattagattg | ataagcatct | gttgttaaga | 1620 |
| aaggtgactt | cctatgtcct | cgatttcccg | caagaccggc | gcgtcacttg | cagccaccac | 1680 |
| actgttggca | gcgatcgcac | tggccggttg | tagttcagac | tcaagctccg | actccacaga | 1740 |
| ttccaccgct | agcgaaggcg | cagacagccg | cggcccatc | accttgcga | tgggcaaaaa | 1800 |
| cgacaccgac | aaagtcattc | cgatcatcga | ccgctggaac | gaagcccacc | ccgatgagca | 1860 |
| ggtaacgctc | aacgaactcg | ccggtgaagc | cgacgcgcag | cgcgaaaccc | tcgtgcaatc | 1920 |
| cctgcaggcc | ggcaactctg | actacgacgt | catggcgctc | gacgtcatct | ggaccgcaga | 1980 |
| cttcgcggca | aaccaatggc | tcgcaccact | tgaaggcgac | ctcgaggtag | acacctccgg | 2040 |
| actgctgcaa | tccaccgtgg | attccgcaac | ctacaacggc | accctctacg | cactgccaca | 2100 |
| gaacaccaac | ggccagctac | tgttccgcaa | caccgaaatc | atcccagaag | caccagcaaa | 2160 |

```
ctgggctgac ctcgtggaat cctgcacgct tgctgaagaa gcaggcgttg attgcctgac    2220
cactcagctc aagcagtacg aaggcctttc agtgaacacc atcggcttca tcgaaggttg    2280
gggaggcagc gtcctagacg atgacggcaa cgtcaccgta gacagcgacg acgccaaggc    2340
aggccttcaa gcgcttgtcg acggcttcga cgacggcacc atctccaagg catcccttgc    2400
agcgaccgaa gaagaaacca acctcgcatt caccgaaggc caaaccgcct acgccattaa    2460
ctggccatac atgtacacca actccgaaga agccgaagca accgcaggca aattcgaagt    2520
acagcccctc gtaggtaaag acggcgtcgg cgtatccacc cttggtggct acaacaacgg    2580
catcaacgtc aactccgaaa acaaggcaac cgcccgcgac ttcatcgaat tcatcatcaa    2640
cgaagagaac caaacctggt tcgcggacaa ctccttccca ccagttctgg catccatcta    2700
cgatgatgag tcccttgttg agcagtaccc atacctgcca gcactgaagg aatccctgga    2760
aaacgcagca ccacgcccag tgtctccttt ctacccagcc atctccaagg caatccagga    2820
caacgcctac gcagcgctta acggcaacgt cgacgttgac caggcaacca ccgatatgaa    2880
ggcagcgatc gaaaacgctt ccagctagtt cggtaattta gttcattctc cggccacctt    2940
ccctgaaatc cttagcggat ttccacaaag gtggccggag ttttgtccta ttgttgggtg    3000
taattgaact tgtgtgaaag gagtccggat ggcttccggc aaagatcttc aagtttccac    3060
atttggctac atctcccgct gccccgtgca ggtctacgaa gcaatcgcag atcccagaca    3120
actagaacgc tacttcgcca ccggcggagt atctggccgc ctcgaaaccg gatcgactgt    3180
ctattgggac ttcgttgatt ttcccggtgc gtttccggtc caagttgtct cagctacaca    3240
ggctgaacac attgaactcc gctggggaca agcaaatgag ctgcgttccg tcaacttcga    3300
gttcgaacct tttagaaatt tcacccgcac gaaactcacc atcaccgaag gcagttggcc    3360
gctcactccc gcaggagccc aagaggctct gggcagccag atgggatgga ctggcatgct    3420
gtccgcacta aaagcgtggc tggaatacgg agtgaacctc cgcgacgggt tttataagca    3480
ataggcaatg tgtccatcac gatgtgtggc ggattatgat ccatgtaaca agaatgtgca    3540
gtttcacaga actgacaatc aacttatttt gacctgacaa aaggagcgac gacacatggc    3600
cacattcaaa caggccagaa gcgctgcctg gctgatcgcc cccgccctcg tggtccttgc    3660
agtggtgatc ggatatccca tcgtccgagc aatttggcta tccttccagg ccgacaaagg    3720
cctcgacccc accaccggac tcttcaccga cggtggcttc gcaggactag acaattacct    3780
ctactggctc acccaacgat gcatgggttc agacggcacc atccgtacct gcccacccgg    3840
cacactagcc accgacttct ggccagcact acgcatcacg ttgttcttca ccgtggttac    3900
cgtcggcttg gaaactatcc tcggcaccgc catggcactg atcatgaaca agaattccg    3960 tggccgcgca cttgttcgcg cagcgattct tatcccttgg gcaatcccca ccgccgtcac    4020
cgcaaaactg tggcagttca tcttcgcacc acaaggcatc atcaactcca tgtttggact    4080
tagtgtcagt tggaccaccg atccgtgggc agctagagcc gccgtcattc ttgccgacgt    4140
ctggaaaacc acaccattca tggcactgct gatcctcgcc ggtctgcaaa tgatcccgaa    4200
ggaaacctac gaagcagccc gcgtcgatgg cgcaaccgcg tggcagcaat tcaccaagat    4260
caccctcccg ctggtgcgcc cagctttgat ggtggcagta ctcttccgca ccctcgatgc    4320
gctacgcatg tatgacctcc ccgtcatcat gatctccagc tcctccaact cccccaccgc    4380
tgttatctcc cagctggttg tggaagacat gcgccaaaac aacttcaact ccgcttccgc    4440
cctttccaca ctgatcttcc tgctgatctt cttcgtggcg ttcatcatga tccgattcct    4500
cggcgcagat gtttcgggcc aacgcggaat aaagaaaaag aaactgggcg gaaccaagga    4560
```

```
tgagaaaccc accgctaagg atgctgttgt aaaggccgat tctgctgtga aggaagccgc    4620
taagccatga ctaaacgaac aaaaggactc atcctcaact acgccggagt ggtgttcatc    4680
ctcttctggg gactagctcc cttctactgg atggttatca ccgcactgcg cgattccaag    4740
cacacctttg acaccacccc atggccaacg cacgtcacct tggataactt ccgggacgca    4800
ctggccaccg acaaaggcaa caacttcctc gcagccattg caactcact ggtcatcagc     4860
gtcaccacaa cagcgatcgc tgttctcgtg ggagtgttca ccgcctacgc tctagcccga    4920
ctggaattcc cgggcaaagg cattgtcacc ggcatcatct tggcagcctc catgttcccc    4980
ggcatcgccc tggtcactcc gctgttccag ctcttcggtg acctcaactg gatcggcacc    5040
taccaagcgc tgattatccc gaacatttcc ttcgcgctac ctctgacgat ctacacgctc    5100
gtatccttct tcaggcaact gccctgggaa ctcgaagaat cagcacgtgt cgacggcgcc    5160
acacgtggcc aagccttccg catgatcctg cttcctctag cagcgcccgc actatttacc    5220
accgcgatcc tcgcattcat tgcaacgtgg aacgaattca tgctggcccg ccaactatcc    5280
aacacctcca cagagccagt gaccgttgcg atcgcaaggt tcaccggacc aagctccttc    5340
gaatacccct acgcctctgt catggcagcg ggagctttgg tgaccatccc actgatcatc    5400
atggttctca tcttccaacg ccgcatcgtc tccggactca ccgcaggtgg cgtgaaagcc    5460
tagactagat actcatgagt gctgataaat cccaggacca atccgaatcg caacgcaaag    5520
ggcttcaacc cgaagcgctg cttggattcc tgggattttt ctcattcctc gccgtcatcc    5580
aggcagtcat caacgtgtta cgccccgaac ctgccgtgtg gccagctctt ctcgcgctcg    5640
ttttagtaat cgccacagtg tcagtatgga gggcttggcg aaagcgccgc cctaattaaa    5700
gttcctgcgc caacgccacg ataattccag atggcccgcg cagataacac aatcggtagg    5760
tgtcctcgta atttgcgatc ccatctagtg gttccgcacc gatatgttcg atcgtttcct    5820
caatatcatc caccgcaaac atcaaacggt gcatcccaat ctggttaggt gcagatggag    5880
cggttgcaat cggttccggt tgtagatatt gagtaagctc cacccgagaa tgtccatccg    5940
gagttttcag caccgcgatc tcagatcgaa ttccgctgag accaacggtc cgatcagcaa    6000
aatcccctg gaccattgtt cggccatcta gggacatccc taatttctca aagaaaccga    6060
ctgcttcatc caacgattcc accacaatcg ccacgttgtc caaacgttta attcccatga    6120
tccccatcgt aggtagcatc gtgtgatggc gatcatctac aacacatcga gcacgctcaa    6180
cggcttcatc gcagacaaa                                                  6199
```

<210> SEQ ID NO 26
<211> LENGTH: 1701
<212> TYPE: DNA
<213> ORGANISM: Corynebacterium glutamicum
<220> FEATURE:
<221> NAME/KEY: misc_feature
<222> LOCATION: (1)..(6)
<223> OTHER INFORMATION: XbaI cleavage site
<220> FEATURE:
<221> NAME/KEY: misc_feature
<222> LOCATION: (7)..(606)
<223> OTHER INFORMATION: upstream flanking region
<220> FEATURE:
<221> NAME/KEY: promoter
<222> LOCATION: (607)..(1095)
<223> OTHER INFORMATION: Pgap promoter
<220> FEATURE:
<221> NAME/KEY: misc_feature
<222> LOCATION: (607)..(612)
<223> OTHER INFORMATION: ScaI cleavage site
<220> FEATURE:

```
<221> NAME/KEY: mutation
<222> LOCATION: (1079)..(1079)
<223> OTHER INFORMATION: replacement of nucleobase thymine (T) with
      guanine (G)
<220> FEATURE:
<221> NAME/KEY: mutation
<222> LOCATION: (1080)..(1080)
<223> OTHER INFORMATION: replacement of nucleobase thymine (T) with
      cytosine (C)
<220> FEATURE:
<221> NAME/KEY: mutation
<222> LOCATION: (1081)..(1081)
<223> OTHER INFORMATION: replacement of nucleobase thymine (T) with
      guanine (G)
<220> FEATURE:
<221> NAME/KEY: CDS
<222> LOCATION: (1096)..(1695)
<223> OTHER INFORMATION: cg0832
<220> FEATURE:
<221> NAME/KEY: misc_feature
<222> LOCATION: (1096)..(1695)
<223> OTHER INFORMATION: downstream flanking region
<220> FEATURE:
<221> NAME/KEY: misc_feature
<222> LOCATION: (1696)..(1701)
<223> OTHER INFORMATION: HindIII cleavage site

<400> SEQUENCE: 26
tctagagggt gtaattgaac ttgtgtgaaa ggagtccgga tggcttccgg caaagatctt      60
caagtttcca catttggcta catctcccgc tgccccgtgc aggtctacga agcaatcgca     120
gatcccagac aactagaacg ctacttcgcc accggcggag tatctggccg cctcgaaacc     180
ggatcgactg tctattggga cttcgttgat tttcccggtg cgtttccggt ccaagttgtc     240
tcagctacac aggctgaaca cattgaactc cgctggggac aagcaaatga gctgcgttcc     300
gtcaacttcg agttcgaacc ttttagaaat ttcacccgca cgaaactcac catcaccgaa     360
ggcagttggc cgctcactcc cgcaggagcc caagaggctc tgggcagcca gatgggatgg     420
actggcatgc tgtccgcact aaaagcgtgg ctggaatacg gagtgaacct ccgcgacggg     480
ttttataagc aataggcaat gtgtccatca cgatgtgtgg cggattatga tccatgtaac     540
aagaatgtgc agtttcacag aactgacaat caacttattt tgacctgaca aaaggagcga     600
cgacacagta cttgaagcct aaaaacgacc gagcctattg ggattaccat tgaagccagt     660
gtgagttgca tcacattggc ttcaaatctg agactttaat ttgtggattc acggggtgt      720 aatgtagttc ataattaacc ccattcgggg gagcagatcg tagtgcgaac gatttcaggt     780
tcgttccctg caaaaactat ttagcgcaag tgttggaaat gccccgtttt ggggtcaatg     840 tccattttg aatgtgtctg tatgattttg catctgctgc gaaatctttg tttccccgct      900
aaagttgagg acaggttgac acggagttga ctcgacgaat tatccaatgt gagtaggttt     960
ggtgcgtgag ttgaaaaat cgccatact cgcccttggg ttctgtcagc tcaagaattc     1020
ttgagtgacc gatgctctga ttgacctaac tgcttgacac attgcatttc ctacaatcgc    1080
gagaggagac acaac atg gcc aca ttc aaa cag gcc aga agc gct gcc tgg     1131
                  Met Ala Thr Phe Lys Gln Ala Arg Ser Ala Ala Trp
                   1               5                  10 ctg atc gcc ccc gcc ctc gtg gtc ctt gca gtg gtg atc gga tat ccc        1179
Leu Ile Ala Pro Ala Leu Val Val Leu Ala Val Val Ile Gly Tyr Pro
        15                  20                  25 atc gtc cga gca att tgg cta tcc ttc cag gcc gac aaa ggc ctc gac        1227
Ile Val Arg Ala Ile Trp Leu Ser Phe Gln Ala Asp Lys Gly Leu Asp
 30                  35                  40 ccc acc acc gga ctc ttc acc gac ggt ggc ttc gca gga cta gac aat        1275
Pro Thr Thr Gly Leu Phe Thr Asp Gly Gly Phe Ala Gly Leu Asp Asn
```

```
                    45                  50                  55                  60
tac ctc tac tgg ctc acc caa cga tgc atg ggt tca gac ggc acc atc       1323
Tyr Leu Tyr Trp Leu Thr Gln Arg Cys Met Gly Ser Asp Gly Thr Ile
                    65                  70                  75 cgt acc tgc cca ccc ggc aca cta gcc acc gac ttc tgg cca gca cta       1371
Arg Thr Cys Pro Pro Gly Thr Leu Ala Thr Asp Phe Trp Pro Ala Leu
                80                  85                  90 cgc atc acg ttg ttc ttc acc gtg gtt acc gtc ggc ttg gaa act atc       1419
Arg Ile Thr Leu Phe Phe Thr Val Val Thr Val Gly Leu Glu Thr Ile
            95                 100                 105 ctc ggc acc gcc atg gca ctg atc atg aac aaa gaa ttc cgt ggc cgc       1467
Leu Gly Thr Ala Met Ala Leu Ile Met Asn Lys Glu Phe Arg Gly Arg
        110                 115                 120 gca ctt gtt cgc gca gcg att ctt atc cct tgg gca atc ccc acc gcc       1515
Ala Leu Val Arg Ala Ala Ile Leu Ile Pro Trp Ala Ile Pro Thr Ala
125                 130                 135                 140 gtc acc gca aaa ctg tgg cag ttc atc ttc gca cca caa ggc atc atc       1563
Val Thr Ala Lys Leu Trp Gln Phe Ile Phe Ala Pro Gln Gly Ile Ile
                145                 150                 155 aac tcc atg ttt gga ctt agt gtc agt tgg acc acc gat ccg tgg gca       1611
Asn Ser Met Phe Gly Leu Ser Val Ser Trp Thr Thr Asp Pro Trp Ala
                160                 165                 170 gct aga gcc gcc gtc att ctt gcc gac gtc tgg aaa acc aca cca ttc       1659
Ala Arg Ala Ala Val Ile Leu Ala Asp Val Trp Lys Thr Thr Pro Phe
            175                 180                 185 atg gca ctg ctg atc ctc gcc ggt ctg caa atg atc aagctt              1701
Met Ala Leu Leu Ile Leu Ala Gly Leu Gln Met Ile
        190                 195                 200

<210> SEQ ID NO 27
<211> LENGTH: 200
<212> TYPE: PRT
<213> ORGANISM: Corynebacterium glutamicum

<400> SEQUENCE: 27

Met Ala Thr Phe Lys Gln Ala Arg Ser Ala Ala Trp Leu Ile Ala Pro
1               5                   10                  15

Ala Leu Val Val Leu Ala Val Val Ile Gly Tyr Pro Ile Val Arg Ala
                20                  25                  30

Ile Trp Leu Ser Phe Gln Ala Asp Lys Gly Leu Asp Pro Thr Thr Gly
            35                  40                  45

Leu Phe Thr Asp Gly Gly Phe Ala Gly Leu Asp Asn Tyr Leu Tyr Trp
        50                  55                  60

Leu Thr Gln Arg Cys Met Gly Ser Asp Gly Thr Ile Arg Thr Cys Pro
65                  70                  75                  80

Pro Gly Thr Leu Ala Thr Asp Phe Trp Pro Ala Leu Arg Ile Thr Leu
                85                  90                  95

Phe Phe Thr Val Val Thr Val Gly Leu Glu Thr Ile Leu Gly Thr Ala
            100                 105                 110

Met Ala Leu Ile Met Asn Lys Glu Phe Arg Gly Arg Ala Leu Val Arg
        115                 120                 125

Ala Ala Ile Leu Ile Pro Trp Ala Ile Pro Thr Ala Val Thr Ala Lys
    130                 135                 140

Leu Trp Gln Phe Ile Phe Ala Pro Gln Gly Ile Ile Asn Ser Met Phe
145                 150                 155                 160

Gly Leu Ser Val Ser Trp Thr Thr Asp Pro Trp Ala Ala Arg Ala Ala
                165                 170                 175
```

```
Val Ile Leu Ala Asp Val Trp Lys Thr Thr Pro Phe Met Ala Leu Leu
            180                 185                 190

Ile Leu Ala Gly Leu Gln Met Ile
        195                 200

<210> SEQ ID NO 28
<211> LENGTH: 20
<212> TYPE: DNA
<213> ORGANISM: artificial sequence
<220> FEATURE:
<223> OTHER INFORMATION: primer
<220> FEATURE:
<221> NAME/KEY: primer
<222> LOCATION: (1)..(20)
<223> OTHER INFORMATION: cg0832_1.p

<400> SEQUENCE: 28
gctggaatac ggagtgaacc                                                   20

<210> SEQ ID NO 29
<211> LENGTH: 20
<212> TYPE: DNA
<213> ORGANISM: artificial sequence
<220> FEATURE:
<223> OTHER INFORMATION: primer
<220> FEATURE:
<221> NAME/KEY: primer
<222> LOCATION: (1)..(20)
<223> OTHER INFORMATION: cg0832_2.p

<400> SEQUENCE: 29
gggattgccc aagggataag                                                   20

<210> SEQ ID NO 30
<211> LENGTH: 28
<212> TYPE: DNA
<213> ORGANISM: artificial
<220> FEATURE:
<223> OTHER INFORMATION: synthetic DNA

<400> SEQUENCE: 30
gctctagatg cgttctgctc ctgacctt                                          28

<210> SEQ ID NO 31
<211> LENGTH: 28
<212> TYPE: DNA
<213> ORGANISM: artificial
<220> FEATURE:
<223> OTHER INFORMATION: synthetic DNA

<400> SEQUENCE: 31
cgggatcctt tgcgttgcga ttcggatt                                          28
```

MICROORGANISM AND METHOD FOR THE FERMENTATIVE PRODUCTION OF AN ORGANIC-CHEMICAL COMPOUND

CROSS REFERENCE TO RELATED APPLICATIONS

The present application claims the benefit of U.S. provisional application 61/533,783 filed on Sep. 12, 2011 and priority to German Application, DE 10 2011 006 716.7 filed on Apr. 4, 2011.

FIELD OF THE INVENTION

The invention relates to a microorganism which produces and/or secretes an organic-chemical compound, said microorganism having increased expression of a trehalose importer, and to a method of producing an organic-chemical compound by using the microorganism according to the invention.

BACKGROUND OF THE INVENTION

L-Amino acids are used in human medicine, in the pharmaceutical industry, in the food industry and very particularly in animal nutrition. It is known that L-amino acids such as, for example, L-lysine, are produced by fermentation of strains of coryneform bacteria, in particular *Corynebacterium glutamicum*, or of strains of the Enterobacteriaceae family, in particular *Escherichia coli*. Because of the great economic importance, work is continually being done on improving the production methods. Method improvements may relate to fermentation technology measures such as, for example, stirring and supplying oxygen, or to the composition of the nutrient media, for example the sugar concentration during fermentation, or to the working-up to product form by, for example, ion exchange chromatography or to the intrinsic performance properties of the microorganism itself.

The methods used for improving the performance properties of these microorganisms are those of mutagenesis, selection and choice of mutants. The strains obtained in this way are resistant to anti-metabolites or are auxotrophic for metabolites of regulatory importance, and produce L-amino acids. A known anti-metabolite is the lysine analogue S-(2-aminoethyl)-L-cysteine (AEC).

Methods of recombinant DNA technology have likewise been used for some years for strain improvement of L-amino acid-producing strains of the genus *Corynebacterium*, in particular *Corynebacterium glutamicum*, or of the genus *Escherichia*, in particular *Escherichia coli*, by modifying, i.e. enhancing or attenuating, individual amino acid biosynthesis genes and investigating the effect on amino acid production.

The nucleotide sequences of the chromosomes of numerous bacteria have been disclosed. The nucleotide sequence of the *Corynebacterium glutamicum* ATCC13032 genome is described in Ikeda and Nakagawa (*Applied Microbiology and Biotechnology* 62:99-109 (2003)), in EP 1 108 790 and in Kalinowski et al. (*J. Biotechnol.* 104(1-3), (2003)). The nucleotide sequence of the *Corynebacterium glutamicum* R genome is described in Yukawa et al. (*Microbiology* 153(4): 1042-1058 (2007)). The nucleotide sequence of the *Corynebacterium efficiens* genome is described in Nishio et al. (*Genome Research* 13(7):1572-1579 (2003)). The nucleotide sequence of the *Corynebacterium diphteriae* NCTC 13129 genome has been described by Cerdeno-Tarraga et al. (*Nucl. Ac. Res.* 31 (22):6516-6523 (2003)). The nucleotide sequence of the *Corynebacterium jeikeum* genome has been described by Tauch et al. (*J. Bacteriol.* 187(13):4671-4682 (2005)).

A review of various aspects of the fermentative production of L-amino acids can be found in R. Faurie and J. Thommel in *Advances in Biochemical Engineering Biotechnology*, volume 79 (Springer-Verlag, Berlin, Heidelberg Germany (2003)).

Significant amounts of secreted trehalose are found in the supernatant of industrial fermentations of *C. glutamicum*. This externally accumulated trehalose is not metabolically recycled by the cells. Said externally accumulated trehalose therefore represents a significant loss in industrial fermentations, both in respect of maximally achievable product formation and with regard to the biomass concentration reached in the fermenter.

Making use of the externally accumulated trehalose is the main goal desired. Achieving this goal would have a plurality of possible positive consequences: (1) utilization of substrate carbon which otherwise remains unused at the end of the fermentation, (2) increase in the biomass achievable in the fermentation, (3) increased product yield in biotechnological production processes, e.g. in amino acid production, (4) avoidance of unwanted contamination in the product supernatant at the end of the fermentation.

SUMMARY OF THE INVENTION

The present invention provides a microorganism which produces and/or secretes an organic-chemical compound. The microorganism has increased expression, compared to the particular starting strain, of one or more protein subunits of the ABC transporter having the activity of a trehalose importer, and is capable of taking up trehalose from the medium.

The invention furthermore provides a method for the fermentative production of an organic-chemical compound, comprising the steps:
a) culturing the above-described microorganism according to the present invention in a suitable medium, resulting in a fermentation broth, and
b) accumulating the organic-chemical compound in the fermentation broth of a);
wherein accumulation of trehalose in the fermentation broth is reduced or avoided.

Preference is given to reducing the accumulation of trehalose in the fermentation broth by 50% or more, by 70% or more, by 80% or more, by 90% or more, by 95% or more, by 98% or more, by 99% or more, and most preferably by 99.5% or more, compared to the particular starting strain of the microorganism.

The present invention is advantageous in that (1) substrate carbon in the form of trehalose which otherwise remains unused in the fermentation broth at the end of the fermentation is utilized; (2) the biomass achievable in the fermentation is increased; (3) the product yield in biotechnological production processes, e.g. amino acid production, is increased and (4) unwanted contamination in the product supernatant at the end of the fermentation is avoided.

Surprisingly, a trehalose uptake system has been identified for *C. glutamicum*. Enhanced expression of all genes of the operon encoding the trehalose import system result in an increase in the target product (the organic-chemical compound) with the use of a corresponding producer strain. Surprisingly, a corresponding trehalose uptake has also been found when only one of the subunits (e.g. permease subunit) is expressed. The present invention thus provides microorganisms (producer strains) whose cells take up the externally accumulated trehalose through an active transport system in the plasma membrane. The fact that *C. glutamicum* has the metabolic capacity of metabolizing trehalose in the cytoplasm gives rise to the above advantages of the present invention. Preferably, the microorganism is capable of reducing, compared to the particular starting strain of the microorganism, or, in particular, of avoiding, accumulation of trehalose in the medium (culturing medium).

In a preferred embodiment of the microorganism, the ABC transporter having the activity of a trehalose importer is derived from *Corynebacterium glutamicum*. The protein subunits of the ABC transporter having the activity of a trehalose importer are as follows: integral membrane protein (permease), ATP-binding and—hydrolyzing (ATPase) protein and periplasmic (or lipoprotein) substrate-binding protein. The composition of an ABC transporter is as follows: two permeases, two ATPases and one periplasmic (or lipoprotein) substrate-binding protein. The two permeases and the ATPases may in each case have different amino acid sequences.

A preferred embodiment of the microorganism according to the present invention has increased expression, compared to the particular starting strain, of all protein subunits of the ABC transporter having the activity of a trehalose importer. This means that preferentially the permease, the ATPase and the periplasmic subunit of the ABC transporter having the activity of a trehalose importer have increased expression, i.e. are overexpressed.

In an alternative embodiment, the microorganism according to the present invention has increased expression, compared to the particular starting strain, of one or more protein subunits of the ABC transporter having the activity of a trehalose importer. Moreover, a gene of the operon coding for the subunits of the ABC transporter having the activity of a trehalose importer, which (gene) does not necessarily code for a subunit of the ABC transporter itself, may have increased expression.

Preference is furthermore given to a microorganism having, compared to the particular starting strain, increased expression of at least one polynucleotide selected from the group consisting of a) to f):
 a) a polynucleotide coding for a polypeptide with an amino acid sequence that is at least 70% identical to the amino acid sequence depicted in SEQ ID NO:2 or 14;
 b) a polynucleotide coding for a polypeptide with an amino acid sequence that is at least 70% identical to the amino acid sequence depicted in SEQ ID NO:4 or 16;
 c) a polynucleotide coding for a polypeptide with an amino acid sequence that is at least 70% identical to the amino acid sequence depicted in SEQ ID NO:6 or 18;
 d) a polynucleotide coding for a polypeptide with an amino acid sequence that is at least 70% identical to the amino acid sequence depicted in SEQ ID NO:8 or 20;
 e) a polynucleotide coding for a polypeptide with an amino acid sequence that is at least 70% identical to the amino acid sequence depicted in SEQ ID NO:10 or 22;
 f) a polynucleotide coding for a polypeptide with an amino acid sequence that is at least 70% identical to the amino acid sequence depicted in SEQ ID NO:12 or 24.

Preference is furthermore given to the microorganism having, compared to the particular starting strain, increased expression of at least one polynucleotide selected from the group consisting of a), b), d), e):
 a) a polynucleotide coding for a polypeptide with an amino acid sequence that is at least 70% identical to the amino acid sequence depicted in SEQ ID NO:2 or 14;
 b) a polynucleotide coding for a polypeptide with an amino acid sequence that is at least 70% identical to the amino acid sequence depicted in SEQ ID NO:4 or 16;
 d) a polynucleotide coding for a polypeptide with an amino acid sequence that is at least 70% identical to the amino acid sequence depicted in SEQ ID NO:8 or 20;
 e) a polynucleotide coding for a polypeptide with an amino acid sequence that is at least 70% identical to the amino acid sequence depicted in SEQ ID NO:10 or 22.

In a further preferred embodiment, the microorganism has, compared to the particular starting strain, increased expression of at least one polynucleotide selected from the group consisting of b), d) and e):
 b) a polynucleotide coding for a polypeptide with an amino acid sequence that is at least 70% identical to the amino acid sequence depicted in SEQ ID NO:4 or 16;
 d) a polynucleotide coding for a polypeptide with an amino acid sequence that is at least 70% identical to the amino acid sequence depicted in SEQ ID NO:8 or 20;
 e) a polynucleotide coding for a polypeptide with an amino acid sequence that is at least 70% identical to the amino acid sequence depicted in SEQ ID NO:10 or 22.

Particularly preferably, the microorganism has, compared to the particular starting strain, increased expression of the following polynucleotides:
 d) a polynucleotide coding for a polypeptide with an amino acid sequence that is at least 70% identical to the amino acid sequence depicted in SEQ ID NO:8 or 20; and/or
 e) a polynucleotide coding for a polypeptide with an amino acid sequence that is at least 70% identical to the amino acid sequence depicted in SEQ ID NO:10 or 22.

A further, preferred embodiment of the microorganism has, compared to the particular starting strain, increased expression of the polynucleotides a) and b):
 a) a polynucleotide coding for a polypeptide with an amino acid sequence that is at least 70% identical to the amino acid sequence depicted in SEQ ID NO:2 or 14;
 b) a polynucleotide coding for a polypeptide with an amino acid sequence that is at least 70% identical to the amino acid sequence depicted in SEQ ID NO:4 or 16;
 and of the polynucleotide d) and/or e)
 d) a polynucleotide coding for a polypeptide with an amino acid sequence that is at least 70% identical to the amino acid sequence depicted in SEQ ID NO:8 or 20;
 e) a polynucleotide coding for a polypeptide with an amino acid sequence that is at least 70% identical to the amino acid sequence depicted in SEQ ID NO:10 or 22.

Preference is furthermore given to a microorganism having, compared to the particular starting strain, increased expression of the polynucleotides a), b) c), d) and e), and, where appropriate, f).

An organic-chemical compound means for the purposes of the invention a vitamin such as, for example, thiamine (vitamin B1), riboflavin (vitamin B2), cyanocobalamin (vitamin B12), folic acid (vitamin M), tocopherol (vitamin E) or nicotinic acid/nicotinamide, a nucleoside or nucleotide such as, for example, S-adenosyl-methionine, inosine 5'-monophosphoric acid and guanosine 5'-monophosphoric acid, L-amino acids, or else an amine such as cadaverin, for example. Preference is given to producing L-amino acids and products containing them.

The organic-chemical compound produced and/or secreted by the microorganism according to the invention is preferably selected from the group consisting of vitamin, nucleoside or nucleotide, L-amino acids and amine.

The term "L-amino acid" includes the proteinogenic amino acids and also L-ornithine and L-homoserine. Proteinogenic L-amino acids are to be understood to mean the L-amino acids present in natural proteins, that is in proteins of microorganisms, plants, animals and humans. Proteinogenic amino acids comprise L-aspartic acid, L-asparagine, L-threonine, L-serine, L-glutamic acid, L-glutamine, L-glycine, L-alanine, L-cysteine, L-valine, L-methionine, L-isoleucine, L-leucine, L-tyrosine, L-phenylalanine, L-histidine, L-lysine, L-tryptophan, L-arginine, L-proline and in some cases L-selenocysteine and L-pyrrolysine.

The organic-chemical compound is particularly preferably selected from the group consisting of proteinogenic L-amino acid, L-ornithine and L-homoserine. Particular preference is given to the proteinogenic L-amino acid being selected from the group consisting of L-lysine, L-methionine, L-valine, L-proline, L-glutamate and L-isoleucine, in particular L-lysine.

The term amino acids or L-amino acids, where mentioned herein, also comprises their salts, for example lysine monohydrochloride or lysine sulphate in the case of the amino acid L-lysine.

The microorganism is preferably selected from the group consisting of bacteria, yeast and fungi, particularly preferably among the bacteria from the group consisting of the genus *Corynebacterium* and the bacteria of the Enterobacteriaceae family, with very particular preference being given to the species *Corynebacterium glutamicum*.

In a further, preferred embodiment, expression of the polynucleotide coding for a protein subunit of the ABC transporter having the activity of a trehalose importer is increased by one or more measures selected from the following group:

a) expression of the gene is under the control of a promoter which is stronger in the microorganism used for the method than the original promoter of said gene;
b) increasing the copy number of the gene coding for a polypeptide having the activity of a trehalose importer; preferably by inserting said gene into plasmids with increased copy number and/or by integrating at least one copy of said gene into the chromosome of said microorganism;
c) the gene is expressed using a ribosome binding site which is stronger in the microorganism used for the method than the original ribosome binding site of said gene;
d) the gene is expressed with optimization of the codon usage of the microorganism used for the method;
e) the gene is expressed with reduction of mRNA secondary structures in the mRNA transcribed from said gene;
f) the gene is expressed with elimination of RNA polymerase terminator sequences in the mRNA transcribed from said gene;
g) the gene is expressed with use of mRNA-stabilizing sequences in the mRNA transcribed from said gene.

The above measures for increasing expression may be combined in a suitable manner. Preference is given to increasing expression of the polynucleotide coding for a protein subunit of the ABC transporter having the activity of a trehalose importer by combining at least two of the measures selected from the group consisting of a), b) and c), particularly preferably by combining measures a) and b).

As mentioned above, the present invention also relates to a method for the fermentative production of an organic-chemical compound, comprising the steps:

a) culturing the above-described microorganism according to the present invention in a suitable medium, resulting in a fermentation broth, and
b) accumulating the organic-chemical compound in the fermentation broth of a);

wherein accumulation of trehalose in the fermentation broth is reduced or avoided.

Preference is given to reducing the accumulation of trehalose in the fermentation broth by 50% or more, by 70% or more, by 80% or more, by 90% or more, by 95% or more, by 98% or more, by 99% or more, and most preferably by 99.5% or more, compared to the particular starting strain of the microorganism.

In a preferred method, the microorganism used for culturing has, compared to the particular starting strain, increased expression of one or more polynucleotides according to one of the following definitions I to VIII:

I: increased expression, compared to the particular starting strain, of a polynucleotide selected from the group consisting of a) to f):
  a) a polynucleotide coding for a polypeptide with an amino acid sequence that is at least 70% identical to the amino acid sequence depicted in SEQ ID NO:2 or 14;
  b) a polynucleotide coding for a polypeptide with an amino acid sequence that is at least 70% identical to the amino acid sequence depicted in SEQ ID NO:4 or 16;
  c) a polynucleotide coding for a polypeptide with an amino acid sequence that is at least 70% identical to the amino acid sequence depicted in SEQ ID NO:6 or 18;
  d) a polynucleotide coding for a polypeptide with an amino acid sequence that is at least 70% identical to the amino acid sequence depicted in SEQ ID NO:8 or 20;
  e) a polynucleotide coding for a polypeptide with an amino acid sequence that is at least 70% identical to the amino acid sequence depicted in SEQ ID NO:10 or 22;
  f) a polynucleotide coding for a polypeptide with an amino acid sequence that is at least 70% identical to the amino acid sequence depicted in SEQ ID NO:12 or 24;
II: increased expression, compared to the particular starting strain, of a polynucleotide selected from the group consisting of a), b), d) and e);
III: increased expression, compared to the particular starting strain, of a polynucleotide selected from the group consisting of b), d) and e);
IV: increased expression, compared to the particular starting strain, of the polynucleotide d) and/or e);
V: increased expression, compared to the particular starting strain, of any polynucleotides a), b), d) and e);
VI: increased expression, compared to the particular starting strain, of any polynucleotides a), b), d);
VII: increased expression, compared to the particular starting strain, of any polynucleotides a), b), e);
VIII: increased expression, compared to the particular starting strain, of any polynucleotides a) to e) and, where appropriate, f).

Preference is given to producing from the fermentation broth a product in liquid or solid form.

TABLE 2

| | |
|---|---|
| cat | chloramphenicol resistance gene |
| lacI | coding for Lac repressor |
| Ptac | tac promoter |
| oriCg | origin of Corynebacterium glutamicum plasmid pBL1 |
| ori pUC | origin of Escherichia coli plasmid pUC |
| TrrnB | rrnB terminator |
| cg0831 | coding for permease subunit |
| cg0832 | coding for permease subunit |
| cg0833 | coding for unknown protein |
| cg0834 | coding for periplasmic substrate-binding protein |
| cg0835 | coding for ATPase |

Figure 3:
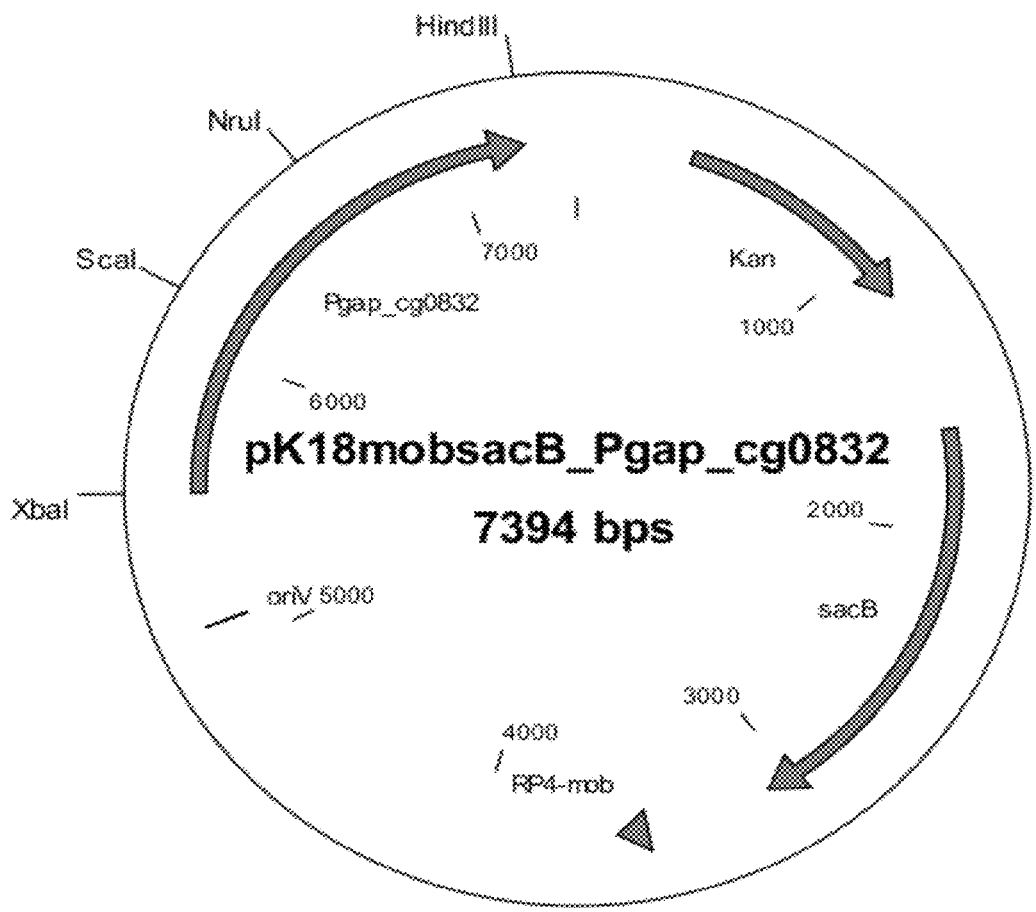

FIG. 3 is a schematic representation of plasmid pK18mobsacB_Pgap_cg0832 used for functionally linking ORF cg0832 to the Pgap promoter. Table 3 below summarizes the abbreviations and names used and also the meaning thereof. The abbreviations and names used have the following meanings. The base pair numbers indicated are approximations obtained within the limits of reproducibility of measurements.

TABLE 3

| | |
|---|---|
| Kan: | kanamycin resistance gene |
| NruI | cleavage site of restriction enzyme NruI |
| HindIII | cleavage site of restriction enzyme HindIII |
| ScaI | cleavage site of restriction enzyme ScaI |
| XbaI | cleavage site of restriction enzyme XbaI |
| Pgap_cg0832 | DNA cassette for establishing functional linkage of ORF cg0832 and the Pgap promoter |
| sacB: | sacB-gene |
| RP4-mob: | mob region containing the origin of replication for transfer (oriT) |
| oriV: | origin of replication V |

DETAILED DESCRIPTION OF THE INVENTION

As mentioned above, the term microorganism comprises bacteria, yeasts and fungi. Among the bacteria, mention may be made in particular of the genus *Corynebacterium* and of bacteria of the Enterobacteriaceae family.

Within the genus *Corynebacterium*, preference is given to strains based on the following species:
  *Corynebacterium efficiens* such as, for example, type strain DSM44549;
  *Corynebacterium glutamicum* such as, for example, type strain ATCC13032 or strain R; and
  *Corynebacterium ammoniagenes* such as, for example, strain ATCC6871;
with the species *Corynebacterium glutamicum* being very particularly preferred.

Some representatives of the species *Corynebacterium glutamicum* are known in the prior art also by different names. These include, for example:
  strain ATCC13870, referred to as *Corynebacterium acetoacidophilum*;
  strain DSM20137, referred to as *Corynebacterium lilium*;
  strain ATCC17965, referred to as *Corynebacterium melassecola*;
  strain ATCC14067, referred to as *Brevibacterium flavum*;
  strain ATCC13869, referred to as *Brevibacterium lactofermentum*; and
  strain ATCC14020, referred to as *Brevibacterium divaricatum*.

The term "*Micrococcus glutamicus*" has likewise been in use for *Corynebacterium glutamicum*. Some representatives of the species *Corynebacterium efficiens* have also been referred to as *Corynebacterium thermoaminogenes* in the prior art, for example the strain FERM BP-1539.

The microorganisms or strains employed for the measures of overexpressing the trehalose importer (starting strains) preferably already have the ability to concentrate the desired L-amino acids in the cell or to secrete them into the surrounding nutrient medium and accumulate them there. The expression "to produce" is also used for this hereinbelow.

More specifically, the strains employed for the measures of overexpression have the ability to concentrate in the cell or accumulate in the nutrient medium≥(at least)≥0.10 g/l, 0.25 g/l, ≥0.5 g/l, ≥1.0 g/l, ≥1.5 g/l, ≥2.0 g/l, ≥4 g/l or ≥10 g/l of the desired compound within ≤(no more than) 120 hours, ≤96 hours, ≤48 hours, ≤36 hours, ≤24 hours or ≤12 hours. The starting strains are preferably strains produced by mutagenesis and selection, by recombinant DNA technology or by a combination of both methods.

A person skilled in the art understands that a microorganism suitable for the measures of the invention can also be obtained by firstly overexpressing a trehalose importer in a wild strain, for example in the *Corynebacterium glutamicum* type strain ATCC 13032 or in the strain ATCC 14067, and then, by means of further genetic measures described in the prior art, causing the microorganism to produce the desired L-amino acid(s). Transforming the wild type only with the polynucleotide mentioned does not constitute an inventive measure.

Examples of strains of the species *Corynebacterium glutamicum* which secrete or produce L-lysine are:
  *Corynebacterium glutamicum* MH20-22B (=DSM16835) described in Menkel, et al. (*Applied and Environmental Microbiology*: 55(3):684-688 (1989)) and deposited as DSM16835;
  *Corynebacterium glutamicum* DM1729 described in Georgi, et al. (*Metabolic Engineering* 7:291-301 (2005)) and in EP 1 717 616 A2 and deposited as DSM17576;
  *Corynebacterium glutamicum* DSM13994 described in U.S. Pat. No. 6,783,967; and
  *Corynebacterium glutamicum* DM1933 described in Blombach, et al. (*Appl. Environ. Microbiol.* 75(2):419-27 (January 2009).

An example of a strain of the species *Corynebacterium efficiens* which secretes or produces L-lysine is: *Corynebacterium thermoaminogenes* AJ12521 (=FERM BP-3304) described in U.S. Pat. No. 5,250,423.

L-Lysine-producing microorganisms typically have a feedback-resistant or desensitized aspartate kinase. Feedback-resistant aspartate kinases mean aspartate kinases (LysC) which, by comparison with the wild form (wild type), show less sensitivity to inhibition by mixtures of lysine and threonine or mixtures of AEC (aminoethylcysteine) and threonine or lysine alone or AEC alone. The genes or alleles coding for these aspartate kinases which are desensitized by comparison with the wild type are also referred to as lysC$^{FBR}$ alleles. The suitable wild type in the case of aspartate kinases of the species *Corynebacterium glutamicum* is the strain ATCC13032. Numerous lysC$^{FBR}$ alleles coding for aspartate kinase variants which have amino acid substitutions by comparison with the wild-type protein are described in the prior art. The lysC gene in bacteria of the genus *Corynebacterium* is also referred to as ask gene. The aspartate kinase encoded by the lysC gene in Enterobacteriaceae is also referred to as aspartokinase III.

An extensive list containing information about the amino acid substitutions in the *Corynebacterium glutamicum* aspartate kinase protein that result in desensitization is included inter alia in WO2009141330. Preference is given to aspartate kinase variants carrying amino acid substitutions selected from the group consisting of: L-isoleucine for L-threonine at position 380 of the amino acid sequence and optionally L-phenylalanine for L-serine at position 381, L-isoleucine for L-threonine at position 311 and L-threonine for L-alanine at position 279.

An extensive list containing information about the amino acid substitutions in the *Escherichia coli* aspartate kinase III protein that result in desensitization to inhibition by L-lysine is included inter alia in EP 0 834 559 A1 on page 3 (lines 29 to 41). Preference is given to an aspartate kinase variant containing L-aspartic acid instead of glycine at position 323 of the amino acid sequence and/or L-isoleucine instead of L-methionine at position 318.

An example of a strain of the species *Corynebacterium glutamicum* which secretes or produces L-methionine is *Corynebacterium glutamicum* DSM 17322 described in WO 2007/011939.

Examples of known representatives of coryneform bacterial strains that produce or secrete L-tryptophan are:
*Corynebacterium glutamicum* K76 (=Ferm BP-1847) described in U.S. Pat. No. 5,563,052;
*Corynebacterium glutamicum* BPS13 (=Ferm BP-1777) described in U.S. Pat. No. 5,605,818; and
*Corynebacterium glutamicum* Ferm BP-3055 described in U.S. Pat. No. 5,235,940.

Examples of known representatives of coryneform bacterial strains that produce or secrete L-valine are:
*Brevibacterium lactofermentum* FERM BP-1763 described in U.S. Pat. No. 5,188,948;
*Brevibacterium lactofermentum* FERM BP-3007 described in U.S. Pat. No. 5,521,074;
*Corynebacterium glutamicum* FERM BP-3006 described in U.S. Pat. No. 5,521,074; and
*Corynebacterium glutamicum* FERM BP-1764 described in U.S. Pat. No. 5,188,948.

Examples of known representatives of coryneform bacterial strains that produce or secrete L-isoleucine are:
*Brevibacterium flavum* FERM BP-760 described in U.S. Pat. No. 4,656,135;
*Brevibacterium flavum* FERM BP-2215 described in U.S. Pat. No. 5,294,547; and
*Corynebacterium glutamicum* FERM BP-758 described in U.S. Pat. No. 4,656,135.

Examples of known representatives of coryneform bacterial strains that produce or secrete L-homoserine are:
*Micrococcus glutamicus* ATCC 14296 described in U.S. Pat. No. 3,189,526; and
*Micrococcus glutamicus* ATCC 14297 described in U.S. Pat. No. 3,189,526.

Cadaverine-producing or -secreting microorganisms are described, for example, in WO 2007/113127.

An ABC transporter having the activity of a trehalose importer means a protein or a protein complex with multiple subunits which catalyzes the transport of trehalose from the surrounding area into the cell of the microorganism in question.

ABC transporters constitute one of the largest families of membrane proteins, a common structural element of which is an ATP-binding cassette and which actively transport specific substrates across a cellular membrane. The energy needed for transporting the substrates of ABC transporters against a concentration gradient is produced by binding and hydrolysis of ATP on the ATPase unit.

The structure of a prokaryotic ABC transporter normally consists of three parts: two integral membrane proteins (permease), each one having from five to seven transmembrane segments, two additional proteins which bind and hydrolyse ATP (ATPase), and a periplasmic substrate-binding protein (or membrane-anchored lipoprotein). Many of the genes for said three parts form operons. ABC transporters thus belong firstly to the primarily active transporters and secondly to the membrane-bound ATPases.

Public databases such as, for example, the UniProtKB (Universal Protein Resource Knowledgebase) database contain descriptions of ABC transporters of very different organisms. The UniProtKB database is maintained by the UniProt consortium which includes the European Bioinformatics Institute (EBI, Wellcome Trust, Hinxton Cambridge, United Kingdom), the Swiss Institute of Bioinformatics (SIB, Centre Medical Universitaire, Geneva, Switzerland) and the Protein Information Resource (PIR, Georgetown University, Washington, D.C., US).

The genes for a trehalose importer may be isolated from the organisms with the aid of the polymerase chain reaction (PCR) using suitable primers. Instructions can be found inter alia in the laboratory manual "PCR" by Newton and Graham (Spektrum Akademischer Verlag, Heidelberg, Germany, 1994) and in WO 2006/100211, pages 14 to 17.

The measures of the invention may make use of the genes of the trehalose importer from *corynebacteria*. Preference is given to using genes coding for polypeptides which have trehalose importer activity and whose amino acid sequence is ≥(at least)≥50%, ≥60%, ≥70%, ≥80%, ≥90%, ≥92%, ≥94%, ≥96%, ≥97%, ≥98%, ≥99%, identical to the amino acid sequence selected from SEQ ID NO: 2, 4, 6, 8, 10 and, where appropriate, 12, or 14, 16, 18, 20, 22, 24. In the course of the studies resulting in the present invention, the operon coding for the trehalose importer of *Corynebacterium glutamicum* was identified. The operon encoding the trehalose importer in *Corynebacterium glutamicum* has multiple reading frames or genes.

Table 1 summarizes the information regarding the reading frames of the operon coding for the *Corynebacterium glutamicum* trehalose importer.

TABLE 1

The genes/reading frames of the operon coding for the *Corynebacterium glutamicum* trehalose importer

| Name of the reading frame in the operon | coding for | Length (number of amino acid residues) | SEQ ID NO: |
|---|---|---|---|
| cg0835 (msik2) | ATPase | 332 | 2 |
| cg0834 | periplasmic substrate-binding protein | 424 | 4 |
| cg0833 | unknown | 151 | 6 |
| cg0832 | permease | 344 | 8 |
| cg0831 | permease | 278 | 10 |
| cg0830 | hypothetical reading frame | 74 | 12 |

Figure 1:
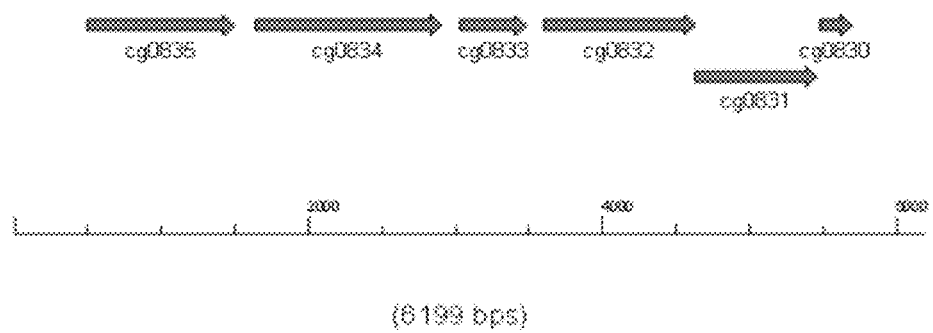
FIG. 1 depicts the arrangement of open reading frames cg0835 to cg0830. The reading frames code for the following putative proteins: cg0835: ATPase; cg0834 periplasmic substrate-binding protein; cg0832: permease subunit; cg0831 permease subunit.

The genomic arrangement of the reading frames is depicted in FIG. 1, and the sequence of the region is listed under SEQ ID NO:25.

From a chemical point of view, a gene is a polynucleotide. A polynucleotide encoding a protein/polypeptide is used herein synonymously with the term "gene".

A preferred embodiment of the microorganism overexpresses one or more gene(s) coding for one or more polypeptide(s) selected from a) to f) below:

a)
i) a polypeptide consisting of or comprising the amino acid sequence depicted in SEQ ID NO: 2;
ii) a polypeptide with an amino acid sequence that is at least 70% identical to the amino acid sequence of i), said polypeptide being a subunit of a protein complex having the activity of a trehalose importer;
iii) a polypeptide having an amino acid sequence containing a deletion, substitution, insertion and/or addition of from 1 to 66, 1 to 33, 1 to 17, 1 to 7, amino acid residues with respect to the amino acid sequence depicted in SEQ ID NO: 2, said polypeptide being a subunit of a protein complex having the activity of a trehalose importer;

b)
i) a polypeptide consisting of or comprising the amino acid sequence depicted in SEQ ID NO: 4;
ii) a polypeptide with an amino acid sequence that is at least 70% identical to the amino acid sequence of i), said polypeptide being a subunit of a protein complex having the activity of a trehalose importer;
iii) a polypeptide having an amino acid sequence containing a deletion, substitution, insertion and/or addition of from 1 to 85, 1 to 42, 1 to 21, 1 to 9, amino acid residues with respect to the amino acid sequence depicted in SEQ ID NO: 4, said polypeptide being a subunit of a protein complex having the activity of a trehalose importer;

c)
i) a polypeptide consisting of or comprising the amino acid sequence depicted in SEQ ID NO: 6;
ii) a polypeptide with an amino acid sequence that is at least 70% identical to the amino acid sequence of i), said polypeptide being a subunit of a protein complex having the activity of a trehalose importer;
iii) a polypeptide having an amino acid sequence containing a deletion, substitution, insertion and/or addition of from 1 to 30, 1 to 15, 1 to 6, 1 to 3, amino acid residues with respect to the amino acid sequence depicted in SEQ ID NO: 6, said polypeptide being a subunit of a protein complex having the activity of a trehalose importer;

d)
i) a polypeptide consisting of or comprising the amino acid sequence depicted in SEQ ID NO: 8;
ii) a polypeptide with an amino acid sequence that is at least 70% identical to the amino acid sequence of i), said polypeptide being a subunit of a protein complex having the activity of a trehalose importer;
iii) a polypeptide having an amino acid sequence containing a deletion, substitution, insertion and/or addition of from 1 to 69, 1 to 34, 1 to 17, 1 to 7, amino acid residues with respect to the amino acid sequence depicted in SEQ ID NO: 8, said polypeptide being a subunit of a protein complex having the activity of a trehalose importer;

e)
i) a polypeptide consisting of or comprising the amino acid sequence depicted in SEQ ID NO: 10;
ii) a polypeptide with an amino acid sequence that is at least 70% identical to the amino acid sequence of i), said polypeptide being a subunit of a protein complex having the activity of a trehalose importer;
iii) a polypeptide having an amino acid sequence containing a deletion, substitution, insertion and/or addition of from 1 to 56, 1 to 28, 1 to 14, 1 to 6, amino acid residues with respect to the amino acid sequence depicted in SEQ ID NO: 10, said polypeptide being a subunit of a protein complex having the activity of a trehalose importer;

f)
i) a polypeptide consisting of or comprising the amino acid sequence depicted in SEQ ID NO: 12;
ii) a polypeptide with an amino acid sequence that is at least 70% identical to the amino acid sequence of i), said polypeptide being a subunit of a protein complex having the activity of a trehalose importer;
iii) a polypeptide having an amino acid sequence containing a deletion, substitution, insertion and/or addition of from 1 to 15, 1 to 8, 1 to 4, 1 to 2, amino acid residues with respect to the amino acid sequence depicted in SEQ ID NO: 12, said polypeptide being a subunit of a protein complex having the activity of a trehalose importer.

Preferred embodiments comprise variants which are at least 75%, at least 80%, at least 85%, at least 90%, at least 95%, at least 98% or at least 99%, identical to the above-described amino acid sequences, i.e. with at least 75%, at least 80%, at least 85%, at least 90%, at least 95%, at least 98% or at least 99%, of the amino acid positions being identical to those of the above-described amino acid sequences. Percentage identity is preferably calculated over the entire length of the amino acid or nucleic acid region. A person skilled in the art has a number of programs, based on a multiplicity of algorithms, available for sequence comparison. In this context, the algorithms of Needleman and Wunsch or Smith and Waterman produce particularly reliable results. The program PileUp (*J. Mol. Evolution.* 25:351-360 (1987); Higgins, et al., *CABIOS* 5:151-153 (1989)) or the programs Gap and BestFit (Needleman and Wunsch, *J. Mol. Biol.* 48:443-453 (1970) and Smith and Waterman, *Adv. Appl. Math.* 2:482-489 (1981)), which are part of the GCG software package (Genetics Computer Group, 575 Science Drive, Madison, Wis., USA 53711 (1991)), are available for the alignment of sequences. The sequence identity percentages listed above are preferably calculated over the entire sequence region using the GAP program.

Where appropriate, preference is given to conservative amino acid substitutions. In the case of aromatic amino acids, conservative substitutions are those in which phenylalanine, tryptophan and tyrosine are substituted for each other. In the case of hydrophobic amino acids, conservative substitutions are those in which leucine, isoleucine and valine are substituted for one another. In the case of polar amino acids, conservative substitutions are those in which glutamine and asparagine are substituted for one another. In the case of basic amino acids, conservative substitutions are those in which arginine, lysine and histidine are substituted for one another. In the case of acidic amino acids, conservative substitutions are those in which aspartic acid and glutamic acid are substituted for one another. In the case of the amino acids containing hydroxyl groups, conservative substitutions are those in which serine and threonine are substituted for one another.

It is furthermore possible to use polynucleotides which hybridize under stringent conditions with the nucleotide sequence complementary to SEQ ID NO: 1, 3, 5, 7, 9, 11, preferably to the coding region of SEQ ID NO: 1, 3, 5, 7, 9, 11, and code for a polypeptide which is part of a trehalose importer.

Instructions regarding the hybridization of nucleic acids or polynucleotides can be found by the skilled worker inter alia in the manual "The DIG System Users Guide for Filter Hybridization" from Boehringer Mannheim GmbH (Mannheim, Germany, 1993) and in Liebl et al. (*International*

*Journal of Systematic Bacteriology* 41:255-260 (1991)). Hybridization takes place under stringent conditions, that is to say only hybrids in which the probe (i.e. a polynucleotide comprising the nucleotide sequence complementary to SEQ ID NO: 1, 3, 5, 7, 9, 11, preferably the coding region of SEQ ID NO: 1, 3, 5, 7, 9, 11) and the target sequence (i.e. the polynucleotides treated with or identified by said probe) are at least 70% identical are formed. The stringency of the hybridization, including the washing steps, is known to be influenced or determined by varying the buffer composition, temperature and salt concentration. The hybridization reaction is generally carried out with relatively low stringency compared with the washing steps (Hybaid Hybridisation Guide, Hybaid Limited, Teddington, UK, 1996).

For example, a 5×SSC buffer at a temperature of approx. 50° C.-68° C. may be employed for the hybridization reaction. Here, probes may also hybridize with polynucleotides which are less than 70% identical to the nucleotide sequence of the probe employed. Such hybrids are less stable and are removed by washing under stringent conditions. This may be achieved, for example, by lowering the salt concentration to 2×SSC or 1×SSC and, where appropriate, subsequently 0.5× SSC (The DIG System User's Guide for Filter Hybridisation, Boehringer Mannheim, Mannheim, Germany, 1995), with a temperature of approx. 50° C.-68° C., approx. 52° C.-68° C., approx. 54° C.-68° C., approx. 56° C.-68° C., approx. 58° C.-68° C., approx. 60° C.-68° C., approx. 62° C.-68° C., approx. 64° C.-68° C., approx. 66° C.-68° C. being set. Preference is given to temperature ranges of approx. 64° C.-68° C. or approx. 66° C.-68° C. It is optionally possible to lower the salt concentration to a concentration corresponding to 0.2× SSC or 0.1×SSC. The SSC buffer optionally contains sodium dodecylsulphate (SDS) at a concentration of 0.1%. By gradually increasing the hybridization temperature in steps of approx. 1-2° C. from 50° C. to 68° C., it is possible to isolate polynucleotide fragments which are at least 70%, at least 80%, at least 90%, at least 92%, at least 94%, at least 96%, at least 97%, at least 98%, or at least 99%, where appropriate 100%, identical to the sequence or complementary sequence of the probe employed and which code for a polypeptide which is part of a trehalose importer. Further instructions regarding hybridization are obtainable on the market in the form of "kits" (e.g. DIG Easy Hyb from Roche Diagnostics GmbH, Mannheim, Germany, Catalogue No. 1603558).

For the measures of the invention, a gene coding for a part of a trehalose importer is overexpressed in a microorganism or starting or parent strain producing the desired amino acid(s). Overexpression generally means an increase in the intracellular concentration or activity of a ribonucleic acid, of a protein (polypeptide) or of an enzyme by comparison with the starting strain (parent strain) or wild-type strain, if the latter is the starting strain. A starting strain (parent strain) means the strain on which the measure leading to overexpression has been carried out.

For overexpression, preference is given to the methods of recombinant overexpression. These include all methods in which a microorganism is prepared using a DNA molecule provided in vitro. Examples of such DNA molecules include promoters, expression cassettes, genes, alleles, coding regions, etc. They are transferred by methods of transformation, conjugation, transduction or similar methods into the desired microorganism.

The measures of overexpression increase the activity or concentration of the corresponding polypeptides generally by at least 10%, 25%, 50%, 75%, 100%, 150%, 200%, 300%, 400% or 500%, preferably at most by 1000%, 2000%, 4000%, 10000% or 20000%, based on the activity or concentration of said polypeptide in the strain prior to the measure resulting in overexpression.

Overexpression is achieved by a multiplicity of methods available in the prior art. These include increasing the copy number and modifying the nucleotide sequences directing or controlling expression of the gene. The transcription of a gene is controlled inter alia by the promoter and optionally by proteins which suppress (repressor proteins) or promote (activator proteins) transcription. The translation of the RNA formed is controlled inter alia by the ribosome binding site and the start codon. Polynucleotides or DNA molecules which include a promoter and a ribosome binding site and optionally a start codon are also referred to as expression cassette.

The copy number may be increased by means of plasmids which replicate in the cytoplasm of the microorganism. To this end, an abundance of plasmids are described in the prior art for very different groups of microorganisms, which plasmids can be used for setting the desired increase in the copy number of the gene. Plasmids suitable for the genus *Escherichia* are described, for example, in the manual Molecular Biology, Labfax (ed.: T. A. Brown, Bios Scientific, Oxford, UK, 1991). Plasmids suitable for the genus *Corynebacterium* are described, for example, in Tauch, et al. (*J. Biotechnology* 104(1-3):27-40, (2003)), or in Stansen, et al. (*Applied and Environmental Microbiology* 71:5920-5928 (2005)).

The copy number may furthermore be increased by at least one (1) copy by introducing further copies into the chromosome of the microorganism. Methods suitable for the genus *Corynebacterium* are described, for example, in the WO 03/014330, WO 03/040373 and WO 04/069996. Examples of methods suitable for the genus *Escherichia* are insertion of a gene copy into the att site of the phage (Yu, et al., *Gene* 223:77-81 (1998)), chromosomal amplification with the aid of the phage Mu, as described in EP 0 332 448, or the methods of gene replacement with the aid of conditionally replicating plasmids, as described by Hamilton, et al. (*J. Bacteriol.* 174: 4617-4622 (1989)) or Link, et al. (*J. Bacteriol.* 179:6228-6237 (1997)).

Gene expression may furthermore be increased by using a strong promoter which is functionally linked to the gene to be expressed. Preference is given to using a promoter which is stronger than the natural promoter, i.e., the one present in the wild type or parent strain. To this end, the prior art has an abundance of methods available. "Functionallinkage" in this context means the sequential arrangement of a promoter with a gene, resulting in expression of said gene and control thereof.

Promoters suitable for the genus *Corynebacterium* can be found inter alia in Morinaga, et al. (*J. Biotechnol.* 5:305-312, (1987)), in the patent documents EP 0 629 699 A2, US 2007/ 0259408 A1, WO 2006/069711, EP 1 881 076 A1 and EP 1 918 378 A1 and in reviews such as the "Handbook of *Corynebacterium glutamicum*" (eds.: Lothar Eggeling and Michael Bott, CRC Press, Boca Raton, US (2005)) or the book "*Corynebacteria*, Genomics and Molecular Biology" (Ed.: Andreas Burkovski, Caister Academic Press, Norfolk, UK (2008)). Examples of promoters which allow controlled, i.e., inducible or repressible, expression are described, for example, in Tsuchiya, et al. (*Bio/Technology* 6{428-430 (1988)). Such promoters or expression cassettes are typically employed at a distance of from 1 to 1000, preferably 1 to 500, nucleotides upstream of the first nucleotide of the start codon of the coding region of the gene. It is likewise possible to place a plurality of promoters upstream of the desired gene or functionally link them to the gene to be expressed and in this way achieve increased expression. Examples of this are described in the patent WO 2006/069711.

The structure of *Escherichia coli* promoters is well known. It is therefore possible to increase the strength of a promoter by modifying its sequence by means of one or more substitution(s) and/or one or more insertion(s) and/or one or more deletion(s) of nucleotides. Examples of this can be found inter alia in "Herder Lexikon der Biologie" (Spektrum Akademischer Verlag, Heidelberg, Germany (1994)). Examples of the modification of promoters for increasing expression in coryneform bacteria can be found in U.S. Pat. No. 6,962,805 B2 and in a publication by Vasicová et al. (Bacteriol. 1999 October; 181(19):6188-91). Enhancing a target gene by substituting a homologous promoter is described, for example, in EP 1 697 526 B1.

The structure of the *Corynebacterium glutamicum* ribosome binding site is likewise well known and is described, for example, in Amador (Microbiology 145, 915-924 (1999)), and in manuals and textbooks of genetics, for example "Gene and Klone" (Winnacker, Verlag Chemie, Weinheim, Germany (1990)) or "Molecular Genetics of Bacteria" (Dale and Park, Wiley and Sons Ltd., Chichester, UK (2004)).

Overexpression can likewise be achieved by increasing the expression of activator proteins or reducing or switching off the expression of repressor proteins.

The overexpression measures mentioned may be combined with one another in a suitable manner. Thus it is possible, for example, to combine the use of a suitable expression cassette with increasing the copy number or, preferably, the use of a suitable promoter with increasing the copy number.

Instructions regarding the handling of DNA, digestion and ligation of DNA, transformation and selection of transformants can be found inter alia in the known manual by Sambrook, et al. "Molecular Cloning: A Laboratory Manual, Second Edition" (Cold Spring Harbor Laboratory Press, 1989).

The extent of expression or overexpression can be determined by measuring the amount of the mRNA transcribed from the gene, by determining the amount of the polypeptide and by determining the enzyme activity. The amount of mRNA may be determined inter alia by using the methods of "Northern blotting" and of quantitative RT-PCR. Quantitative RT-PCR involves reverse transcription preceding the polymerase chain reaction. For this, the LightCycler™ system from Roche Diagnostics (Boehringer Mannheim GmbH, Roche Molecular Biochemicals, Mannheim, Germany) may be used, as described, for example, in Jungwirth, et al. (*FEMS Microbiology Letters* 281:190-197 (2008)).

The concentration of the protein may be determined via 1- and 2-dimensional protein gel fractionation and subsequent optical identification of the protein concentration by appropriate evaluation software in the gel. A customary method of preparing protein gels for coryneform bacteria and of identifying said proteins is the procedure described by Hermann, et al. (*Electrophoresis* 22:1712-23 (2001)). The protein concentration may likewise be determined by Western blot hybridization using an antibody specific for the protein to be detected (Sambrook et al., Molecular cloning: a laboratory manual. $2^{nd}$ Ed. Cold Spring Harbor Laboratory Press, Cold Spring Harbor, N.Y., 1989) and subsequent optical evaluation using corresponding software for concentration determination (Lohaus, et al., *Biospektrum* 5:32-39 (1998); Lottspeich, *Angewandte Chemie* 321:2630-2647 (1999)).

The microorganisms produced may be cultured continuously—as described, for example, in WO 05/021772—or discontinuously in a batch process (batch cultivation) or in a fed batch or repeated fed batch process for the purpose of producing the desired organic-chemical compound. A summary of a general nature about known cultivation methods is available in the textbook by Chmiel (Bioprozesstechnik 1. Einführung in die Bioverfahrenstechnik (Gustav Fischer Verlag, Stuttgart, 1991)) or in the textbook by Storhas (Bioreaktoren and periphere Einrichtungen (Vieweg Verlag, Brunswick/Wiesbaden, 1994)).

The culture medium or fermentation medium to be used must in a suitable manner satisfy the demands of the respective strains. Descriptions of culture media for various microorganisms are present in the "Manual of Methods for General Bacteriology" of the American Society for Bacteriology (Washington D.C., USA, 1981). The terms culture medium and fermentation medium or medium are interchangeable.

It is possible to use, as carbon source, sugars and carbohydrates such as, for example, glucose, sucrose, lactose, fructose, maltose, molasses, sucrose-containing solutions from sugar beet or sugar cane processing, starch, starch hydrolysate and cellulose, oils and fats such as, for example, soybean oil, sunflower oil, groundnut oil and coconut fat, fatty acids such as, for example, palmitic acid, stearic acid and linoleic acid, alcohols such as, for example, glycerol, methanol and ethanol, and organic acids such as, for example, acetic acid or lactic acid.

It is possible to use, as nitrogen source, organic nitrogen-containing compounds such as peptones, yeast extract, meat extract, malt extract, corn steep liquor, soybean flour and urea, or inorganic compounds such as ammonium sulphate, ammonium chloride, ammonium phosphate, ammonium carbonate and ammonium nitrate. The nitrogen sources can be used individually or as mixture.

It is possible to use, as phosphorus source, phosphoric acid, potassium dihydrogen phosphate or dipotassium hydrogen phosphate or the corresponding sodium-containing salts.

The culture medium must additionally comprise salts, for example in the form of chlorides or sulphates of metals such as, for example, sodium, potassium, magnesium, calcium and iron, such as, for example, magnesium sulphate or iron sulphate, which are necessary for growth. Finally, essential growth factors such as amino acids, for example homoserine and vitamins, for example thiamine, biotin or pantothenic acid, may be employed in addition to the above-mentioned substances.

The starting materials may be added to the culture in the form of a single batch or be fed in during the cultivation in a suitable manner.

The pH of the culture can be controlled by employing basic compounds such as sodium hydroxide, potassium hydroxide, ammonia or aqueous ammonia, or acidic compounds such as phosphoric acid or sulphuric acid in a suitable manner. The pH is generally adjusted to a value of from 6.0 to 8.5, preferably 6.5 to 8. To control foaming, it is possible to employ antifoams such as, for example, fatty acid polyglycol esters. To maintain the stability of plasmids, it is possible to add to the medium suitable selective substances such as, for example, antibiotics. The fermentation is preferably carried out under aerobic conditions. In order to maintain these conditions, oxygen or oxygen-containing gas mixtures such as, for example, air are introduced into the culture. It is likewise possible to use liquids enriched with hydrogen peroxide. The fermentation is carried out, where appropriate, at elevated pressure, for example at an elevated pressure of from 0.03 to 0.2 MPa. The temperature of the culture is normally from 20° C. to 45° C. and preferably from 25° C. to 40° C., particularly preferably from 30° C. to 37° C. In batch processes, the cultivation is preferably continued until an amount of the desired organic-chemical compound sufficient for being recovered has formed. This aim is normally achieved within 10 hours to 160 hours. In continuous processes, longer cultivation times are possible. The activity of the microorganisms results in a concentration (accumulation) of the organic-chemical compound in the fermentation medium and/or in the cells of said microorganisms.

Examples of suitable fermentation media can be found inter alia in the U.S. Pat. No. 5,770,409, U.S. Pat. No. 5,990,350, U.S. Pat. No. 5,275,940, WO 2007/012078, U.S. Pat. No. 5,827,698, WO 2009/043803, U.S. Pat. No. 5,756,345 and U.S. Pat. No. 7,138,266.

Analysis of L-amino acids to determine the concentration at one or more time(s) during the fermentation can take place by separating the L-amino acids by means of ion exchange chromatography, preferably cation exchange chromatography, with subsequent post-column derivatization using ninhydrin, as described in Spackman et al. (Analytical Chemistry 30: 1190-1206 (1958)). It is also possible to employ ortho-phthalaldehyde rather than ninhydrin for post-column derivatization. An overview article on ion exchange chromatography can be found in Pickering (*LC•GC* (*Magazine of Chromatographic Science* 7(6):484-487 (1989)).

It is likewise possible to carry out a pre-column derivatization, for example using ortho-phthalaldehyde or phenyl isothiocyanate, and to fractionate the resulting amino acid derivates by reversed-phase chromatography (RP), preferably in the form of high-performance liquid chromatography (HPLC). A method of this type is described, for example, in Lindroth, et al. (*Analytical Chemistry* 51:1167-1174 (1979)). Detection is carried out photometrically (absorption, fluorescence). A review regarding amino acid analysis can be found inter alia in the textbook "Bioanalytik" by Lottspeich and Zorbas (Spektrum Akademischer Verlag, Heidelberg, Germany 1998).

The performance of the methods or fermentation processes according to the invention, in terms of one or more of the parameters selected from the group of concentration (compound formed per unit volume), yield (compound formed per unit carbon source consumed), formation (compound formed per unit volume and time) and specific formation (compound formed per unit dry cell matter or dry biomass and time or compound formed per unit cellular protein and time) or else other process parameters and combinations thereof, is increased by at least 0.5%, at least 1%, at least 1.5% or at least 2%, based on methods or fermentation processes using microorganisms containing an increased trehalose importer activity.

The fermentation measures result in a fermentation broth which contains the desired organic-chemical compound, preferably L-amino acid. A product containing the organic-chemical compound is then provided or produced or recovered in liquid or solid form.

A "fermentation broth" means a fermentation medium or nutrient medium in which a microorganism has been cultivated for a certain time and at a certain temperature. The fermentation medium or the media employed during fermentation comprise(s) all the substances or components which ensure production of the desired compound and typically propagation and viability.

When the fermentation is complete, the resulting fermentation broth accordingly comprises:
 a) the biomass (cell mass) of the microorganism, said biomass having been produced due to propagation of the cells of said microorganism,
 b) the desired organic-chemical compound formed during the fermentation,
 c) the organic by-products formed during the fermentation, and
 d) the constituents of the fermentation medium employed or of the starting materials, such as, for example, vitamins such as biotin or salts such as magnesium sulphate, which have not been consumed in the fermentation.

The organic by-products include substances which are produced and optionally secreted by the microorganisms employed in the fermentation in addition to the particular desired compound. These also include sugars such as, for example, trehalose.

The fermentation broth is removed from the culture vessel or fermentation tank, collected where appropriate, and used for providing a product containing the organic-chemical compound, preferably an L-amino acid-containing product, in liquid or solid form. The expression "recovering the L-amino acid-containing product" is also used for this. In the simplest case, the L-amino acid-containing fermentation broth itself, which has been removed from the fermentation tank, constitutes the recovered product.

One or more of the measures selected from the group consisting of:
 a) partial (>0% to <80%) to complete (100%) or virtually complete (≥80%, ≥90%, ≥95%, ≥96%, ≥97%, ≥98%, ≥99%) removal of the water,
 b) partial (>0% to <80%) to complete (100%) or virtually complete (≥80%, ≥90%, ≥95%, ≥96%, ≥97%, ≥98%, ≥99%) removal of the biomass, the latter being optionally inactivated before removal,
 c) partial (>0% to <80%) to complete (100%) or virtually complete (≥80%, ≥90%, ≥95%, ≥96%, ≥97%, ≥98%, ≥99%, ≥99.3%, ≥99.7%) removal of the organic by-products formed during fermentation, and
 d) partial (>0%) to complete (100%) or virtually complete (≥80%, ≥90%, ≥95%, ≥96%, ≥97%, ≥98%, ≥99%, ≥99.3%, ≥99.7%) removal of the constituents of the fermentation medium employed or of the starting materials, which have not been consumed in the fermentation, from the fermentation broth achieves concentration or purification of the desired organic-chemical compound. Products having a desired content of said compound are isolated in this way.

The partial (>0% to <80%) to complete (100%) or virtually complete (≥80% to <100%) removal of the water (measure a)) is also referred to as drying. In one variant of the method, complete or virtually complete removal of the water, of the biomass, of the organic by-products and of the unconsumed constituents of the fermentation medium employed results in pure (≥80% by weight, ≥90% by weight) or high-purity (≥95% by weight, ≥97% by weight, ≥99% by weight) product forms of the desired organic-chemical compound, preferably L-amino acids. An abundance of technical instructions for measures a), b), c) and d) are available in the prior art.

In the case of the amino acid L-lysine, essentially four different product forms are known in the prior art. One group of L-lysine-containing products includes concentrated aqueous alkaline solutions of purified L-lysine (EP-B-0534865). A further group, as described for example in U.S. Pat. No. 6,340,486 and U.S. Pat. No. 6,465,025, includes aqueous acidic biomass-containing concentrates of L-lysine-containing fermentation broths. The best-known group of solid products includes pulverulent or crystalline forms of purified or pure L-lysine, which is typically in the form of a salt such as, for example, L-lysine monohydrochloride. A further group of solid product forms is described for example in EP-B-0533039. The product form described therein comprises besides L-lysine most of the starting materials used during the fermentative production and not consumed and, where appropriate, the biomass of the microorganism employed with a proportion of >0%-100%.

A wide variety of processes appropriate for the various product forms are known for producing the L-lysine-containing product or the purified L-lysine from the fermentation broth. The methods essentially used to produce pure solid L-lysine are those of ion exchange chromatography, where appropriate with use of activated carbon, and methods of crystallization. The corresponding base or a corresponding salt such as, for example, the monohydrochloride (Lys-HCl) or lysine sulphate ($Lys_2$-$H_2SO_4$) is obtained in this way.

EP-B-0534865 describes a process for producing aqueous basic L-lysine-containing solutions from fermentation broths. In the process described therein, the biomass is separated from the fermentation broth and discarded. A base such as, for example, sodium hydroxide, potassium hydroxide or ammonium hydroxide is used to set a pH of between 9 and 11. The mineral constituents (inorganic salts) are removed from the broth by crystallization after concentration and cooling and are either used as fertilizer or discarded. In processes for producing lysine by using bacteria of the genus *Corynebacterium*, preferred processes are those resulting in products which comprise constituents of the fermentation broth. These are used in particular as animal feed additives.

Depending on requirements, the biomass can be removed wholly or partly from the fermentation broth by separation methods such as, for example, centrifugation, filtration, decantation or a combination thereof, or be left completely therein. Where appropriate, the biomass or the biomass-containing fermentation broth is inactivated during a suitable process step, for example by thermal treatment (heating) or by addition of acid.

In one procedure, the biomass is completely or virtually completely removed so that no (0%) or at most 30%, at most 20%, at most 10%, at most 5%, at most 1% or at most 0.1% biomass remains in the prepared product. In a further procedure, the biomass is not removed, or is removed only in small proportions, so that all (100%) or more than 70%, 80%, 90%, 95%, 99% or 99.9% biomass remains in the product prepared. In one method according to the invention, accordingly, the biomass is removed in proportions of from ≥0% to ≤100%.

Finally, the fermentation broth obtained after the fermentation can be adjusted, before or after the complete or partial removal of the biomass, to an acidic pH with an inorganic acid such as, for example, hydrochloric acid, sulphuric acid or phosphoric acid, or organic acids such as, for example, propionic acid (GB 1,439,728 or EP 1 331 220). It is likewise possible to acidify the fermentation broth with the complete content of biomass. Finally, the broth can also be stabilized by adding sodium bisulphite ($NaHSO_3$, GB 1,439,728) or another salt, for example ammonium, alkali metal or alkaline earth metal salt of sulphurous acid.

During the removal of the biomass, any organic or inorganic solids present in the fermentation broth are partially or completely removed. The organic by-products dissolved in the fermentation broth, and the dissolved unconsumed constituents of the fermentation medium (starting materials), remain at least partly (>0%), preferably to an extent of at least 25%, particularly preferably to an extent of at least 50% and very particularly preferably to an extent of at least 75%, in the product. Where appropriate, they also remain completely (100%) or virtually completely, meaning >95% or >98% or greater than 99%, in the product. If a product in this sense comprises at least part of the constituents of the fermentation broth, this is also described by the term "product based on fermentation broth."

Subsequently, water is removed from the broth, or it is thickened or concentrated, by known methods such as, for example, using a rotary evaporator, thin-film evaporator, falling-film evaporator, by reverse osmosis or by nanofiltration. This concentrated fermentation broth can then be worked up to free-flowing products, in particular to a fine powder or preferably coarse granules, by methods of freeze drying, spray drying, spray granulation or by other processes as described for example in the circulating fluidized bed according to PCT/EP2004/006655. A desired product is isolated where appropriate from the resulting granules by screening or dust removal. It is likewise possible to dry the fermentation broth directly, i.e., without previous concentration by spray drying or spray granulation. "Free-flowing" means powders which, from of a series of glass orifice vessels with orifices of different sizes, flow unimpeded at least out of the vessel with a 5 mm (millimeter) orifice (Klein: Seifen, Öle, Fette, Wachse 94, 12 (1968)). "Fine" means a powder predominantly (>50%) having a particle size of diameter from 20 to 200 µm. "Coarse" means a product predominantly (>50%) having a particle size of diameter from 200 to 2000 µm.

The particle size determination can be carried out by methods of laser diffraction spectrometry. Corresponding methods are described in the textbook on "Teilchengrößenmessung in der Laborpraxis" (particle size measurement in laboratory practice) by R. H. Müller and R. Schuhmann, Wissenschaftliche Verlagsgesellschaft Stuttgart (1996) or in the textbook "Introduction to Particle Technology" by M. Rhodes, published by Wiley & Sons (1998).

The free-flowing, fine powder can in turn be converted by suitable compaction or granulation processes into a coarse, very free-flowing, storable and substantially dust-free product. The term "dust-free" means that the product comprises only small proportions (<5%) of particle sizes below 100 µm in diameter. "Storable" in the sense of this invention means a product which can be stored for at least one (1) year or longer, preferably at least 1.5 years or longer, particularly preferably two (2) years or longer, in a dry and cool environment without any substantial loss (at most 5%) of the respective amino acid occurring.

The invention further relates to a method described in principle in WO 2007/042363 A1. To this end, a method is carried out which uses the fermentation broth obtained according to the invention, from which the biomass has been removed completely or partially, where appropriate, and which method comprises the following steps:

a) the pH is reduced to 4.0 to 5.2, in particular 4.9 to 5.1, by adding sulphuric acid and a molar sulphate/L-lysine ratio of from 0.85 to 1.2, preferably 0.9 to 1.0, particularly preferably >0.9 to <0.95, is established in the broth, where appropriate by adding one or more further sulphate-containing compound(s), and b) the mixture obtained in this way is concentrated by removal of water, and granulated where appropriate, where one or both of the following measures is/are carried out where appropriate before step a):

c) measurement of the molar sulphate/L-lysine ratio to ascertain the required amount of sulphate-containing compound(s)

d) addition of a sulphate-containing compound selected from the group of ammonium sulphate, ammonium bisulphate and sulphuric acid in appropriate ratios.

Where appropriate, furthermore, before step b), a salt of sulphurous acid, preferably alkali metal bisulphite, particularly preferably sodium bisulphite, is added in a concentration of from 0.01 to 0.5% by weight, preferably 0.1 to 0.3% by weight, particularly preferably 0.1 to 0.2% by weight, based on the fermentation broth.

Preferred sulphate-containing compounds which should be mentioned in the context of the abovementioned process steps are in particular ammonium sulphate and/or ammonium bisulphate or appropriate mixtures of ammonia and sulphuric acid and sulphuric acid itself.

The molar sulphate/L-lysine ratio V is calculated by the formula: $V=2\times[SO_4^{2-}]/[L\text{-lysine}]$. This formula takes account of the fact that the $SO_4^{2-}$ anion is doubly charged, or sulphuric acid is dibasic. A ratio of V=1 means that a stoichiometric composition $Lys_2$-$(H_2SO_4)$ is present, whereas the finding with a ratio of V=0.9 is a 10% sulphate deficit and with a ratio of V=1.1 is a 10% sulphate excess.

It is advantageous to employ during the granulation or compaction the usual organic or inorganic auxiliaries or carriers such as starch, gelatine, cellulose derivatives or similar substances, as normally used in the processing of food products or feeds as binders, gelling agents or thickeners, or further substances such as, for example, silicas, silicates (EP0743016A) or stearates.

It is further advantageous to treat the surface of the resulting granules with oils or fats as described in WO 04/054381. Oils which can be used are mineral oils, vegetable oils or mixtures of vegetable oils. Examples of such oils are soybean oil, olive oil, soybean oil/lecithin mixtures. In the same way, silicone oils, polyethylene glycols or hydroxyethylcellulose are also suitable. Treatment of the surfaces with said oils achieves an increased abrasion resistance of the product and a reduction in the dust content. The oil content in the product is 0.02 to 2.0% by weight, preferably 0.02 to 1.0% by weight, and very particularly preferably 0.2 to 1.0% by weight, based on the total amount of the feed additive.

Preferred products have a proportion of ≥97% by weight with a particle size of from 100 to 1800 μm, or a proportion of ≥95% by weight with a particle size of 300 to 1800 μm, in diameter. The proportion of dust, i.e. particles with a particle size<100 μm, is preferably >0 to 1% by weight, particularly preferably not exceeding 0.5% by weight.

However, alternatively, the product may also be absorbed on an organic or inorganic carrier known and customary in the processing of feeds, such as, for example, silicas, silicates, meals, brans, flours, starches, sugars or others, and/or be mixed and stabilized with customary thickeners or binders. Examples of use and processes therefor are described in the literature (Die Mühle+Mischfuttertechnik 132 (1995) 49, page 817).

Finally, the product can also be brought, by coating processes with film-formers such as, for example, metal carbonates, silicas, silicates, alginates, stearates, starches, gums and cellulose ethers, as described in DE-C-4100920, into a state which is stable to digestion by animal stomachs, especially the stomach of ruminants.

To establish a desired L-lysine concentration in the product, it is possible, depending on requirements, to add the L-lysine during the process in the form of a concentrate or, where appropriate, of a substantially pure substance or its salt in liquid or solid form. These can be added singly or as mixtures to the resulting or concentrated fermentation broth, or else during the drying or granulation process.

The invention further relates to a method for preparing a solid lysine-containing product, which method is described in principle in US 20050220933. This involves carrying out a method which uses the fermentation broth obtained according to the invention and which comprises the following steps:

a) filtration of the fermentation broth, preferably with a membrane filter, to result in a biomass-containing slurry and a filtrate;
b) concentration of the filtrate, preferably so as to result in a solids content of from 48 to 52% by weight;
c) granulation of the concentrate obtained in step b), preferably at a temperature of from 50° C. to 62° C.; and
d) coating of the granules obtained in c) with one or more of the coating agent(s).

The concentration of the filtrate in step b) can also be carried out in such a way that a solids content of >52 to ≤55% by weight, of >55 to ≤58% by weight or of >58 to ≤61% by weight is obtained.

The coating agents preferably used for the coating in step d) are selected from the group consisting of:
d1) the biomass obtained in step a);
d2) an L-lysine-containing compound, preferably selected from the group of L-lysine hydrochloride or L-lysine sulphate;
d3) an essentially L-lysine-free substance with an L-lysine content of <1% by weight, preferably <0.5% by weight, preferably selected from the group of starch, carrageenan, agar, silicas, silicates, meals, brans and flours; and
d4) a water-repellent substance, preferably selected from the group of oils, polyethylene glycols and liquid paraffins.

The L-lysine content is adjusted to a desired value by the measures corresponding to steps d1) to d4), in particular d1) to d3).

In the production of L-lysine-containing products, the ratio of the ions is preferably adjusted so that the molar ion ratio corresponding to the following formula:

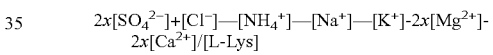

gives 0.68 to 0.95, preferably 0.68 to 0.90, particularly preferably 0.68 to 0.86, as described by Kushiki, et al., in US 20030152633.

In the case of L-lysine, the solid product produced in this way has, based on the fermentation broth, a lysine content (as lysine base) of from 10% by weight to 70% by weight or 20% by weight to 70% by weight, preferably 30% by weight to 70% by weight and very particularly preferably from 40% by weight to 70% by weight, based on the dry matter of the product. Maximum lysine base contents of 71% by weight, 72% by weight, 73% by weight are likewise possible.

The water content of the L-lysine-containing solid product is up to 5% by weight, preferably up to 4% by weight, and particularly preferably less than 3% by weight.

The strain DM1729 was deposited with the German collection of microorganisms and cell cultures under accession number DSM17576 on 16 Sep. 2005.

EXAMPLES

Example 1

Identification of a Trehalose Uptake System

For bacteria of the order Actinomycetales, which also includes *C. glutamicum*, trehalose metabolization has hitherto been described only for bacteria of the Streptomycetaceae family: *Streptomyces coelicolor* and *Streptomyces reticuli* utilize trehalose as carbon source. Gene expression analyses indicated an involvement in trehalose uptake of the components of an ABC transport system, encoded by agl3E, agl3F and agl3G, in *S. coelicolor* and of the ATPase subunit MsiK in *S. reticuli*. A Blast analysis of the *C. glutamicum* genomic sequence identified two open reading frames (cg2708 and cg0835) with high homology to *S. reticuli* msiK (GenBank accession no. CAA70125): the *C. glutamicum* protein encoded by cg2708 is 59% identical to *S. reticuli* MsiK (e-value 7e-125), but is the ATP-binding protein MusE of the MusEFGK$_2$ maltose transporter, the deletion of which does not affect trehalose utilization. The second protein, encoded by cg0835, is, at 58%, likewise highly identical to *S. reticuli* MsiK (e-value 8e-112). Sequence comparisons of *S. coelicolor* agl3E, agl3F and agl3G (accession no. NP 631226, NP 631225, NP 631224) with the *C. glutamicum* genomic sequence did not yield any further meaningful hits (e.g. 25% to 32% identity to genes of the ABC uptake system UgpAEBC which catalyses the uptake of glycerol 3-phosphate, and genes of the maltose uptake system MusEFGK$_2$).

Comparative sequence analysis therefore yields, as a possible trehalose uptake system in *C. glutamicum*, the open reading frame cg0835 and the open reading frames cg0834, cg0832 and cg0831 which are located in the immediate vicinity in the genomic sequence and which code for a substrate-binding protein and two permease components of an as yet uncharacterized ABC transporter (see FIG. 1 for arrangement).

Example 2

Construction of Vector pXMJ19_cg0831

The expression construct containing the reading frames cg0832, cg0834, cg0833, cg0832 and cg0831 was prepared by amplifying the corresponding gene region by means of a proof-reading polymerase (PRECISOR High-Fidelity DNA Polymerase, Biocat, Heidelberg, Germany) and ligating it into the pJet cloning vector (Fermentas, St. Leon-Roth, Germany). To this end, the following synthetic oligonucleotides (primers) were used:

```
primer cg0831for (SEQ ID No: 30):
5' GCTCTAGATGCGTTCTGCTCCTGACCTT 3' primer cg0831rev (SEQ ID No: 31):
5' CGGGATCCTTTGCGTTGCGATTCGGATT 3'
```

The primers shown were synthesized by MWG Biotech (Ebersberg, Germany). In each case, the recognition sequence for the restriction enzymes XbaI and BamHI, respectively, is underlined.

Figure 2:
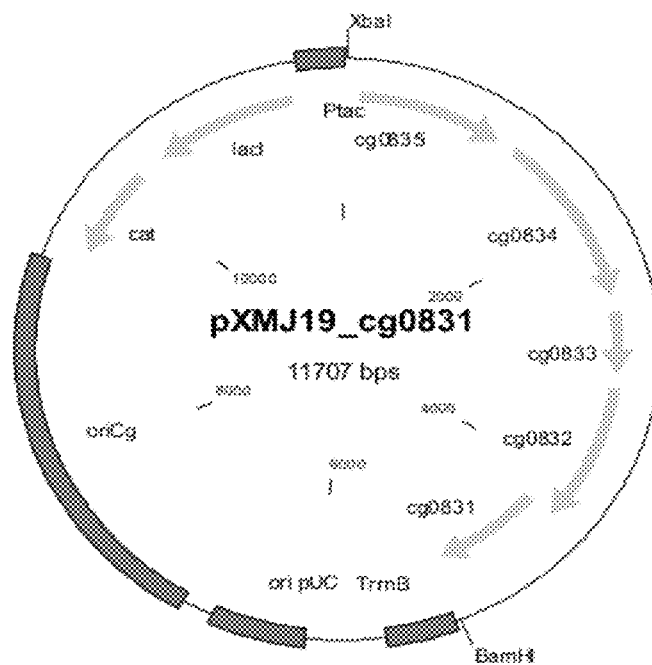
FIG. 2 is a schematic representation of expression construct pXMJ19-cg0831. Table 2 below summarizes the abbreviations and names used and also the meaning thereof. The base pair numbers indicated are approximations obtained within the limits of reproducibility of measurements.

The fragment obtained was then excised by the restriction enzymes XbaI and BamHI (New England Biolabs, Schwalbach, Germany) from the pJet vector and ligated into the pXMJ19 expression vector (Jakoby et al., 1999), which had previously been linearized with XbaI and BamHI and then dephosphorylated using Antarctic Phosphatase (New England Biolabs, Schwalbach, Germany). This was followed by transforming competent *E. coli* DH5αmcr cells with 5 µl of the ligation mixture. The clones obtained were screened by restriction of the prepared plasmids for those containing the desired insert. The plasmid has been named pXMJ19_cg0831 (see FIG. 2).

Example 3

Preparation of *C. glutamicum* Strains DM1933/pXMJ19 and DM1933/pXMJ19_cg0831

The plasmids described in Example 2, pXMJ19 and pXMJ19 cg0831, were electroporated into *Corynebacterium glutamicum* DM1933, using the electroporation method of Liebl, et al. (*FEMS Microbiological Letters* 53:299-303 (1989)).

The DM1933 strain is an aminoethylcystein-resistant mutant of *Corynebacterium glutamicum* ATCC13032 and has been described in a publication (Blombach, et al., *Appl. and Env. Microbiol.* 419-427 (2009)).

Plasmid-harbouring cells were selected by plating the electroporation mixture onto LB agar (Sambrook et al., Molecular cloning: a laboratory manual. $2^{nd}$ Ed. Cold Spring Harbor Laboratory Press, Cold Spring Harbor, N.Y., 1989) supplemented with 7.5 mg/l chloramphenicol. Plasmid DNA was isolated from in each case one transformant by the usual methods (Peters-Wendisch et al., *Microbiology* 144:915-927 (1998)) and checked by restriction cleavage with subsequent agarose gel electrophoresis.

The strains obtained were named DM1933/pXMJ19 and DM1933/pXMJ19 cg0831. The pXMJ19_cg0831 construct contains the reading frames cg0832, cg0834, cg0833, cg0832 and cg0831.

Example 4

Production of L-Lysine

The *C. glutamicum* strains obtained in Example 3, DM1933/pXMJ19 and DM1933/pXMJ19 cg0831, were cultured in a nutrient medium suitable for lysine production, and the lysine content in the culture supernatant was determined.

For this purpose, the strains were first incubated on an agar plate containing the appropriate antibiotic (brain-heart agar with chloramphenicol (7.5 mg/l)) at 33° C. for 24 hours. Starting from this agar plate culture, a preculture was inoculated (10 ml of medium in a 100 ml conical flask). The medium used for the preculture and the main culture was MM medium to which chloramphenicol (7.5 mg/l) was added. Table 4 gives an overview of the composition of the culturing medium used.

TABLE 4

| MM medium | |
|---|---|
| CSL (corn steep liquor) | 5 g/l |
| MOPS (morpholinopropanesulfonic acid) | 20 g/l |
| Glucose (autoclaved separately) | 50 g/l |
| Salts: | |
| $(NH_4)_2SO_4$ | 25 g/l |
| $KH_2PO_4$ | 0.1 g/l |
| $MgSO_4 * 7 H_2O$ | 1.0 g/l |
| $CaCl_2 * 2 H_2O$ | 10 mg/l |
| $FeSO_4 * 7 H_2O$ | 10 mg/l |
| $MnSO_4 * H_2O$ | 5.0 mg/l |
| Biotin (sterile-filtered) | 0.3 mg/l |
| Thiamine*HCl (sterile-filtered) | 0.2 mg/l |
| $CaCO_3$ | 25 g/l |

CSL, MOPS and the salt solution were adjusted to pH 7 with aqueous ammonia and autoclaved. The sterile substrate and vitamin solutions and the dry-autoclaved $CaCO_3$ were then added.

The preculture was incubated on a shaker at 250 rpm and 33° C. for 24 hours. A main culture was inoculated from this preculture such that the starting OD (660 nm) of the main culture was 0.1 OD.

Culturing was carried out in 10 ml volumes in a 100 ml conical flask with baffles at a temperature of 33° C. and 80% humidity.

After 20 and 40 hours (h) the OD at a measurement wavelength of 660 nm was determined using a Biomek 1000 (Beckmann Instruments GmbH, Munich). The amount of lysine produced was determined by ion exchange chromatography and post-column derivatization with ninhydrin detection, using an amino acid analyzer from Eppendorf-BioTronik (Hamburg, Germany). The trehalose concentration was determined by means of HPLC, using an analyzer from Dionex GmbH (65510 Idstein, Germany). Table 5 depicts the result of the experiment.

TABLE 5

Production of L-lysine and trehalose concentration measurement.

| Strain | L-Lysine HCl (g/l) 20 h | 40 h | OD (660 nm) 20 h | 40 h | Trehalose (g/l) 20 h | 40 h |
|---|---|---|---|---|---|---|
| DM1933/pXMJ19 | 11.84 | 13.65 | 14.04 | 13.12 | n.d. | 3.13 |
| DM1933/pXMJ19_cg0831 | 11.82 | 14.89 | 14.62 | 13.7 | n.d. | 0 |

All values are averages of 3 independent experiments with the strains listed;
n.d. = not determined.

The result indicates that trehalose is no longer produced as a by-product when lysine is produced from trehalose using a trehalose importer-expressing strain. It is furthermore evident that the yield of the desired product (L-lysine) is increased.

Example 5

Construction of Vector pK18mobsacB_Pgap_cg0832

A 1701 bp DNA fragment corresponding to the nucleotide sequence (SEQ ID No: 26) for overexpressing the genes cg0831 and cg0832 was prepared by de novo gene synthesis at GENEART AG (Regensburg, Germany).

The positions of nucleotides 613 to 1095 describe a promoter fragment from the application US20080050786 (SEQ ID NO:20), wherein a cleavage site for the NruI restriction enzyme was generated by mutating the nucleobase thymine in position 1079 to the nucleobase guanine, the nucleobase thymine in position 1080 to the nucleobase cytosine and the nucleobase thymine in position 1081 to the nucleobase guanine. In addition, a cleavage site for the SeaI restriction enzyme was generated by adding a linker sequence (SEQ ID NO:28) to the 5' end of the promoter sequence and is located in positions 607 to 612. The 489 bp promoter fragment obtained from this was functionally linked to the start codon of the gene cg0832.

The construct has a 600 bp flanking sequence in the downstream region (positions 1096 to 1695) and a 600 bp flanking sequence in the upstream (positions 7 to 606) region of the promoter, for integration of the promoter by means of homologous recombination.

Sequences containing cleavage sites for the restriction enzymes XbaI (positions 1 to 6) and HindIII (positions 1696 to 1701) were added to the flanking regions, thereby enabling the construct to be cloned into the exchange vector pK18mobsacB.

The 1701 bp fragment was digested with the XbaI and HindIII restriction enzymes and then subcloned into the mobilizable vector pK18mobsacB described by Schäfer, et al. (Gene 145:69-73 (1994)), in order to enable the promoter to integrate upstream of the gene cg0832. To this end, pK18mobsacB was digested with the XbaI and HindIII restriction enzymes. The vector prepared in this way was mixed with the fragment, and the mixture was treated with the Ready-To-Go T4 DNA ligase kit (Amersham-Pharmacia, Freiburg, Germany).

Subsequently, the E. coli strain S17-1 (Simon, et al., Bio/Technologie 1:784-791, (1993)) was transformed with the ligation mixture (Hanahan, In. DNA cloning. A practical approach. Vol. 1. ILR-Press, Cold Spring Harbor, N.Y., 1989). Plasmid-harbouring cells were selected by plating the transformation mixture onto LB agar (Sambrock, et al., Molecular Cloning: a laboratory manual. $2^{nd}$ Ed. Cold Spring Habor, New York, 1989) supplemented with 50 mg/l kanamycin.

Plasmid DNA was isolated from a transformant with the aid of the QIAprep Spin Miniprep kit from Qiagen and checked by restriction cleavage with the XbaI and HindIII enzymes and subsequent agarose gel electrophoresis. The plasmid is referred to as pK18mobsacB_Pgap_cg0832 and is depicted in FIG. 3.

Example 6

Preparation of C. glutamicum Strain DM1933_Pgap_cg0832

The aim was to introduce the mutation Pgap_cg0832 into the strain Corynebacterium glutamicum DM1933. The DM1933 strain is an aminoethylcysteine-resistant mutant of Corynebacterium glutamicum ATCC13032 and has been described in a publication (Blombach et al., Appl. and Env. Microbiol. 419-427 (2009)).

The vector pK18mobsacB_Pgap_cg0832 described in Example 5 was transferred by conjugation according to the protocol of Schäfer, et al. (J. Microbiol. 172:1663-1666 (1990)) into the C. glutamicum strain DM1933. Said vector cannot self-replicate in DM1933 and is retained in the cell only if it has integrated into the chromosome as a result of a recombination event. Transconjugants, i.e. clones with integrated pK18mobsacB_Pgap_cg0832, were selected by plating the conjugation mixture onto LB agar supplemented with 25 mg/l kanamycin and 50 mg/l nalidixic acid. Kanamycin-resistant transconjugants were then streaked out on LB-agar plates supplemented with kanamycin (25 mg/l) and incubated at 33° C. for 24 hours. Mutants in which the plasmid had been excised as a result of a second recombination event were selected by culturing the clones non-selectively in liquid LB medium for 30 hours, then streaking them out on LB agar supplemented with 10% sucrose and incubating at 33° C. for 24 hours.

Plasmid pK18mobsacB_Pgap_cg0832, like the starting plasmid pK18mobsacB, contains a copy of the sacB gene coding for Bacillus subtilis levansucrase, in addition to the kanamycin resistance gene. Sucrose-inducible expression of the sacB gene leads to the formation of levansucrase which catalyses the synthesis of the product levan which is toxic to C. glutamicum. Consequently, only those clones in which the integrated pK18mobsacB_Pgap_cg0832 has been excised as a result of a second recombination event grow on sucrose-supplemented LB agar. Depending on the location of the second recombination event in relation to the site of mutation, the mutation is incorporated during excision or the host chromosome remains in the original state.

Subsequently, a clone was identified in which the desired exchange, i.e. incorporation of the Pgap_cg0832 cassette into the chromosome, had occurred. To this end, 50 clones with the phenotype "growth in the presence of sucrose" and "no growth in the presence of kanamycin" were checked for integration of the Pgap_cg0832 cassette using the polymerase chain reaction (PCR). For this, the following synthetic oligonucleotides (primers) were used:

```
primer cg0832_1.p (SEQ ID NO: 28):
5' GCTGGAATACGGAGTGAACC 3' primer cg0832_2.p (SEQ ID NO: 29):
5' GGGATTGCCCAAGGGATAAG 3'
```

The primers shown were synthesized by MWG Biotech (Ebersberg, Germany). The primers cg0832_1.p and cg0832_2.p enable a 570 bp DNA fragment to be amplified in the case of the wild-type arrangement. The size of the amplicon is 1059 bp in the case of integration of the Pgap_cg0832 construct into the chromosome.

The PCR reactions were carried out using the Taq PCR core kit from Quiagen (Hilden, Germany), comprising *Thermus aquaticus* Taq DNA polymerase, in an Eppendorf Mastercycler (Hamburg, Germany). The conditions in the reaction mixture were adjusted according to the manufacturer's instructions. The PCR mixture was first subjected to an initial denaturation at 94° C. for 2 minutes. This was followed by 35 repeats of a denaturing step at 94° C. for 30 seconds, a step of binding the primers to the DNA at 57° C. for 30 seconds, and the extension step for extending the primers at 72° C. for 60 s. After the final extension step at 72° C. for 5 min, the products amplified in this way were checked by electrophoresis in an agarose gel.

In this way mutants were identified which contain the Pgap_cg0832 cassette in an integrated form, with one of the strains obtained being named *C. glutamicum* DM1933_Pgap_cg0832.

Example 7

Production of L-Lysine

The *C. glutamicum* strain DM1933_Pgap_cg0832 obtained in Example 6 and the starting strain DM1933 were cultured in a nutrient medium suitable for lysine production, and the lysine content in the culture supernatant was determined.

For this purpose, the strains were first incubated on an agar plate (brain-heart agar) at 33° C. for 24 hours. Starting from this agar plate culture, a preculture was inoculated (10 ml of medium in a 100 ml conical flask). The medium used for the preculture and the main culture was MM medium (see Table 4). CSL, MOPS and the salt solution were adjusted to pH 7 with aqueous ammonia and autoclaved. The sterile substrate and vitamin solutions and the dry-autoclaved $CaCO_3$ were then added.

The preculture was incubated on a shaker at 250 rpm and 33° C. for 24 hours. A main culture was inoculated from this preculture such that the starting OD (660 nm) of the main culture was 0.1 OD. Culturing was carried out in 10 ml volumes in a 100 ml conical flask with baffles at a temperature of 33° C. and 80% humidity.

After 20 and 40 hours (h) the OD at a measurement wavelength of 660 nm was determined using a Biomek 1000 (Beckmann Instruments GmbH, Munich). The amount of lysine produced was determined by ion exchange chromatography and post-column derivatization with ninhydrin detection, using an amino acid analyzer from Eppendorf-BioTronik (Hamburg, Germany). The trehalose concentration was determined by means of HPLC, using an analyzer from Dionex GmbH (65510 Idstein, Germany). Table 6 depicts the result of the experiment.

TABLE 6

Production of L-lysine and trehalose concentration measurement.

| Strain | L-Lysine HCl (g/l) | | OD (660 nm) | | Trehalose (g/l) | |
|---|---|---|---|---|---|---|
| | 20 h | 40 h | 20 h | 40 h | 20 h | 40 h |
| DM1933 | 12.83 | 13.65 | 14.75 | 12.19 | n.d. | 3.03 |
| DM1933_Pgap_cg0832 | 12.91 | 14.15 | 15.11 | 12.34 | n.d. | 0 |

All values are averages of 3 independent experiments with the strains listed;
n.d. = not determined.

The result indicates that trehalose is no longer produced as a by-product when lysine is produced from trehalose using a strain in which only expression of the trehalose importer subunits encoded by cg0832 and cg0831 (in both cases a permease subunit) is enhanced. It is furthermore evident that the yield of the desired product (L-lysine) is increased.

All references cited herein are fully incorporated by reference. Having now fully described the invention, it will be understood by one of skill in the art that the invention may be performed within a wide and equivalent range of conditions, parameters, and the like, without affecting the spirit or scope of the invention or any embodiment thereof.

What is claimed is:

1. An isolated *Corynebacterium glutamicum* bacterium which produces and/or secretes an L-amino acid during fermentation, wherein:
   a) compared to other bacteria of the same species and strain, said isolated bacterium comprises increased expression of polypeptides comprising the amino acid sequence of SEQ ID NO:8 and SEQ ID NO:10, wherein increased expression of said polypeptides is due to the presence of a larger number of DNA sequences encoding said polypeptides and/or due to DNA sequences encoding said polypeptides being functionally linked to a promoter which is stronger than a promoter of a gene encoding said polypeptides in wild type bacteria of the same species and strain;
   b) compared to other bacteria of the same species and strain, said isolated bacterium comprises increased trehalose importer activity, said activity being sufficient to reduce the amount of trehalose accumulated in fermentation broth by 70% or more when said isolated bacterium is cultured in a fermentation broth.

2. The isolated *Corynebacterium glutamicum* bacterium of claim 1, wherein compared to other bacteria of the same species and strain, said isolated bacterium comprises increased trehalose importer activity, said activity being sufficient to reduce the amount of trehalose accumulated in fermentation broth by 80% or more when said isolated bacterium is cultured in a fermentation broth.

3. The isolated *Corynebacterium glutamicum* bacterium of claim 1, wherein compared to other bacteria of the same species and strain, said isolated bacterium comprises increased trehalose importer activity, said activity being sufficient to reduce the amount of trehalose accumulated in fermentation broth by 90% or more when said isolated bacterium is cultured in a fermentation broth.

4. The isolated *Corynebacterium glutamicum* bacterium of claim 1, wherein compared to other bacteria of the same species and strain, said isolated bacterium comprises increased trehalose importer activity, said activity being sufficient to reduce the amount of trehalose accumulated in fermentation broth by 95% or more when said isolated bacterium is cultured in a fermentation broth.

5. The isolated *Corynebacterium glutamicum* bacterium of claim 1, wherein said L-amino acid is L-lysine.

6. The isolated *Corynebacterium glutamicum* bacterium of claim 1, wherein compared to other bacteria of the same species and strain, said isolated bacterium comprises increased trehalose importer activity, said activity being sufficient to reduce the amount of trehalose accumulated in fermentation broth by 90% or more when said isolated bacterium is cultured in a fermentation broth.

7. The isolated *Corynebacterium glutamicum* bacterium of claim 1, wherein, compared to other bacteria of the same species and strain, said isolated bacterium comprises increased expression of an additional polypeptide, wherein said additional polypeptide comprises the amino acid sequence of SEQ ID NO:4, and wherein increased expression of said additional polypeptide is due to the presence of a larger number of DNA sequences encoding said additional polypeptide and/or due to DNA sequences encoding said additional polypeptide being functionally linked to a promoter which is stronger than a promoter of a gene encoding said additional polypeptide in wild type bacteria of the same species and strain.

8. The isolated *Corynebacterium glutamicum* bacterium of claim 7, wherein compared to other bacteria of the same species and strain, said isolated bacterium comprises increased trehalose importer activity, said activity being sufficient to reduce the amount of trehalose accumulated in fermentation broth by 80% or more when said isolated bacterium is cultured in a fermentation broth.

9. The isolated *Corynebacterium glutamicum* bacterium of claim 7, wherein compared to other bacteria of the same species and strain, said isolated bacterium comprises increased trehalose importer activity, said activity being sufficient to reduce the amount of trehalose accumulated in fermentation broth by 90% or more when said isolated bacterium is cultured in a fermentation broth.

10. The isolated *Corynebacterium glutamicum* bacterium of claim 7, wherein said L-amino acid is L-lysine.

11. The isolated *Corynebacterium glutamicum* bacterium of claim 1, wherein, compared to other bacteria of the same species and strain, said isolated bacterium comprises increased expression of an additional polypeptide, wherein said additional polypeptide comprises the amino acid sequence of SEQ ID NO:6, and wherein increased expression of said additional polypeptide is due to the presence of a larger number of DNA sequences encoding said additional polypeptide and/or due to DNA sequences encoding said additional polypeptide being functionally linked to a promoter which is stronger than a promoter of a gene encoding said additional polypeptide in wild type bacteria of the same species and strain.

12. The isolated *Corynebacterium glutamicum* bacterium of claim 11, wherein compared to other bacteria of the same species and strain, said isolated bacterium comprises increased trehalose importer activity, said activity being sufficient to reduce the amount of trehalose accumulated in fermentation broth by 80% or more when said isolated bacterium is cultured in a fermentation broth.

13. The isolated *Corynebacterium glutamicum* bacterium of claim 11, wherein compared to other bacteria of the same species and strain, said isolated bacterium comprises increased trehalose importer activity, said activity being sufficient to reduce the amount of trehalose accumulated in fermentation broth by 90% or more when said isolated bacterium is cultured in a fermentation broth.

14. The isolated *Corynebacterium glutamicum* bacterium of claim 11, wherein said L-amino acid is L-lysine.

15. The isolated *Corynebacterium glutamicum* bacterium of claim 1, wherein, compared to other bacteria of the same species and strain, said isolated bacterium comprises increased expression of additional polypeptides, wherein said additional polypeptides comprise the amino acid sequence of SEQ ID NO:4 and the amino acid sequence of SEQ ID NO:6, and wherein increased expression of said additional polypeptides is due to the presence of a larger number of DNA sequences encoding said additional polypeptides and/or due to DNA sequences encoding said additional polypeptides being functionally linked to a promoter which is stronger than a promoter of a gene encoding said additional polypeptide in wild type bacteria of the same species and strain.

16. The isolated *Corynebacterium glutamicum* bacterium of claim 15, wherein, compared to other bacteria of the same species and strain, said isolated bacterium comprises increased trehalose importer activity, said activity being sufficient to reduce the amount of trehalose accumulated in fermentation broth by 80% or more when said isolated bacterium is cultured in a fermentation broth.

17. The isolated *Corynebacterium glutamicum* bacterium of claim 15, wherein, compared to other bacteria of the same species and strain, said isolated bacterium comprises increased trehalose importer activity, said activity being sufficient to reduce the amount of trehalose accumulated in fermentation broth by 90% or more when said isolated bacterium is cultured in a fermentation broth.

18. The isolated *Corynebacterium glutamicum* bacterium of claim 15, wherein said L-amino acid is L-lysine.

19. A method for the fermentative production of an L-amino acid, comprising the steps of:
   a) culturing the isolated bacterium of claim 1 in a medium to produce a fermentation broth, wherein said isolated bacterium produces and/or secretes said L-amino acid;
   b) accumulating said L-amino acid in the fermentation broth of a); and
   c) recovering said L-amino acid.

20. The method of claim 19, wherein said L-amino acid is L-lysine.

* * * * *